(12) United States Patent
Reyes et al.

(10) Patent No.: US 8,722,742 B2
(45) Date of Patent: May 13, 2014

(54) **CHEMICAL COMPOUNDS HAVING ANTIVIRAL ACTIVITY AGAINST DENGUE VIRUS AND OTHER *FLAVIVIRUSES***

(75) Inventors: Yuliet Mazola Reyes, Havana (CU); Glay Chinea Santiago, Ciudad de la Habana (CU); Osmany Guirola Cruz, Ciudud Habana (CU); Roberto Vera Alvarez, Havana (CU); Vivian Huerta Galindo, Ciudad de la Habana (CU); Noralvis Fleitas Salazar, Ciudad Habana (CU); Alexis Musacchio Lasa, Havana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 559 days.

(21) Appl. No.: 12/919,416

(22) PCT Filed: Feb. 27, 2009

(86) PCT No.: PCT/CU2009/000002
§ 371 (c)(1),
(2), (4) Date: Nov. 22, 2010

(87) PCT Pub. No.: WO2009/106019
PCT Pub. Date: Sep. 3, 2009

(65) Prior Publication Data
US 2011/0065686 A1 Mar. 17, 2011

(30) Foreign Application Priority Data
Feb. 29, 2008 (CU) .................. 2008-0028

(51) Int. Cl.
*A01N 41/06* (2006.01)
*A61K 31/18* (2006.01)
*A61K 31/535* (2006.01)
*A61K 31/497* (2006.01)
*A61K 31/4965* (2006.01)
*A01N 43/40* (2006.01)
*A61K 31/445* (2006.01)

(52) U.S. Cl.
USPC ..... 514/602; 514/604; 514/231.2; 514/231.5; 514/252.12; 514/255.01; 514/255.05; 514/315; 514/316

(58) Field of Classification Search
USPC .............. 514/602, 604, 231.2, 231.5, 252.12, 514/255.01, 255.05, 316, 315
See application file for complete search history.

(56) References Cited

FOREIGN PATENT DOCUMENTS

| EP | 2022506 | 2/2009 |
|---|---|---|
| WO | WO9831814 | 7/1998 |
| WO | WO03008571 | 1/2003 |
| WO | WO2009032975 | 3/2009 |

OTHER PUBLICATIONS

Vilar et al., "Probabilistic Neural Network Model for the In Silico Evaluation of Anti-HIV Activity and Mechanism of Action," Journal of Medicinal Chemistry, 2006, vol. 49, No. 3, pp. 1118-1124.
Marrero-Ponce, et al., "Ligand-Based Virtual Screening and in Silico Design of New Antimalarial Compounds Using Nonstochastic and Stochastic Total and Atom-Type Quadratic Maps," Journal of Chemical Information and Modeling, 2005, 45, pp. 1082-1100.
Cushion et al., "A Cytotoxicity Assay for Evaluation of Candidate Anti-*Pneumocystis carinii* Agents," Antimicrobial Agents and Chemotherapy, Feb. 1997, vol. 41, No. 2, pp. 379-384.
Santos et al., "Synthesis and in vitro anti *Mycobacterium tuberculosis* activity of a series of phthalimide derivatives," Bioorganic & Medicinal Chemistry, 17, 2009, pp. 3795-3799.

*Primary Examiner* — Kara R McMillian
(74) *Attorney, Agent, or Firm* — Hoffmann & Baron LLP

(57) ABSTRACT

Use of chemical compounds obtained in silico for the preparation of pharmaceutical compositions to attenuate or inhibit Dengue virus infection. Particularly, through the interference or the modulation of several stages of viral replication cycle related with the entry of virus into host cells and the assembly of mature progeny virions. The invention also comprises the use of such pharmaceutical compositions for prophylactic and/or therapeutic treatment of infection caused by all four serotypes of Dengue virus and other flaviviruses.

1 Claim, 4 Drawing Sheets

(a) Anchor A-SIJ023

(b) Anchor A-SIJ118

(c) Anchor A-SIJ121

US 8,722,742 B2

Figure 1:
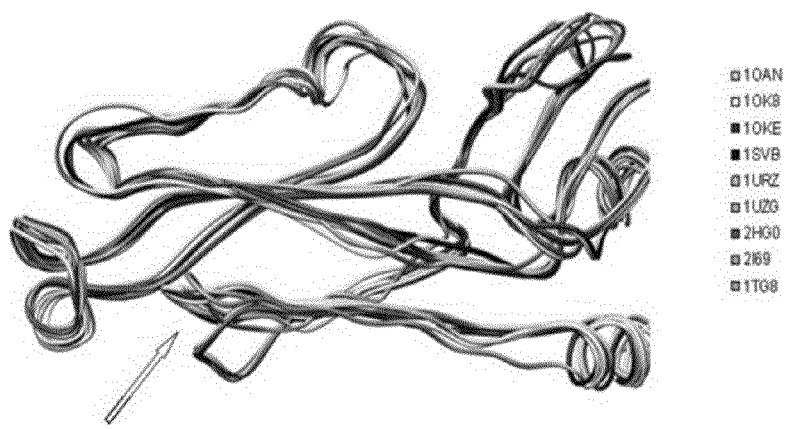

CHEMICAL COMPOUNDS HAVING ANTIVIRAL ACTIVITY AGAINST DENGUE VIRUS AND OTHER *FLAVIVIRUSES*

CLAIM OF PRIORITY

This application is the U.S. National Phase of, and Applicants claim priority from, International Application Number PCT/CU2009/000002 filed 27 Feb. 2009 and Cuban Patent Application No. 2008-0028 filed 29 Feb. 2008, which are incorporated herein by reference.

FIELD OF APPLICATION

The invention is related to the pharmaceutical industry, specifically describes the use of chemical compounds containing two distinctive functionally substructures [C]-[A] to affect or to inhibit different events of Dengue virus replication cycle related with the virus entry into host cells and the assembly of progeny virions. Such chemical compounds are useful for the prophylactic and/or the therapeutic treatment of infection caused by all four serotypes of Dengue virus and other flaviviruses.

STATE OF THE ART

The genus flavivirus comprises about 70 viruses including major pathogens responsible for high rates of morbidity and mortality in animals and humans, such as Dengue virus, West Nile virus, Tick-borne Encephalitis virus, Japanese encephalitis virus, Yellow fever virus, virus of St. Louis encephalitis and Murray Valley virus. However, there is no specific therapy available for the treatment of flavivirus infection and at present vaccines approved for human use are directed against only three viruses from this genus.

Among flavivirus, Dengue virus is one of the major health problems worldwide, especially in tropical and sub-tropical. Dengue virus is grouped into four serotypes: DEN1, DEN2, DEN3 and DEN4 and is transmitted to humans by vectors, mainly *Aedes aegypti* mosquito. The patient infected with Dengue virus may be asymptomatic or symptomatic, with clinical symptoms such as undifferentiated fever (UF), dengue fever (DF) and two more severe and occasionally fatal ones, called dengue hemorrhagic fever (DHF) and dengue shock syndrome (DSS) (Guha-Sapir, D. y Schimmer, B. (2005) Dengue fever: new paradigms for a changing epidemiology. *Emerg. Themes. Epidemiol.* 2:1-10).

Despite the importance of Dengue to public health, there are currently no vaccines or antiviral drugs available against this disease (Chaturvedi, U. C., Shrivastava, R., y Nagar, R. (2005) Dengue vaccines: problems and prospects. *Indian J Med. Res.* 121:639-652). Neither is there a specific treatment; therapy is based on control symptoms and compensate adequately the effects of dehydration and bleeding, while the body produces neutralizing antibodies against the virus. Vector control is the only method of preventing dengue infection but is often ineffective (Rico-Hesse, R. (2003) Microevolution and virulence of dengue viruses. *Adv. Virus Res.* 59:315-341).

The major impediments to dengue vaccine development are lack of a better understanding about pathogenesis of DHF and absence of a satisfactory animal model. In addition, infection with one serotype does not confer long-term protective immunity against reinfection with the three remaining serotypes (SABIN, A. B. (1952) Research on dengue during World War II. *Am J Trop. Med Hyg.* 1:30-50); even worse secondary or tertiary heterologous infections have been associated with DHF/DSS (Halstead, S. B., Nimmannitya, S., y Cohen, S. N. (1970) Observations related to pathogenesis of dengue hemorrhagic fever. IV. Relation of disease severity to antibody response and virus recovered. *Yale J Biol Med.* 42:311-328. Halstead, S. B. (1988) Pathogenesis of dengue: challenges to molecular biology. *Science.* 239:476-481). The effect known as antibody-dependent amplification (ADA) plays an important role in pathogenesis of DHF/DSS (Mady, B. J., Erbe, D. V., Kurane, I., Fanger, M. W., y Ennis, F. A. (1991) Antibody-dependent enhancement of dengue virus infection mediated by bispecific antibodies against cell surface molecules other than Fc gamma receptors. *J. Immunol.* 147:3139-3144). Therefore, an effective vaccine has to be tetravalent and able to induce simultaneously a protective neutralizing antibody response against all four serotypes of Dengue virus.

Live attenuated tetravalent dengue vaccines are the most promising vaccine candidates (Chaturvedi, U. C., Shrivastava, R., y Nagar, R. (2005) Dengue vaccines: problems and prospects. *Indian J Med. Res.* 121: 639-652. Edelman, R. (2007) Dengue vaccines approach the finish line. *Clin Infect. Dis.* 45:56-60). These have been developed by combining all four serotypes of attenuated Dengue virus into a tetravalent formulation; the viruses were obtained by serial passages in primary dog kidney cells (Bhamarapravati, N. y Sutee, Y. (2000) Live attenuated tetravalent dengue vaccine. *Vaccine.* 18:44-47) or by recombinant DNA technology through introduction of specific mutations into an infectious viral cDNA clone (Durbin, A. P., Karron, R. A., Sun, W., Vaughn, D. W., Reynolds, M. J., Perreault, J. R., Thumar, B., Men, R., Lai, C. J., Elkins, W. R., Chanock, R. M., Murphy, B. R., y Whitehead, S. S. (2001) Attenuation and immunogenicity in humans of a live dengue virus type-4 vaccine candidate with a 30 nucleotide deletion in its 3'-untranslated region. *Am J Trop. Med. Hyg.* 65:405-413) or by insertion of genes encoding structural proteins (envelope protein and premembrane protein) into attenuated strains of Dengue virus or yellow fever 17D vaccine strain (Guirakhoo, F., Pugachev, K., Arroyo, J., Miller, C., Zhang, Z. X., Weltzin, R., Georgakopoulos, K., Catalan, J., Ocran, S., Draper, K., y Monath, T. P. (2002) Viremia and immunogenicity in nonhuman primates of a tetravalent yellow fever-dengue chimeric vaccine: genetic reconstructions, dose adjustment, and antibody responses against wild-type dengue virus isolates. *Virology.* 298:146-159). Live attenuated tetravalent dengue vaccine candidates currently in clinical trials (phase 1 and phase 2) have proven to be safe and immunogenic (Edelman, R., Wasserman, S. S., Bodison, S. A., Putnak, R. J., Eckels, K. H., Tang, D., Kanesa-Thasan, N., Vaughn, D. W, Innis, B. L., y Sun, W. (2003) Phase I trial of 16 formulations of a tetravalent live-attenuated dengue vaccine. *Am J Trop. Med Hyg.* 69:48-60. Sabchareon, A., Lang, J., Chanthavanich, P., Yoksan, S., Forrat, R., Attanath, P., Sirivichayakul, C., Pengsaa, K., Pojjaroen-Anant, C., Chambonneau, L., Saluzzo, J. F., y Bhamarapravati, N. (2004) Safety and immunogenicity of a three dose regimen of two tetravalent live-attenuated dengue vaccines in five-to twelve-year-old That children. *Pediatr. Infect. Dis. J.* 23:99-109. Sabchareon, A., Lang, J., Chanthavanich, P., Yoksan, S., Forrat, R., Attanath, P., Sirivichayakul, C., Pengsaa, K., Pojjaroen-Anant, C., Chokejindachai, W., Jagsudee, A., Saluzzo, J. F., y Bhamarapravati, N. (2002) Safety and immunogenicity of tetravalent live-attenuated dengue vaccines in That adult volunteers: role of serotype concentration, ratio, and multiple doses. *Am J Trop. Med. Hyg.* 66:264-272. Kanesa-Thasan, N., Sun, W, Kim-Ahn, G., Van Albert, S., Putnak, J. R., King, A., Raengsakulsrach, B., Christ-Schmidt, H., Gilson, K., Zahradnik, J. M., Vaughn, D. W., Innis, B. L., Saluzzo, J. F., y Hoke, C. H., Jr. (2001) *Safety and immunogenicity of attenuated dengue virus vaccines (Aventis Pasteur) in human volunteers. Vaccine.* 19:3179-3188) just like monovalent formulations of two chimeric tetravalent candidates (ChimericVax DEN-2 and rDEN4Δ30) (Guirakhoo, F., Kitchener, S., Morrison, D., Forrat, R., McCarthy, K., Nichols, R., Yoksan, S., Duan, X., Ermak, T. H., Kanesa-Thasan, N., Bedford, P., Lang, J., Quentin-Millet, M. J., y Monath, T. P. (2006) Live attenuated chimeric yellow fever dengue type 2 (ChimeriVax-DEN2) vaccine: Phase I clinical trial for safety and immunogenicity: effect of yellow fever pre-immunity in induction of cross neutralizing antibody responses to all 4 dengue serotypes. *Hum. Vaccin.* 2:60-67. Durbin, A. P., Whitehead, S. S., McArthur, J., Perreault, J. R., Blaney, J. E., Jr., Thumar, B., Murphy, B. R., y Karron, R. A. (2005) rDEN4delta30, a live attenuated dengue virus type 4 vaccine candidate, is safe, immunogenic, and highly infectious in healthy adult volunteers. *J. Infect. Dis.* 191:710-718). Other vaccine candidates have been developed using different strategies, such as inactivated virus vaccines, protein subunits vaccines and DNA vaccines (Hombach, J. (2007) Vaccines against dengue: a review of current candidate vaccines at advanced development stages. *Rev Panam. Salud Pública.* 21:254-260). Several of these candidates induce protective immune response in animal models (Eckels, K. H. y Putnak, R. (2003) Formalin-inactivated whole virus and recombinant subunit flavivirus vaccines. *Adv. Virus Res.* 61:395-418. Hermida, L., Bernardo, L., Martin, J., Alvarez, M., Prado, I., Lopez, C., Sierra, B. L., Martinez, R., Rodriguez, R., Zulueta, A., Perez, A. B., Lazo, L., Rosario, D., Guillen, G., y Guzman, M. G. (2006) A recombinant fusion protein containing the domain III of the dengue-2 envelope protein is immunogenic and protective in nonhuman primates. *Vaccine.* 24:3165-3171. Raviprakash, K., Apt, D., Brinkman, A., Skinner, C., Yang, S., Dawes, G., Ewing, D., Wu, S. J., Bass, S., Punnonen, J., y Porter, K. (2006) A chimeric tetravalent dengue DNA vaccine elicits neutralizing antibody to all four virus serotypes in rhesus macaques. *Virology.* 353:166-173).

Live attenuated virus vaccines are more advantageous viral vaccines comparing with non-replicating ones, because induce long-term antibody response, require a smaller number of inoculations and are generally less costly. However, development of a tetravalent formulation has several disadvantages, such as achieve the appropriate level of attenuation of each serotype to ensure minimum reactogenicity and maximum immunogenicity (Edelman, R., Wasserman, S. S., Bodison, S. A., Putnak, R. J., Eckels, K. H., Tang, D., Kanesa-Thasan, N., Vaughn, D. W., Innis, B. L., y Sun, W. (2003) Phase I trial of 16 formulations of a tetravalent live-attenuated dengue vaccine. *Am J Trop. Med. Hyg.* 69:48-60; avoid interference between different Dengue virus serotypes (Raviprakash, K., Apt, D., Brinkman, A., Skinner, C., Yang, S., Dawes, G., Ewing, D., Wu, S. J., Bass, S., Punnonen, J., y Porter, K. (2006) A chimeric tetravalent dengue DNA vaccine elicits neutralizing antibody to all four virus serotypes in rhesus macaques. *Virology.* 353: 166-173); ensure similar levels of protection against all serotypes and confirm that vaccine is safe and immunogenic in individuals previously infected with other flavivirus. Recent studies demonstrated that immunization with the monovalent chimeric ChimericVax DEN-2 vaccine candidate in yellow fever-immune individuals does not cause interference Live attenuated chimeric yellow fever dengue type 2 (ChimeriVax-DEN2) vaccine: Phase I clinical trial for safety and immunogenicity: effect of yellow fever pre-immunity in induction of cross neutralizing antibody responses to all 4 dengue serotypes. There are other limitations on the development of live attenuated virus vaccines, since it can not be discount the possibility of recombination between vaccine strain and wild virus giving rise to a new virus with undesired properties or causing the reversion to virulent phenotype. Furthermore, these vaccines are generally contraindicated for immunocompromised individuals and those infected with Human Immunodeficiency Virus (Edelman, R. (2007) Dengue vaccines approach the finish line. *Clin Infect. Dis.* 45:56-60). In addition, the tetravalent formulation requires a multiple dosage immunization regimen.

The antiviral therapy represents a good alternative for treatment of dengue disease, especially when there are several obstacles (above-mentioned) which make it impossible to obtain an effective vaccine in short-term. The inhibitors are designed to block key processes of viral replication cycle such as entry of virus into host cell (Talarico, L. B., Pujol, C. A., Zibetti, R. G., Faria, P. C., Noseda, M. D., Duarte, M. E., y Damonte, E. B. (2005) The antiviral activity of sulfated polysaccharides against dengue virus is dependent on virus serotype and host cell. *Antiviral Res.* 66:103-110. Ono, L., Wolfinger, W, Rocco, I. M., Coimbra, T. L., Gorin, P. A., y Sierakowski, M. R. (2003) In vitro and in vivo antiviral properties of sulfated galactomannans against yellow fever virus (BeH111 strain) and dengue 1 virus (Hawaii strain). *Antiviral Res.* 60:201-208. Pujol, C. A., Estevez, J. M., Carlucci, M. J., Ciancia, M., Cerezo, A. S., y Damonte, E. B. (2002) Novel DL-galactan hybrids from the red seaweed Gymnogongrus torulosus are potent inhibitors of herpes simplex virus and dengue virus. *Antivir. Chem. Chemother.* 13:83-89), processing of viral polyprotein (Chanprapaph, S., Saparpakorn, P., Sangma, C., Niyomrattanakit, P., Hannongbua, S., Angsuthanasombat, C., y Katzenmeier, G. (2005) Competitive inhibition of the dengue virus NS3 serine protease by synthetic peptides representing polyprotein cleavage sites. *Biochem Biophys Res Commun.* 330:1237-1246), viral genome replication (Migliaccio, G., Tomassini, J. E., Carroll, S. S., Tomei, L., Altamura, S., Bhat, B., Bartholomew, L., Bosserman, M. R., Ceccacci, A., Colwell, L. F., Cortese, R., De Francesco, R., Eldrup, A. B., Getty, K. L., Hou, X. S., LaFemina, R. L., Ludmerer, S. W., MacCoss, M., McMasters, D. R., Stahlhut, M. W., Olsen, D. B., Hazuda, D. J., y Flores, O. A. (2003) Characterization of resistance to non-obligate chain-terminating ribonucleoside analogs that inhibit hepatitis C virus replication in vitro. *J Biol. Chem.* 278: 49164-49170) and viral particle assembly (Courageot, M. P., Frenkiel, M. P., Dos Santos, C. D., Deubel, V., y Despres, P. (2000) Alpha-glucosidase inhibitors reduce dengue virus production by affecting the initial steps of virion morphogenesis in the endoplasmic reticulum. *J. Virol.* 74: 564-572. Whitby, K., Pierson, T. C., Geiss, B., Lane, K., Engle, M., Zhou, Y., Doms, R. W., y Diamond, M. S. (2005) Castanospermine, a potent inhibitor of dengue virus infection in vitro and in vivo. *J. Virol.* 79: 8698-8706). Inhibitors have been identified using various methods including high-throughput screening (Novartis Institute for Tropical Diseases. (2005) New technologies for high-throughput screening and lead discovery of anti-viral compounds. *Dengue Digest.* 2:1-2), rational design based on the crystallographic structure of viral proteins (Hrobowski, Y. M., Garry, R. F., y Michael, S. F. (2005) Peptide inhibitors of dengue virus and West Nile virus infectivity. *Virol. J.* 2: 49-59), virtual screening of large chemical compounds libraries (Yang, J. M., Chen, Y. F., Tu, Y. Y., Yen, K. R., y Yang, Y. L. (2007) Combinatorial computational approaches to identify tetracycline derivatives as flavivirus inhibitors. *PLoS. ONE.* 2: 428-437), assessment of known inhibitors against other flavivirus (Migliaccio, G., Tomassini, J. E., Carroll, S. S., Tomei, L., Altamura, S., Bhat, B., Bartholomew, L., Bosserman, M. R., Ceccacci, A., Colwell, L. F., Cortese, R., De Francesco, R., Eldrup, A. B., Getty, K. L., Hou, X. S., LaFemina, R. L., Ludmerer, S. W., MacCoss, M., McMasters, D. R., Stahlhut, M. W., Olsen, D. B., Hazuda, D. J., y Flores, O. A. (2003) Characterization of resistance to non-obligate chain-terminating ribonucleoside analogs that inhibit hepatitis C virus replication in vitro. *J Biol. Chem.* 278: 49164-49170), antisense RNA gene therapy (Snapp, M. B. (1992) Occupational stress, social support, and depression among black and white professional-managerial women. *Women Health.* 18: 41-79. Holden, K. L., Stein, D. A., Pierson, T. C., Ahmed, A. A., Clyde, K., Iversen, P. L., y Harris, E. (2006) Inhibition of dengue virus translation and RNA synthesis by a morpholino oligomer targeted to the top of the terminal 3' stem-loop structure. *Virology.* 344: 439-452), passive immunity (Goncalvez, A. P., Men, R., Wernly, C., Purcell, R. H., y Lai, C. J. (2004) Chimpanzee Fab fragments and a derived humanized immunoglobulin G1 antibody that efficiently cross-neutralize dengue type 1 and type 2 viruses. *J. Virol.* 78: 12910-12918) and others. Among the viral proteins used as targets are included structural protein such as envelope glycoprotein and non-structural ones with protease/helicase activity and polymerase/methyltransferase activity named as NS3 and NS5 respectively.

Blocking virus entry into cell constitutes a very attractive strategy for antiviral design because it prevents the onset of infection. In the case of Dengue virus, the envelope protein is the target to attack (E protein). This protein is the main determinant antigen of Dengue virus and is responsible for key events required during entry into host cell, including recognition of cellular receptors (Crill, W. D. y Roehrig, J. T. (2001) Monoclonal antibodies that bind to domain III of dengue virus E glycoprotein are the most efficient blockers of virus adsorption to Vero cells. *J. Virol.* 75:7769-7773) and fusion between viral and host membrane (Allison, S. L., Schalich, J., Stiasny, K., Mandl, C. W., y Heinz, F. X. (2001) Mutational evidence for an internal fusion peptide in flavivirus envelope protein E. *J. Virol.* 75:4268-4275).

The E protein belongs to class II fusion proteins and consists of three domains I, II and III. Domain I comprise amino terminal region (residues 1-51, 133-192 and 281-295 in Dengue virus DEN2) but it is located in the center of monomer in the three-dimensional structure. Domain II or dimerization domain (residues 52-132 and 193-280) is composed of two elongations that emanate from domain I. Each elongation contains a loop at its tip, one loop is the fusion peptide (termed the "cd" loop, residues 100-108) and the other loop corresponds to "ij" loop (residues 243-248). The "hinge" is another interesting region wich also belongs to domain II and is located in the interface domain I-II. Domain III (residues 296-395) has a typical immunoglobulin-like fold and contains binding sites for cellular receptors. The "stem" region (residues 396-447) connects domain III to transmembrane domain.

The E protein is associated with precursor membrane protein (preM protein) forming heterodimers in immature virion (intracellular form of the virus prior to the exocytosis) (Zhang, Y., Corver, J., Chipman, P. R., Zhang, W, Pletnev, S. V., Sedlak, D., Baker, T. S., Strauss, J. H., Kuhn, R. J., y Rossmann, M. G. (2003) Structures of immature flavivirus particles. *EMBO J.* 22:2604-2613). A substantial portion of prM protein covers E protein protecting it against premature fusion while it passes through the acidic environment of the trans-Glogi network (TGN) (Guirakhoo, F., Bolin, R. A., y Roehrig, J. T. (1992) The Murray Valley encephalitis virus prM protein confers acid resistance to virus particles and alters the expression of epitopes within the R2 domain of E glycoprotein. *Virology.* 191:921-931). Processing of prM protein by cellular proteases destabilize the interaction preM-E and promote formation of E protein dimers in infectious mature virion. Then, the mature virions are released into the extracellular medium. After entering host cells by receptor-mediated endocytosis, viruses are exposed to low pH in endosome which promotes reversibly dissociation of E protein dimers into irreversibly trimers (Allison, S. L., Schalich, J., Stiasny, K., Mandl, C. W., Kunz, C., y Heinz, F. X. (1995) Oligomeric rearrangement of tick-borne encephalitis virus envelope proteins induced by an acidic pH. *J. Virol.* 69: 695-700). The transition from dimer to trimer experimented by E protein is closely related with the fusion process.

The development of Dengue virus inhibitors to block virus entry into host cell could be based on at least one of the following strategies: interference of the interaction between E protein and cellular receptors or inhibition of the fusion process between viral membrane and host endosomal membrane.

The first strategy for antiviral design has been little exploited due to lack of knowledge about the mechanism of virus Dengue attachment to the cell. Although in recent years some molecules have been proposed as potential receptors in certain cellular types (Chen, Y. C., Wang, S. Y., y King, C. C. (1999) Bacterial lipopolysaccharide inhibits dengue virus infection of primary human monocytes/macrophages by blockade of virus entry via a CD14-dependent mechanism. *J. Virol.* 73: 2650-2657. Tassaneetrithep, B., Burgess, T. H., Granelli-Piperno, A., Trumpfheller, C., Finke, J., Sun, W., Eller, M. A., Pattanapanyasat, K., Sarasombath, S., Birx, D. L., Steinman, R. M., Schlesinger, S., y Marovich, M. A. (2003) DC-SIGN (CD209) mediates dengue virus infection of human dendritic cells. J Exp Med. 197: 823-829. Hilgard, P. y Stockert, R. (2000) Heparan sulfate proteoglycans initiate dengue virus infection of hepatocytes. *Hepatology.* 32:1069-1077). One of these molecules is heparin sulfate (HS) (Chen, Y., Maguire, T., Hileman, R. E., Fromm, J. R., Esko, J. D., Linhardt, R. J., y Marks, R. M. (1997) Dengue virus infectivity depends on envelope protein binding to target cell heparan sulfate. *Nat. Med.* 3:866-871), whose discovery led the identification of similar compounds that interfere in vitro host cell receptor recognition event (Talarico, L. B., Pujol, C. A., Zibetti, R. G., Faria, P. C., Noseda, M. D., Duarte, M. E., y Damonte, E. B. (2005) The antiviral activity of sulfated polysaccharides against dengue virus is dependent on virus serotype and host cell. *Antiviral Res.* 66:103-110. Pujol, C. A., Estevez, J. M., Carlucci, M. J., Ciancia, M., Cerezo, A. S., y Damonte, E. B. (2002) Novel DL-galactan hybrids from the red seaweed Gymnogongrus torulosus are potent inhibitors of herpes simplex virus and dengue virus. *Antivir. Chem. Chemother.* 13:83-89. Ono, L., Wollinger, W, Rocco, I. M., Coimbra, T. L., Gorin, P. A., y Sierakowski, M. R. (2003) In vitro and in vivo antiviral properties of sulfated galactomannans against yellow fever virus (BeH111 strain) and dengue 1 virus (Hawaii strain). *Antiviral Res.* 60:201-208. Shigeta, S., Mori, S., Kodama, E., Kodama, J., Takahashi, K., y Yamase, T. (2003) Broad spectrum anti-RNA virus activities of titanium and vanadium substituted polyoxotungstates. *Antiviral Res.* 58:265-271).

Recently it was demonstrated that one of the HS polysulphated mimetics (IP-88) induces protective effect in mice infected with Dengue virus. However, its use in vivo as antivirals is restricted mainly due to its anticoagulant activity and also its low bioavailability because of its plasma protein binding (Lee, E., Pavy, M., Young, N., Freeman, C., y Lobigs, M.

(2006) Antiviral effect of the heparan sulfate mimetic, PI-88, against dengue and encephalitic flaviviruses. *Antiviral Res.* 69:31-38).

The second antiviral approach has significantly progressed over recent years thanks to resolution of crystallographic structures of Dengue virus E protein before (Modis, Y., Ogata, S., Clements, D., y Harrison, S. C. (2003) A ligand-binding pocket in the dengue virus envelope glycoprotein. *Proc. Natl Acad. Sci U.S.A.* 100: 6986-6991. Zhang, Y., Zhang, W., Ogata, S., Clements, D., Strauss, J. H., Baker, T. S., Kuhn, R. J., y Rossmann, M. G. (2004) Conformational changes of the flavivirus E glycoprotein. *Structure.* 12: 1607-1618) and after occurring membrane fusion (Modis, Y., Ogata, S., Clements, D., y Harrison, S. C. (2004) Structure of the dengue virus envelope protein after membrane fusion. *Nature.* 427: 313-319).

The structural information available from other flavivirus has also contributed positively to the development of fusion inhibitors. (Rey, F. A., Heinz, F. X., Mandl, C., Kunz, C., y Harrison, S. C. (1995) The envelope glycoprotein from tick-borne encephalitis virus at 2 A resolution. *Nature.* 375: 291-298. Bressanelli, S., Stiasny, K., Allison, S. L., Stura, E. A., Duquerroy, S., Lescar, J., Heinz, F. X., y Rey, F. A. (2004) Structure of a flavivirus envelope glycoprotein in its low-pH-induced membrane fusion conformation. *EMBO J.* 23:728-738).

Modis et al. determinated the structure of a soluble fragment (residues 1-394) of E protein dimmer from Dengue virus DEN2 in presence and absence of n-octyl-β-D-glucoside (BOG) detergent (Modis, Y.; Ogata, S.; Clements, D.; Harrison, S. C. (2003) A ligand-binding pocket in the dengue virus envelope glycoprotein. *Proc. Natl Acad. Sci U.S.A.* 100: 6986-6991).

The key difference between the two structures is a local rearrangement of the "kl" beta-hairpin (residues 268-280) which opens up a hydrophobic pocket that accommodates a molecule of BOG. The "kl" beta-hairpin was identified as a key structural element for initiating conformational changes that leads to formation of postfusion trimers at acidic pH.

Structural changes detected in prefusion E protein confirmed previous observations made by Rey et al. (Rey, F. A.; Heinz, F. X.; Mandl, C.; Kunz, C.; Harrison, S. C. (1995) The envelope glycoprotein from tick-borne encephalitis virus at 2 A resolution. *Nature.* 375: 291-298) who proposed for first-time that the base of domain II has hinge-like characteristics and a hinge motion about this region would elevate the tip of domain II above the viral membrane and bring fusion peptide into prominence.

Their hypothesis was based on the analysis of the crystallographic structure of a soluble fragment of E protein from Tick Borne Encephalitis virus and the existence of mutations in domain I-II interface affecting virulence and threshold pH fusion in several flavivirus. The structure of E protein dimer in complex with BOG revelead that these mutations mainly correspond to residues whose side chains line in the hydrophobic pocket (Modis, Y.; Ogata, S.; Clements, D.; Harrison, S. C. (2003) A ligand-binding pocket in the dengue virus envelope glycoprotein. *Proc. Natl Acad. Sci U.S.A.* 100: 6986-6991).

Modis et al. propose the "kl" beta-hairpin, the "kl" beta-hairpin associated hydrophobic pocket comprising residues from domain I-II interface (residues 47-54, 128-137 and 187-207) and the hydrophobic core beneath the "kl" beta-hairpin as druggable regions for developing therapeutic candidates against a disease caused by Dengue virus and other viruses having a class II protein (Patent Application: Children's Medical Center Corporation Modis Y, Harrison S, Arnold B, WO/2005/002501, 2003).

The site occupied by BOG molecule at the domain I-II interface was recently used as a target for design inhibitors of membrane fusion process using virtual screening (Yang, J. M., Chen, Y. F., Tu, Y. Y., Yen, K. R., y Yang, Y. L. (2007) Combinatorial computational approaches to identify tetracycline derivatives as flavivirus inhibitors. *PLoS. ONE.* 2:428-437). As result, two tetracycline derivatives compounds with inhibitory effect on Dengue virus propagation were identified ($IC_{50}$ equal to 67.1 μM and 55.6 μM, respectively).

Chinea et al. described another zone of protein E dimers that might be used to inhibit infection caused by flavivirus (Aplicación de patente: Centro de Ingeniería Genética y Biotecnología, WO/2007/059715, 2005). Chinea et al. identified a topographic epitope exposed on E protein surface and on mature virions surface; which is highly conserved among all Dengue virus serotypes according to an in silico analysis of sequence conservation of E protein. The epitope is composed of 25 residues and is located in the extreme of domain II.

Chinea et al. designed neutralizaing molecules using single chain antibody variable fragments that recognize the conserved epitope. Such molecules are capable of binding two, three or multiple symmetric copies of this epitope on the surface of mature virions. They showed a higher avidity and neutralizing capacity in several orders of magnitude comparing to those of natural antibodies that recognizes the conserved epitope. Besides, these neutralizaing molecules inhibit all the four serotyopes of Dengue virus and other flavivirus.

Interestingly, the antiviral activity of these molecules does not dependent on the bivalence but binding of these molecules to the conserved epitope which interferes with E protein biological function. Therefore, the epitope located at the extreme of the domain II may be used for design small molecule inhibitors of the fusion process.

The resolution of the soluble ectodomain of E protein in its trimeric, postfusion state by Modis et al. revelead striking differences from the dimeric, prefusion form (Rey, F. A., Heinz, F. X., Mandl, C., Kunz, C., y Harrison, S. C. (1995) The envelope glycoprotein from tick-borne encephalitis virus at 2 A resolution. *Nature.* 375: 291-298). The monomers in the dimeric E protein are arranged horizontally and antiparallel whereas in the trimer they are oriented vertically, and each subunit is parallel to its neighbor.

In trimeric E protein, the entire ectodomain of the E protein folds back on itself, directing C-terminal towards the fusion loop due to rearrangements in the relative orientations of domains I and II.

It was confirmed that during trimer formation occurs conformational changes in the domain I-II interface that allows the rotation of domain II (approximately 30°) with respect to domain I. This is consistent with previous observations made by other researchers (Bressaneffi, S., Stiasny, K., Allison, S. L., Stura, E. A., Duquerroy, S., Lescar, J., Heinz, F. X., y Rey, F. A. (2004) Structure of a flavivirus envelope glycoprotein in its low-pH-induced membrane fusion conformation. *EMBO J.* 23: 728-738. Zhang, Y., Zhang, W, Ogata, S., Clements, D., Strauss, J. H., Baker, T. S., Kuhn, R. J., y Rossmann, M. G. (2004) Conformational changes of the flavivirus E glycoprotein. *Structure.* 12: 1607-1618) although "kl" beta-harpin does not adopt the open conformation seen in dimeric E protein in complex with BOG ligand.

Domain III undergoes the most significant displacement in the dimer-to-trimer transition. It rotates by about 70°, and it is placed (residue 395) 39 Å closer to the fusion peptide.

The fusion peptides of the three subunits are fully exposed on the molecular surface and they come together to form a membrane-insertable aromatic anchor at the tip of E protein trimer. This aromatic anchor is formed by three hydrophobic residues (Trp-101, Leu-107 y Phe-108) conserved among all flaviviruses.

Modiy et al. propose that the fusion loop penetrate about 6 Å into the hydrocarbon layer of the target membrane and its insertion might impose distortions in the target-cell membrane.

The fusion peptide appears to retain essentially the same conformation, whether buried against another subunit, inserted into a lipid membrane, or exposed to aqueous solvent during reversibly dissociation of E protein dimers (Rey, F. A., Heinz, F. X., Mandl, C., Kunz, C., y Harrison, S. C. (1995) The envelope glycoprotein from tick-borne encephalitis virus at 2 A resolution. *Nature.* 375: 291-298).

The contact areas between monomers in the E protein trimer include residues from domain II, residues at the packing interface between domain I-III and residues located in stem region that interacts with residues from the neighboring domain II. Modis et al. propose that the stem region might occlude a channel originated at the trimer interface, which extends towards the top of domain II up to the base of domain II.

These authors proposed novel regions which may constitute pharmacological interesting sites in E protein from the analysis of the postfusion structure (Aplicación de patente: Children's Medical Center Corporation Modis Y, Harrison S, Arnold B, WO/2005/002501, 2003).

These druggable regions includes the fusion peptide, the stem region or a portion thereof, for example, residues 396-429 and 413-447; the regions in the trimer involved in the binding of residues 396-429 of the stem region; residues from domain II at the trimer interface forming the channel where the residues 396-429 of the stem region binds; the domain I-domain III linker (residues 294-301); residues forming the domain I-III interface (residues 38-40, 143-147, 294-296 y 354-365); the residues from domain II involved in trimerization and in general, all the residues involved in the conformational change of the stem region which lead to the formation of the postfusion conformation (Aplicación de patente: Children's Medical Center Corporation Modis Y, Harrison S, Arnold B, WO/2005/002501, 2003).

In this regard, peptide inhibitors were designed based on the sequence of the stem region those who appears to interfere interactions between stem region and region comprised by residues 1-395 in the trimeric conformation of E protein. These peptides act against all the four serotypes of Dengue virus and West Nile virus and showed no toxicity in vitro (Hrobowski, Y. M., Garry, R. F., y Michael, S. F. (2005) Peptide inhibitors of dengue virus and West Nile virus infectivity. *J. Virol* 2: 49-59).

Modis et al. also proposed a possible mechanism for fusion process and different strategies to inhibit this process at various stages which includes the design of small compounds that prevent (a) the movement of the "kl" beta-harpin; (b) the interaction of the "kl" beta-harpin with the hydrophobic pocket beneath the "kl" harpin (c) the movement of residues in domain I-III interface; (d) the completion of the postfusion conformational changes by interacting with the domain II residues at the trimer interface formed by domain II of each subunit in the postfusion trimer (Aplicación de patente: Children's Medical Center Corporation Modis Y, Harrison S, Arnold B, WO/2005/002501, 2003).

GROUNDS OF THE INVENTION

Definitions

The term "flavivirus" refers to any of the following viruses: Dengue virus serotype 1 (DEN1), Dengue virus serotype 2 (DEN2), Dengue virus serotype 3 (DEN3), Dengue virus serotype 4 (DEN4), West Nile virus (WNV), St. Louis Encephalitis virus, Japanese Encephalitis virus, Yellow Fever virus, Kunjin virus, Kyasanur Forest Disease virus, Tick-borne Encephalitis virus (TBEV), Murray Valley virus, LANGAT virus, Louping disease virus and Powassan virus and Omsk hemorrhagic fever virus, including in general, all viruses with 70% identity over the entire viral genome with respect to above-mentioned viruses. The term "diseases caused by flavivirus" refers to any disease or disorder caused by the infection of a subject with a flavivirus. The term "to modulate" when used in reference to a biological function refers to the capacity of a particular chemical compound and/or experimental condition to regulate (activate/stimulate or inhibit/suppress) a particular process or biological activity. The term "to affect" when used in reference to a biological function refers to the action of to provoke an alteration or modification with negative influence over a particular biological function.

The term "Dengue virus E protein" refers to the envelope glycoprotein derived from any of the four serotypes of Dengue virus. The term "dimeric prefusion E protein" refers to the conformation adopted by the envelope glycoprotein on mature Dengue virions surface (or other flavivirus) before the occurrence of viral fusion. The term "trimeric postfusion E protein" refers to the conformation adopted by the envelope glycoprotein on mature Dengue virions surface (or other flavivirus) after the occurrence of viral fusion.

The term "domain" when used in reference to a polypeptide refers to a specific region within such polypeptide that comprises a particular structure or mediates a particular function. The term "domain II" refers to the structural motif comprising residues 52-132 and 193-280 in Dengue virus E protein serotype 2 (strain S1) and those equivalent residues to previously mentioned belonging to envelope glycoproteins from other flavivirus. The term "substructure" refers to a portion or fragment from a chemical compound.

The term "ij beta-harpin" refers to the structural motif comprised by residues $^{237}$LVTFKNPHAKKQDVVV$^{252}$ in domain II of Dengue virus E protein serotype 2 (strain S1) and those equivalent residues to the above-mentioned belonging to envelope glycoproteins from other flavivirus. The term "ij loop" refers to the structural motif comprised by the residues $^{242}$NPHAKKQ$^{248}$ in domain II of DEN2 Dengue virus E protein (strain S1) and those equivalent residues to the above-mentioned belonging to envelope glycoproteins from other flavivirus. The term "cavity associated to "ij" loop" or "groove associated to "ij" loop" or "cleft associated to "ij" loop" refers to the region of the envelope glycoprotein comprised by residues $^{68}$TTTDSRC$^{74}$, $^{97}$VDRG$^{100}$, $^{103}$NGC$^{105}$, $^{111}$GGIVT$^{115}$ and $^{245}$AKKQDV$^{250}$ in domain II of DEN2 Dengue virus E protein (strain S1) and those equivalent residues to the above-mentioned beloging to envelope glycoprotein from other flavivirus. The term "fusion peptide" refers to the structural motif comprised by residues $^{100}$GWGNGCGLF$^{105}$ in domain II of DEN2 Dengue virus E protein (strain S1) and those equivalent residues to the above-mentioned beloging to envelope glycoprotein from other flavivirus.

The term "binding or anchorage" refers to the association between two molecules due to electrostatic interactions and/ or hydrophobic interactions and/or ionic interactions and/or hydrogen-bonding interactions under physiological conditions or in silico simulated. The term "binding site" refers to a zone in a protein where can be accommodated a particular compound or ligand. This zone could be described and characterized in different ways, for example, by some or all of the amino acids shaping the region, considering all the atoms from each aminoacidic residues, or only the backbone atoms, or only the side chain atoms from each residues including or not the alpha carbons.

The term "chemical compound or ligand" refers to any agent, molecule, complex or other entity capable of binding to or interacting with a protein in a particular binding site. The term "receptor-ligand complex" refers to the association between Dengue virus (or other flavivirus) E protein with any chemical compound under physiological conditions or in silico simulated. The term "receptor" or "target" refers to a molecule, for example, the Dengue virus E protein where it is feasible to bind a particular chemical compound, and this binding or interaction might modulate the protein activity. For example, the Dengue virus E protein may be a target and the binding site can be the cleft associated to "ij" loop.

The term "anchor or structure for anchorage" refers to a chemical substructure comprising the group of atoms that guarantee the binding or the anchoring of the chemical compound to the binding site in the target molecule.

The term "to accommodate" when used in reference to a chemical compound or ligand, refers to the spacial conformation adopted by such chemical compound or ligand that geometrically fits into the binding site of the receptor.

The term "screening virtual" refers to the identification and design in silico of chemical compounds with the potential of binding and to modulate the function of a given protein target. There are two variants of virtual screening known as: receptor based virtual screening used when the receptor tridimentional structure is available (RBVS) or ligand based virtual screening (LBVS), used when the structural information of known ligands for a given target molecule is available, although it is also frequently the combination of both variants.

The term "docking" refers to the orientation of a ligand into the binding site of a protein using computational algorithms and the evaluation of the generated receptor-ligand complex.

The term "functional group" refers to submolecular structures, meaning the specific group of atoms within the molecules characterized by a specific elemental composition and connectivity, which confers reactivity to the self-contained molecule.

The term "pharmacophore" refers to the essential features (for example, steric and electronic) present in a molecule or ligand that guarantee intermolecular interactions with a given target molecule and that confer a specific biological activity to such molecule or ligand.

In modern computational chemistry, "pharmacophore model" or "pharmacophoric model" is employed to define and to cluster the essential characteristics of one or more molecules responsible for its biological activity, and they are used for the identification of new molecules or ligands sharing the identified characteristics and therefore, which are expected to have biological activity. A pharmacophore model allows clustering different ligands having different chemical groups, where one or more chemical groups correspond to one or more properties defined in the pharmacophore model and where such chemical groups are located to fixed distance corresponding to each property in the pharmacophore model. A pharmacophore model may contain some of the following properties, for example, the presence of aromatic groups and/or hydrofobic groups and/or hydrogen bond acceptor groups and/or hydrogen bond donor groups and/or cations and/or anions.

The term "apolar group or non-polar group" refers to a chemical group in which the electronic charge density is essentially uniform which does not allow its interaction with other chemical groups by hydrogen bond interaction and/or dipole-dipole interaction. The non-polar groups or apolar groups interacts each other through weak interactions of Van der Waals type. By the contrast, the term "polar group" refers to a chemical group in which the electronic distribution is not uniform that allows its participation in electrostatic interactions.

The term "alkyl" refers to an aliphatic hydrocarbon radical with a straight (i.e. unbranched) or branched chain having a defined number of carbon atoms (i.e. "alkyl $C_1$-$C_{10}$" corresponds to an alkyl which may be constituted by one to ten carbon atoms). The alkyl radical may be fully saturated, mono- or polyunsaturated and may contain di- and multivalent radicals. Examples of saturated hydrocarbon radicals included, but are not limited to, groups such as methyl, ethyl, n-propyl, isopropyl, 2,3-dimethylbutyl and others. Examples of unsaturated hydrocarbon radicals included, but are not limited to, groups such as vinyl, 2-propenyl, 2-butadienyl, 1,4-hexadienyl, 1,3-pentadienyl, ethynyl, 3-propynyl, 3-butynyl, 2,4-pentadienyl and others. Note that the term "alkyl" as used here in, include divalent aliphatic hydrocarbon radicals with a straight or branched chain. Examples of divalent alkyl radicals included, but are not limited to, $—CH_2CH_2CH_2CH_2—$; $—CH_2CH{=}CHCH_2—$; $—CH_2C{\equiv}CCH_2—$; $—CH_2CH_2CH(CH_2CH_2CH_3)CH_2—$ and others. The term "heteroalkyl" by itself or in combination with another term, refers to an aliphatic hydrocarbon radical with a straight (i.e. unbranched) or branched chain consisting of at least one carbon atom and at least one heteroatom selected from the following: O, N, P, Si and S. The heteroatoms in the heteroalkyl radical may be equal or different. The heteroatom may be placed at any interior position of the heteroalkyl group or at the position at which alkyl group is attached to the remainder of the molecule. The heteroalkyl radical may be fully saturated, mono- or polyunsaturated and can included di- and multivalent radicals. Examples of heteroalkyl radicals included, but are not limited to, —CH2-CH2-O—CH3, —CH2-CH2-NH—CH3, —CH2-S—CH2-CH3, —CH2-CH2-S(O)—CH3, —CH2-CH2-S(O)2-CH3, —CH=CH—O—CH3, —CH2-CH=N—OCH3, —CH=CH—N(CH3)-CH3, —O—CH2-CH3 and others. In the heteroalkyl radical, up to two or three heteroatoms may be consecutive placed, such as, for example, $—CH_2—NH—OCH_3$ y $—CH_2—O—Si(CH_3)_3$. Note that the term "heteroalkyl" as used here in, include divalent aliphatic hydrocarbon radicals with a straight or branched chain consisting of at least one carbon atom and at least one heteroatom. Examples of divalent heteroalkyl included, but are not limited to, $—CH_2—CH_2—S—CH_2—CH_2—$ and $—CH_2—S—CH_2—CH_2—NH—CH_2—$.

The term "heteroalkyl", as used here in, included groups such as —C(O)R'; —C(O)NR'; —NR'R"; —OR', —SR' and/or $—SO_2R'$.

In the present invention, in several times, when "heteroalkyl" is recited, it is followed by recitations of specific heteroalkyl groups, such as the above-mentioned. Note that the terms heteroalkyl and any of the following: C(O)R'; —C(O)NR'; —NR'R"; —OR', —SR' and/or $—SO_2R'$ are not redundant or mutually exclusive. Rather, the specific heteroalkyl groups, such as —NR'R" and others, are recited to add clarity.

The terms "cycloalkyl" and "heterocycloalkyl", by themselves or in combination with other terms, refers to derived alicyclic hydrocarbon radicals, having one or more fused rings or covalently linked rings, rings that may be saturated, mono or poly-unsaturated, where in the case of "cycloalkyl", the rings have only carbon and hydrogen atoms, while in the case of "heterocycloalkyl", the rings included at least one heteroatom from the following: O, N and S. Examples of monocyclic cycloalkyl included, but are not limited to, cyclopentyl, cyclohexyl, 1-cyclohexenyl, 2-cyclobutinyl, 1,3-cyclohexadienyl and others. Examples of cycloalkyl composed by several rings convalently linked included, but are not limited to, cyclobutylcyclopentyl and others. Examples of cycloalkyl formed by multiple fused rings, include the polycyclic compounds having two or more carbon atoms shared for two or more rings, for example bicycle-[4,2,0]octanyl, bicycle-[3,1,1]heptanyl, bicycle-[4,4,0]decanyl and others; and bicycle compounds with only one carbon atom shared by both rings, known as spirane for example, spiro-[3,4]octanyl.

Examples of heterocycloalkyl included, but are not limited to tetrahydrofuranyl, tetrahydropyranyl, dioxanyl, piperidinyl, morpholinyl, piperazinyl, pyrrolidinyl, thiolanyl and others. Note that the terms "cycloalkyl" and "heterocycloalkyl" include divalent alicyclic hydrocarbon radicals composed by one or more rings, fused or covalently linked, where such rings may be fully saturated, mono- or polyunsaturated, where in the case of cycloalkyl, rings are composed only by carbon and hydrogen atoms while in the case of heterocycloalkyl, at least one heteroatom is present.

The term "aryl" means an aromatic, polyunsaturated, hidrocabon radical which can be a single ring (i.e. phenyl) or multiple rings (preferably from one to three rings) fused together (i.e., naftyl, antryl and others) or covalently linked (i.e. biphenyl). The term "heteroaryl" refers to an aromatic hydrocarbon radical (preferably from one to three rings) containing at least one heteroatom from the following: N, O and S (in each single ring in the case of multiple rings). Examples of "aryl" and "heteroaryl" groups included, but do not limited to, 1-naftyl, 4-biphenyl, 1-pyrrolyl, 3-pyrazolyl, 2-imidazolyl, pyrazinyl, 2-oxazolyl, 2-thiazolyl, 3-furyl, 2-thienyl, 4-pyridyl, 2-benzothiazolyl, purinyl, 5-indolyl, 6-isoquinolyl and others. The terms "aryl" and "heteroaryl" included divalent radicals derived from an aromatic hydrocarbon, hydrocarbon composed only by carbon and hydrogen atoms, in the first case, and divalent radicals derived from aromatic hydrocarbon having one or more rings of carbon and hydrogen atoms with at least one heteroatom.

The term "arylalkyl" includes those radicals in which an aryl group is attached to one or more alkyl group (e.j., benzyl, phenyl, stirene and others). The term "heteroarylalkyl" refers to those radicals formed by one or more heteroalkyl groups attached to one or more aryl groups and/or those radicals formed by one or more heteroaryl groups attached to one or more alkyl groups (e.j., 2,5-dimethylfuran) and/or those radicals formed by one or more heteroaryl groups attached to one or more heteroalkyl groups.

The term "arylcycloalkyl" refers to those radicals formed by one or more aryl groups attached to one or more cycloalkyl groups (e.j., benzyl, phenyl, cumene, stirene, vinylbencene and others). The term "heteroarylcycloalkyl" refers to those radicals formed by one or more heteroaryl groups attached to one or more cycloalkyl groups, and/or those radicals formed by one or more heterocycloalkyl attached to one or more aryl groups and/or those radicals formed by one or more heterocycloalkyl groups attached to one or more heteroaryl groups.

The term "alkylcycloalkyl" refers to those radicals formed by one or more cycloalkyl rings substituted with one or more alkyl radicals. The term "heteroalkylcycloalkyl" refers to those radicals formed by one or more heteroalkyl group attached to one or more cycloalkyl rings, and/or those radicals formed by one or more heterocycloalkyl group substituted with one or more alkyl group and/or those radicals formed by one or more heterocycloalkyl groups substituted with one or more heteroalkyl groups.

The term "oxo" refers to an oxygen atom that is double bound to for example, any of the following atoms: carbon, nitrogen, sulfur and phosphorus. The term "halogen" refers to atoms of fluorine, chlorine, bromine and iodine. The term "heteroatom" refers to any atom other than carbon or hydrogen, usually oxygen, nitrogen, sulfur, phosphorus, boron, chlorine, bromine or iodine.

The term "members" in the context of radicals derived from cyclic hydrocarbon and aromatic hydrocarbon refers to the total of atoms comprising a ring, including heteroatoms in the case of heterocycloalkyl and heteroaryl.

The term "optionally" means that the event that is described may happen or not and both events, the once that occur or not, are taken into account.

The term "constituent" refers to an atom or group of atoms which take part of the main chain (meaning, atoms or group of atoms that are not substituents) of an alkyl and/or a heteroalkyl radical, optionally substituted or not substituted. It is also referred to an atom or group of atoms that are members of a cycloalkyl radical and/or a heterocycloalkyl radical and/or aryl radical and/or heteroaryl radical optionally substituted or not substituted.

In the case of alkyl, heteroalky, aryl, heteroaryl, cycloalkyl, heterocycloalkyl are considered, substituted as well as unsubstituted forms; the substituted forms may have one or more substituents equal or different. The term "substituents" refers to an atom or group of atoms that replaces a hydrogen atom in the main chain of a hydrocarbon. The substituents included, but are not limited to, —OH; —NH2; —SH; —CN; —NO2; =O; halogen; —OR'; —OC(O)R'; —C(O)R'; —NR'R''; =NR'; =N—OR'; —C(O)NR'R''; —OC(O)NR'R''; —NR''C(O)R'; —NR'—C(O)NR'R''; —NR''C(O)OR'; —NR—C(NR'R'')=NR'''; —S(O)R', —S(O)2R'; —SR'; —S(O)2NR'R''; —NRSO2R'; —SiR'R''R'''; alkyl; heteroalkyl; cycloalkyl; heterocycloalkyl; aryl; heteroaryl; where R', R'' y R''' are independently hydrogen, substituted or unsubstituted alkyl, substituted or unsubstituted heteroalkyl, substituted or unsubstituted cylcoalkyl, substituted or unsubstituted heterocycloalkyl, substituted or unsubstituted aryl, substituted or unsubstituted heteroaryl. The term "substituted" when used in reference to a radical refers to a radical that contains one or more of the above-mentioned substituents.

The term "hydrogen bond or hydrogen-bonding interaction" refers to a bound between a functional group A-H and an atom or group of atoms B in the same or a different molecule. The functional group A-H contains a hydrogen atom electropositive and it is known as "hydrogen bond donor"; A corresponds to oxygen, nitrogen or fluorine. The atom or group B contains at least one available nondelocalized lone pair and it is known as "hydrogen bond acceptor"; B corresponds to oxygen, nitrogen or fluorine. The oxygen atom may be single or double bounded and the nitrogen may be single, double or triple bounded. A single hydrogen atom can form simultaneously two hydrogen bonds. For example, a single A-H can form simultaneous hydrogen bonds with two B atoms, which is known as "bifurcated hydrogen bonds or three center hydrogen bonds". The weak hydrogen bond donors include A-H groups, where A may be a carbon atom (C—H) or where A may be a sulfur atom (S—H). Only three types of C—H bonds are acidic enough to form hydrogen-bonding interactions and these are found in terminal alkynes (RC≡CH), chloroform (CHCl₃) and HCN. The weak H bond acceptor groups include groups B, where B is a chlorine atom or a sulfur atom.

The term "negatively charged groups" refers to an atom bearing a formal negative charge not adjacent to an atom or group of atoms with a formal positive charge.

The term "positively charged groups" refers to an atom bearing a formal positive charge not adjacent to an atom or group of atoms with a formal negative charge.

DETAILED DESCRIPTION OF THE INVENTION

Rationality of the Invention

The present invention describes the use of chemical compounds containing two distinctive functionally substructures according to the formula [C]-[A] that affect or inhibit different events of Dengue virus replication cycle related to the entry of the virus into host cells and the assembly of progeny virions. These chemical compounds bind to a patch on the surface of Dengue virus E protein, which is located in the extreme of domain II and is defined in the present invention as the groove associated to "ij" loop. The chemical compounds described in the present invention are characterized by the presence of two functionally relevant substructures, according to the following formula:

[C]-[A]

Where,

[A], is defined as anchor, and corresponds to a chemical substructure capable to binding to the groove associated to "ij" loop in E protein.

[C] is called head and it corresponds to a chemical substructure composed by 1-30 atoms, which is convalently bound to the substructure [A], [C] is preferably voluminous, having a polar or non-polar character, being net positively charged or net negatively charged, being aliphatic or aromatic, [C] favors the capacity of the chemical compounds described in the present invention to interfere or to modulate one or more intermolecular interactions involving fusion peptide, which are essentially in several stages of the virus replication cycle such as: a) the interactions during the formation of preM-E heterodimers, b) the interactions between preM-E heterodimers needed for the assembly-release of mature virions, c) the maturation process of virions due to the change of quaternary structure of preM-E heterodimers into E protein homodimers, d) the association and/or dissociation of E protein dimers characteristic of mature virions and e) the anchorage of the E protein to the infected cell endosomal membrane which triggers the fusion membrane process.

The anchor substructure described in the present invention interacts with at least three of the residues forming the groove associated to "ij" loop, which is shaped by the regions $^{68}$TTTDSRC$^{74}$, $^{97}$VDRG$^{100}$, $^{103}$NGC$^{105}$, $^{111}$GGIVT$^{115}$ and $^{245}$AKKQDV$^{250}$ of DEN2 virus E protein (strain S1) and residues from equivalent above-mentioned regions belonging to other flavivirus. Specifically, the groove associated to "ij" loop is shaped by the side-chain hydroxyl groups of Thr-68, Thr-70, Ser-72 and Thr-115 residues; the main-chain carbonyl groups of residues Asp-98, Ala-245, Lys-246, Gln-248 and Val-250, and the side-chain carbonyl groups of residues Asn-103, Gln-248 and Asp-249; the main-chain amine group of Gln-248 residue; the side-chain aliphatic groups of residues Val-97 and Ile-113, the side-chain methyl group of Thr-70 residue and the aliphatic portion of butylammonium side-chain of Lys-246 and Lys-247 residues; the guanidine group of Arg-99 residue and the ammonium group of Lys-246 and Lys-247 residues. Therefore, the cavity is lined with H bond donor and/or H bond acceptor atom groups; with negatively and positively charged atom groups and group of atoms having hydrophobic character. This heterogeneity favors the occurrence of different interactions with ligands, such as, electrostatic interactions, hydrophobic interactions, ionic interactions and hydrogen-bonding interactions.

The anchor substructure described in the present invention forms hydrogen-bonding interactions with preferably, any of the following side-chain H bond donor atoms and side-chain H bond acceptor atoms of any of the following residues: Thr-68 and/or Thr-70, Ser-72, Asn-103, Thr-115, Lys-246, Gln-248 and Asp-249; or with any of the following main-chain H bond donor atoms and H bond acceptor atoms of any of the following residues: Asp-98, Ala-245, Lys-246, Gln-248 and Val-250. On the other hand, the anchor substructure might involve hydrophobic interactions with for example, aliphatic side chains of residues Val-97, Ile-113, side-chain methyl group of Thr-70 residue and aliphatic portion of butylammonium side-chain of Lys-246 and Lys-247 residues and electrostatic interactions with side chains of residues: Asp-98, Arg-99, Asp-249, Lys-246 and Lys-247.

The head substructure described in the present invention interacts with at least one of the following residues forming the fusion peptide: Gly-100, Trp-101, Gly-102 and Phe-108. In one embodiment of the present invention, the head substructures interacts with at least one of the following residues belonging to the neighboring monomer in the mature virion dimeric E protein structure: Arg-2, Gly-5, Ile-6, Ser-7, Asn-8, His-27, Gly-28, Glu-44 and Asp-154. In another embodiment of the present invention, the head substructure interacts with at least one of the following residues from the "ij" loop: Ala-245 and His-244 or residue Asp-98 located in the cavity associated to "ij" loop.

In the present invention, the term "key residues for the anchorage to the cleft associated to "ij" loop" refers to the following residues belonging to the cavity associated to "ij" loop constituting essential interaction points with the anchor substructures described in the present invention: Thr-70, Ser-72, Val-97, Asp-98, Arg-99, Asn-103, Ile-113, Thr-115, Ala-245, Lys-246, Lys-247, Gln-248 Asp-249 and Val-250.

Description of the Binding Site

Figure 2:
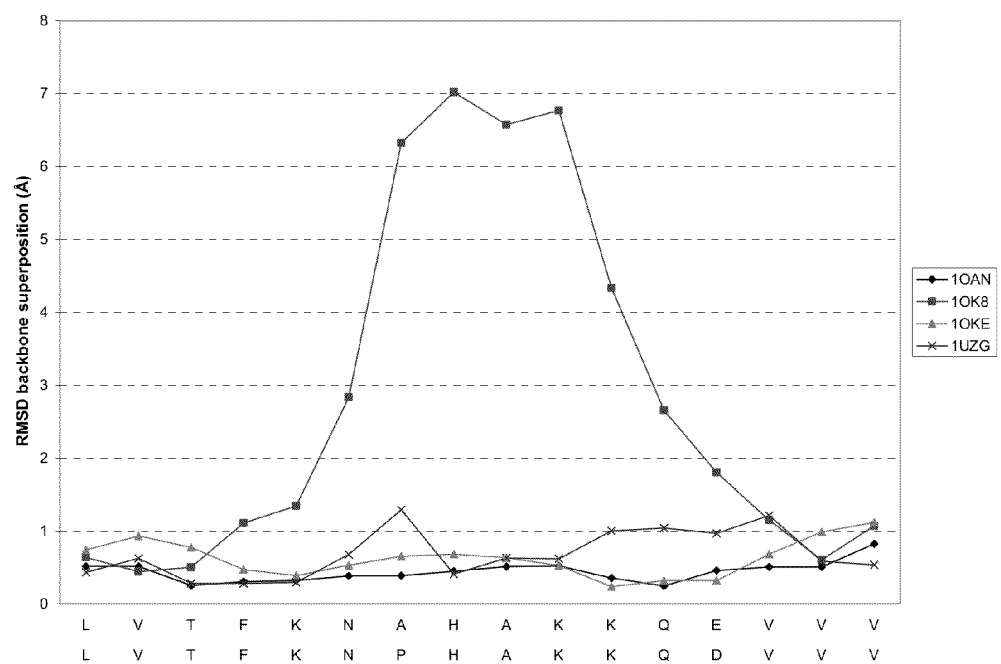
Figure 3:
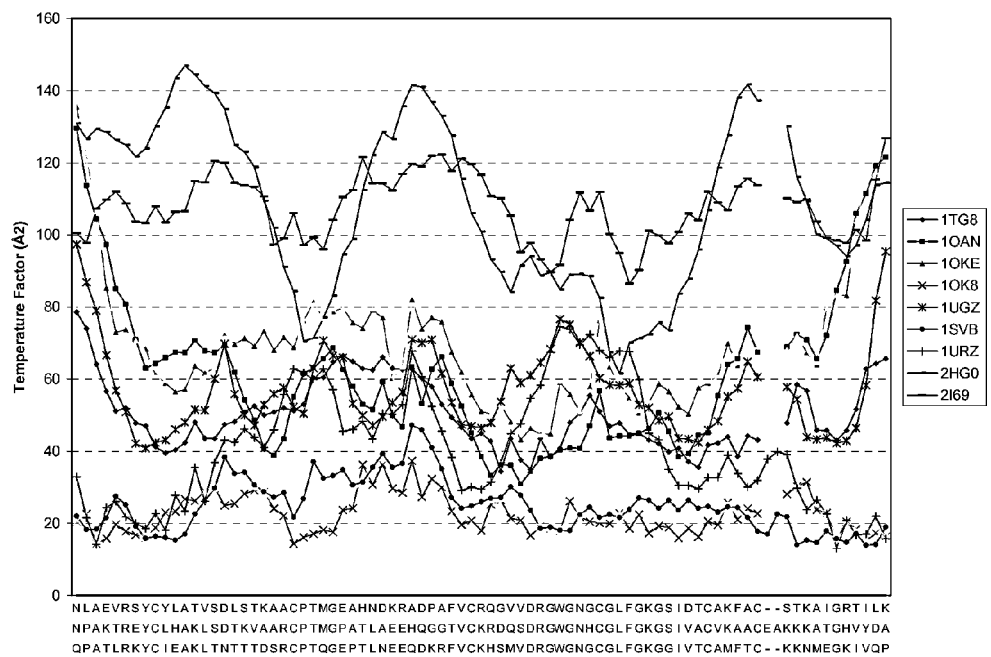
Figure 3:
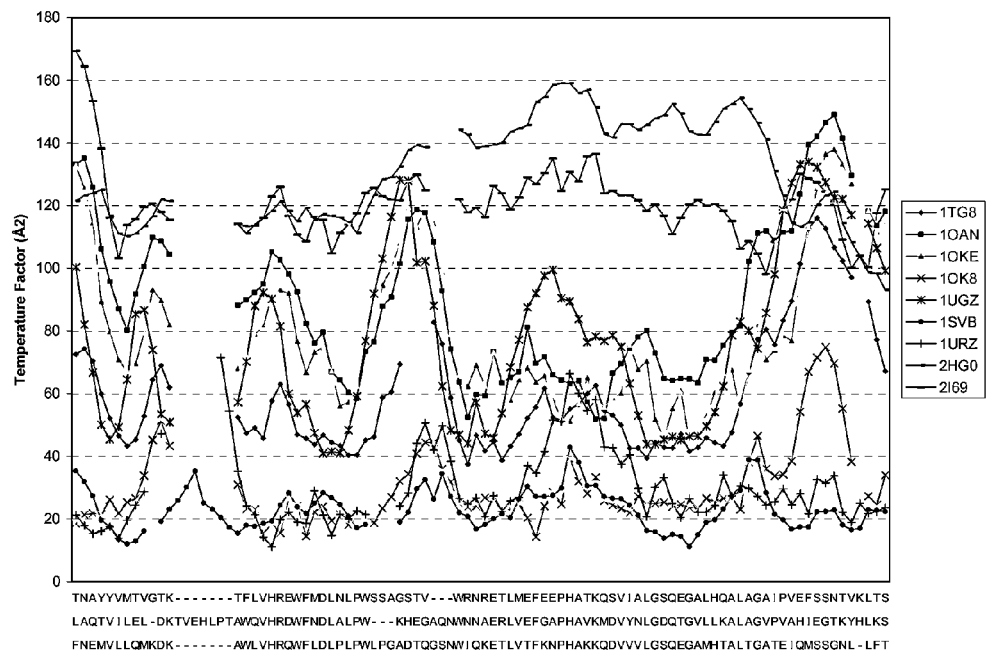

The anchor substructure contained in the compounds described in the present invention accommodates itself in the groove associated to "ij" loop of Dengue virus E protein. This groove is observed in the crystallographic structures of dimeric E protein from Dengue virus serotypes 2 and 3 (Modis, Y, Ogata, S., Clements, D., y Harrison, S. C. (2003) A ligand-binding pocket in the dengue virus envelope glycoprotein. *Proc. Natl Acad. Sci U.S.A.* 100:6986-6991. Zhang, Y., Zhang, W., Ogata, S., Clements, D., Strauss, J. H., Baker, T S., Kuhn, R. J., y Rossmann, M. G (2004) Conformational changes of the flavivirus E glycoprotein. *Structure*. 12: 1607-1618. Modis, Y, Ogata, S., Clements, D., y Harrison, S. C. (2005) Variable surface epitopes in the crystal structure of dengue virus type 3 envelope glycoprotein. *J. Virol.* 79:1223-31). In these structures, the "ij" loop adopts an open conformation shaping the above-mentioned cleft. The open conformation adopted by the "ij" beta-harpin may be stabilized by favorable interactions with residues of domain I from the neighboring monomer in the dimer. The above-described groove is elongated, narrow, little deeper and covers an area of approximately 320 Å². Nevertheless, such open conformation adopted by the "ij" loop is not observed in the crystallographic structures of the trimeric postfusion E protein from Dengue virus serotype 2 (Modis, Y, Ogata, S., Clements, D., y Harrison, S. C. (2004) Structure of the dengue virus envelope protein after membrane fusion. *Nature*. 427:313-319), the dimeric and trimeric postfusion E protein from TBEV (Rey, F A., Heinz, F. X., Mandl, C., Kunz, C., y Harrison, S. C. (1995) The envelope glycoprotein from tick-borne encephalitis virus at 2 A resolution. *Nature* 375: 291-298. Bressanelli, S., Stiasny, K., Allison, S. L., Stura, E. A., Duquerroy, S., Pescar, J., Heinz, F. X., Rey, F. A. (2004) Structure of a flavivirus envelope glycoprotein in its low-pH-induced membrane fusion conformation. *EMBO J.* 23:728-738) neither in the crystallographic structures of the monomeric E protein from WNV (FIG. 1) (Kanai, R., Kar, K., Anthony, K., Gould, L. H., Ledizet, M., Fikrig, E., Marasco, W A., Koski, R. A., y Modis, Y. (2006) Crystal structure of west nile virus envelope glycoprotein reveals viral surface epitopes. *J. Virol.* 80:11000-11008. Nybakken, G. E., Nelson, C. A., Chen, B. R., Diamond, M. S., y Fremont, D. H. (2006) Crystal structure of the West Nile virus envelope glycoprotein. *J. Virol.* 80:11467-74). In these structures, the "ij" loop adopts a closed conformation which radically changes the topography of that surface region, disappearing the cleft described in the present invention. Nevertheless, several structural evidences indicate that this is a flexible region, which may to adopt different conformations depending of the interaction in which it is involved. In the case of DEN2 virus E protein, the "ij" loop adopts an open conformation in the dimeric state and a closed conformation in the trimeric postfusion form, participating in different intermolecular interactions with residues from domain I and domain II respectively. In immature virions, the preM-E heterodimers interact between each other outlining projections on the virions surface. Each projection constitutes an asymmetric unit of the virion and it is composed by three preM-E heterodimers, in which the "ij" loop interacts with residues from the neighboring heterodimer. The three heterodimers do not adopt a C3 asymmetric orientation, so the intermolecular contacts between the heterodimers are not identical. In this manner, the "ij" loop interacts, in one case, with "ij" loop residues from the other monomer of E protein in the asymmetric unit, and in the other case, the "ij" loop interacts with residues from the fusion peptide. Therefore, the "ij" loop takes part in different intermolecular interactions, whose are relevant in different stages of the viral replication cycle, since morphogenesis or virion assembly, maturation of the envelope and fusion membrane process. The intrinsic flexibility of the "ij" loop is evident, either by the structural differences (RMS) observed in several resolved crystallographic structures of DEN2 virus E protein (dimeric and trimeric structures) and/or in the high temperature factors compared with other regions of E protein, and in particular with regions from domain II, for example in the DEN3 virus dimeric E protein structure (FIGS. 2 and 3). Therefore, the flexibility of the "ij" loop seems to be essential to be accommodated into the different structural environments and intermolecular interactions in which E protein is involved through the viral replication cycle. Therefore, a relevant novelty of the present invention is the identification of the open conformation adopted by the "ij" loop as target for the development of antivirals against Dengue virus and other flavivirus, where such molecules interfere with the interactions and/or structural changes of the "ij" loop and this interference inhibits or modulates one or more stages of the viral replication cycle.

The crystallographic E protein structures from other flavivirus, showed a closed conformation of the "ij" loop, nevertheless The temperature factor values from residues forming the "ij" loop in these structures are elevated (FIG. 3), as reflected in the WNV monomeric structure and in the TBEV dimeric structure of E protein, suggesting that the "ij" loop is a flexible zone which might experiment different conformational changes and also might adopt open conformations such as the one observed in DEN2 and DEN3 virus.

Description of Anchor Substructures

The chemical compounds described in the present invention to attenuate or inhibiting Dengue virus infection are characterized by the presence of two relevant distinctive functionally substructures, according to the following formula:

[C]-[A]

Figure 5:
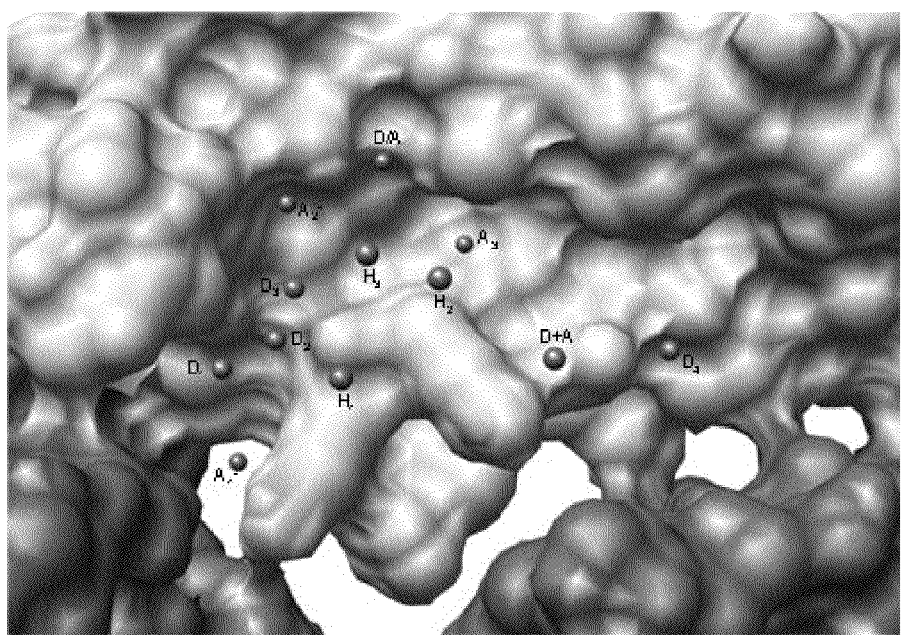

Where, the anchor [A] contains at least three of the following elements: a) an hydrogen bond donor element ($D_{1-4}$), and/or b) an hydrogen bond acceptor and/or a negatively charged group ($A_{1-2}^-$, $A_3$), and/or c) an hydrophobic element ($H_{1-3}$), and/or d) an hydrogen bond acceptor and/or hydrogen bond donor element (D/A), and/or e) a simultaneously donor-acceptor hydrogen bond element (D+A), and these elements (a)-(e) are selected among the elements constituting the 3D pharmacophoric model defined in FIG. 5. The elements of the pharmacophore model corresponds to an atom or group of atoms designed as: $D_1$, $D_2$, $D_3$, $D_4$, $A_1^-$ $A_2^-$, $A_3$, D/A, $H_1$, $H_2$, $H_3$ and D+A, where such elements are preferably separated by an interatomic distance defined in the distance matrix (I). In certain embodiments of the present invention, there are allowed deviations of the interatomic distance of about ±1 Å respect to indicated value in the interatomic distance matrix (I). In another embodiment of the present invention, there are admitted interatomic distance deviations of about ±2 Å respect to the indicated value in the interatomic distance matrix (I).

The elements of the pharmacophore model $D_1$, $D_2$, $D_3$, $D_4$, $A_1^-$, $A_2^-$, $A_3$, D/A, $H_1$, $H_2$, $H_3$ and D+A describes potential interactions between the anchor substructure [A] of the present invention and residues from the cleft associated to "ij" loop including hydrogen-bonding interactions, hydrophobic interactions and electrostatics interactions.

The $D_1$, $D_2$, $D_3$ and $D_4$ elements correspond each one to an hydrogen bond donor atom or H bond donor group of atoms.

The $A_1^-$ and $A_2^-$ elements correspond each one to an hydrogen bond acceptor atom or hydrogen bond acceptor group of atoms and/or net (or partially) negatively charged.

The element $A_3$ corresponds with an hydrogen bond donor atom or hydrogen bond donor group of atoms.

The D/A element may correspond with an atom or group of hydrogen bond acceptor atoms (in this case, it is identified herein as "D/A in acceptor condition") or the D/A element may correspond with an atom or group of hydrogen bond donor atoms (in this case, it is identified herein as "D/A in donor condition") or the D/A element may correspond to an atom or group of atoms simultaneously donor-acceptor hydrogen bond (in this case, it is identified herein as "D/A in acceptor-donor condition").

The D+A element corresponds with an atom or group of atoms simultaneously donor-acceptor hydrogen bond.

The $H_1$, $H_2$, $H_3$ elements correspond to a non-polar atom or non-polar group of atoms.

(I) Interatomic distances matrix (in Å) for the elements contained in the pharmacophore model defined in FIG. 5.

| Distance (Å) | $D_1$ | $A_2^-$ | $D_2$ | $D_4$ | D/A | D+A | $H_1$ | $H_2$ | $D_3$ | $A_1^-$ | $A_3$ | $H_3$ |
|---|---|---|---|---|---|---|---|---|---|---|---|---|
| $D_1$ | 0 | 7.0 | 2.9 | 17.4 | 12.9 | 10.2 | 5.1 | 9.3 | 4.2 | 3.9 | 10.6 | 7.2 |
| $A_2^-$ | 7.0 | 0 | 6.0 | 16.0 | 4.0 | 11.8 | 7.1 | 6.6 | 3.4 | 10.0 | 7.3 | 3.9 |
| $D_2$ | 2.9 | 6.0 | 0 | 15.5 | 8.6 | 11.6 | 5.0 | 8.0 | 3.0 | 5.8 | 8.4 | 5.2 |
| $D_4$ | 17.4 | 16.0 | 15.5 | 0 | 13.4 | 5.2 | 13.0 | 9.7 | 14.8 | 17.3 | 9.0 | 12.4 |
| D/A | 12.9 | 4.0 | 8.6 | 13.4 | 0 | 10.0 | 8.6 | 5.2 | 6.0 | 12.8 | 4.9 | 3.8 |
| D+A | 10.2 | 11.8 | 11.6 | 5.2 | 10.0 | 0 | 8.1 | 5.3 | 10.5 | 12.7 | 6.5 | 8.6 |
| $H_1$ | 5.1 | 7.1 | 5.0 | 13.0 | 8.6 | 8.1 | 0 | 5.3 | 4.4 | 5.1 | 7.7 | 5.5 |
| $H_2$ | 9.3 | 6.6 | 8.0 | 9.7 | 5.2 | 5.3 | 5.3 | 0 | 6.0 | 10.4 | 3.7 | 3.9 |
| $D_3$ | 4.2 | 3.4 | 3.0 | 14.8 | 6.0 | 10.5 | 4.4 | 6.0 | 0 | 7.1 | 7.0 | 3.2 |
| $A_1^-$ | 3.9 | 10.0 | 5.8 | 17.3 | 12.8 | 12.7 | 5.1 | 10.4 | 7.1 | 0 | 12.4 | 9.6 |
| $A_3$ | 10.6 | 7.3 | 8.4 | 9.0 | 4.9 | 6.5 | 7.7 | 3.7 | 7.0 | 12.4 | 0 | 3.9 |
| $H_3$ | 7.2 | 3.9 | 5.2 | 12.4 | 3.8 | 8.6 | 5.5 | 3.9 | 3.2 | 9.6 | 3.9 | 0 |

In the present invention, the elements $D_1$, $D_2$, $D_3$, $D_4$ and D/A (in this case, corresponds to "D/A in donor condition") of the anchor substructure [A] corresponds to an atom or group of atoms hydrogen bond donor selected independently from any of the following groups: —OH, —NH, —NH$_2$, —NH$_3^+$, =NH and —SH; which may corresponds to: a) substituents of any of the following radicals: alkyl and/or aryl and/or cycloalkyl and/or arylalkyl and/or arylcycloalkyl and/or alkylcycloalkyl, b) constituents and/or substituents of any of the following radicals: heteroalkyl and/or heteroaryl and/or heterocycloalkyl and/or heteroarylalkyl and/or heteroarylcycloalkyl and/or heteroalkylcycloalkyl, c) particulary, —OH group in functional groups with formula ROH; —NH group in functional groups with formula RNH$_2$, RR'NH, R(O)NHR', R(O)NH$_2$; =NH group in functional groups with formula RC(=NH)R'; RC(=NH)H; —SH group in functional groups with formula RSH where R, R' are independently hydrogen, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, a substituted or unsubstituted heteroaryl. In one embodiment of the present invention, each element $D_1$, $D_2$, $D_3$, $D_4$ and D/A (in this case corresponds to "D/A in donor condition") of the anchor substructure corresponds independently with —C≡CH group, which may belong to: a) constituents or substituents of any of the following radicals: alkyl and/or cycloalkyl and/or heteroalkyl and/or heterocycloalkyl and/or arylalkyl and/or arylcycloalkyl and/or alkylcycloalkyl and/or heteroarylalkyl and/or heteroarylcycloalkyl and/or heteroalkylcycloalkyl, b) substituents of aryl and/or heteroaryl radicals. In another embodiment of the present invention, each element $D_1$, $D_2$, $D_3$, $D_4$ and D/A (in this case corresponds to "D/A in donor condition") of the anchor substructure [A] corresponds independently to —CH group in HCN.

In the present invention, the elements $D_1$, $D_2$, $D_3$, $D_4$ and D/A (in this case corresponds to "D/A in donor condition") in any case do not corresponds to: a) —OH group in —C(O)OH, —S(O)OH, —P(O)OH; b) —NH group in CF3-NH—S(O)$_2$—; c) —NH group in tetrazole.

In the present invention, the elements $A_1^-$, $A_2^-$, $A_3$ and D/A (in this case, corresponds to "D/A in acceptor condition") of the anchor substructure [A] corresponds to an atom or groups of hydrogen bond acceptor atoms selected independently from any of the following groups: —C=O and/or —N=O and/or —S=O and/or —P=O and/or —O—, which may correspond to: a) substituents of any of the following radicals: alkyl and/or aryl and/or cycloalkyl and/or arylalkyl and/or arylcycloalkyl and/or alkylcycloalkyl, b) constituents or substituents of any of the following radicals: heteroalkyl and/or heteroaryl and/or heterocycloalkyl and/or heteroarylalkyl and/or heteroarylcycloalkyl and/or heteroalkylcycloalkyl, c) particularly, —C=O group in functional groups with formula RC(O)X, RC(O)R', RC(O)H, RCOO$^-$, RC(O)OH, RC(O)OR', ROC(O)OR', C(O)NR'R"; —NH group in functional groups with formula RNO$_2$; RNO; —S=O group in functional groups with formula: RS(O)$_2$OH, RS(O)$_2$R', RS(O)R'; —P=O group in functional groups with formula HOPO(OR)$_2$, RP(O)(OH)$_2$, ROP(O)(OH)$_2$; —O— group in functional groups with formula: ROR', RC(O)OR', ROOR' where X equal to halogen and R, R', R" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

In one embodiment of the present invention the elements $A_1^-$ and $A_2^-$ of the anchor substructure [A] correspond to a net (or partially) negatively charged atom or net (or partially) negatively charged group of atoms, for example, oxygen atoms from the oxo and hydroxyl groups in —C(O)OH; —S(O)OH; RR'P(O)(OH); RR'OP(O)(OH); ROP(O)(OH)$_2$; RP(O)(OH)$_2$; (RO)$_2$P(O)(OH); RS(O)$_2$OH; ROS(O)$_2$OH; nitrogen atoms in trifluoromethylsulfonamide; unsubstituted nitrogen atoms in tetrazole.

In the present invention, the elements D+A and D/A (in this case corresponds to "D/A in acceptor-donor condition") of the anchor substructure [A] corresponds to an atom or group of atoms simultaneously donor-acceptor hydrogen bond element selected independently from any of the following: —OH, —CONHR, —CONH$_2$.

In the present invention, each $H_1$, $H_2$, $H_3$ element of the anchor substructure [A] correspond to a non-polar atom or non-polar group of atoms selected independently from any of the following radicals: a) alkyl or heteroalkyl $C_1$-$C_{15}$ radical having no more than seven heteroatoms, straight or branched optionally substituted or unsubstituted; b) cycloalkyl or heterocycloalkyl composed by one, two or three rings with 3-7 members and no more than three heteroatoms, fused or linked, optionally substituted or unsubstituted; c) aryl or heteroaryl radical composed by one, two or three rings, each ring with 5-7 members, fused or linked, optionally substituted or unsubstituted; d) arylalkyl radical composed by one, two or three aryl rings, where one or more substituents corresponds to alkyl $C_1$-$C_5$ straight or branched optionally substituted or unsubstituted; e) heteroarylalkyl radical compose by one, two or three aryl or heteroaryl rings, each ring having 5-7 members and no more than three heteroatoms, fused or linked, where one of the substituents corresponds to alkyl $C_1$-$C_5$ or heteroalkyl $C_1$-$C_5$ straight or branched with no more than three heteroatoms, optionally substituted or unsubstituted; f) alkylcycloalkyl radical composed by one, two or three cycloalkyl rings with 3-7 members, fused or linked where one or more substituents corresponds to alkyl $C_1$-$C_5$ straight or branched optionally substituted or unsubstituted; g) heteroalkylcycloalkyl composed by one, two or three cycloalkyl or heterocycloalkyl rings, each ring having 3-7 members and no more than three heteroatoms, fused or linked, where one or more substituents correspond to alkyl $C_1$-$C_5$ or heteroalkyl $C_1$-$C_5$ straight or branched with no more than three heteroatoms optionally substituted or unsubstituted; h) arylcycloalkyl radical composed by one, two or three aryl rings attached to one or more cycloalkyl radicals having 3-7 members, optionally substituted or unsubstituted; i) heteroarylcycloalkyl composed by one, two or three aryl or heteroaryl rings, each ring with 5-7 members and no more than three heteroatoms, attached to one or more cycloalkyl or heterocycloalkyl rings with 3-7 members and no more than three heteroatoms, optionally substituted or unsubstituted; j) radical selected among the (a)-(i) radicals, where such radical contains the $H_1$ element of the pharmacophore model and such substituents and/or constituents heteroatoms comprised the pharmacophoric elements $D_1$ and/or $D_2$ and/or $D_3$ and/or $A_1^-$; k) radical selected among the (a)-(i) radicals, where such radical contain the $H_2$ element and such substituents and/or constituents heteroatoms comprise the pharmacophoric elements $A_3$ and/or D/A and/or D+A; l) radical selected among the (a)-(i) radicals, where such radical contain the $H_3$ element and its substituents and constituents heteroatoms comprise the elements $D_3$ and/or $A_2$ and/or $A_3$ and/or D/A.

Key Interaction Sites in the Cavity Associated to "ij" Loop for Elements $D_1$, $D_2$, $D_3$ and $D_4$ of the Pharmacophore Model In one embodiment of the present invention, $D_1$ shares one or more hydrogen atoms with main-chain carbonyl oxygen atom of Asp-98 residue and/or one or more hydrogen atoms with side-chain carboxiamide oxygen of Asn-103 residue located in the cavity associated to "ij" loop.

In one embodiment of the present invention, $D_2$ shares one or more hydrogen atoms with side-chain carbonyl oxygen of Asp-98 residue and/or one or more hydrogen atoms with main-chain carbonyl oxygen of Ala-245 residue located in the cavity associated to "ij" loop and/or one or more hydrogen atoms with main-chain carbonyl oxygen of Lys-246 residue located in the cavity associated to "ij" loop.

In one embodiment of the present invention, $D_3$ shares one or more hydrogen atoms with main-chain carbonyl oxygen of Lys-246 residue located in the cavity associated to "ij" loop.

In one embodiment of the present invention, $D_4$ shares one or more hydrogen atoms with one or more side-chain carboxylate oxygen of Asp-249 residue located in the cavity associated to "ij" loop and/or one or more hydrogen atoms with main-chain carbonyl oxygen of Val-250 residue located in the cavity associated to "ij" loop.

Key Interaction Sites in the Cavity Associated to "ij" Loop for Elements $A_1^-$ and $A_2$ of the pharmacophore model In one embodiment of the present invention, $A_1^-$ accepts one or more hydrogen atoms from side-chain ammonium group of Lys-246 residue located in the cavity associated to "ij" loop and/or $A_1^-$ bearing a net (and/or partially) negatively charge which involves electrostatic interactions with the ammonium group having a positively charge located in the cavity associated to "ij" loop.

In one embodiment of the present invention, $A_2^-$ accepts one hydrogen atom from the side-chain hydroxyl of Ser-72 residue located in the cavity associated to "ij" loop and/or $A_2^-$ bearing a net (and/or partially) negative charge and involves electrostatic interactions with the guanidine group bearing a positive charge of Arg-99 residue located in the cavity associated to "ij" loop.

Key Interaction Sites in the Cavity Associated to "ij" Loop for D/A Element of the Pharmacophore Model In one embodiment of the present invention, D/A accepts hydrogen atom from side-chain hydroxyl of Ser-72 residue located in the cavity associated to "ij" loop and/or D/A accepts hydrogen atom of side-chain hydroxyl group of Thr-70 residue located in the cavity associated to "ij" loop.

In one embodiment of the present invention, D/A shares one or more hydrogen atoms with side-chain hydroxyloxygen atom of Ser-72 residue located in the cavity associated to "ij" loop and/or D/A shares one or more hydrogen atoms with the side-chain hydroxyloxygen atom of Thr-70 residue located in the cavity associated to "ij" loop.

In one embodiment of the present invention, D/A accepts the side-chain hydroxyl hydrogen atom of Ser-72 residue located in the cavity associated to "ij" loop and/or D/A shares one or more hydrogen atoms with the side-chain hydroxyl oxygen atom of Thr-70 residue located in the cavity associated to "ij" loop.

In one embodiment of the present invention, D/A shares one or more hydrogen atoms with the side-chain hydroxyloxygen atom of Ser-72 residue located in the cavity associated to "ij" loop and/or D/A shares one or more hydrogen atoms with the side-chain hydroxyl hydrogen atom of Thr-70 residue located in the cavity associated to "ij" loop.

Key Interaction Sites in the Cavity Associated to "ij" Loop for $A_3$ element of the Pharmacophore Model In one embodiment of the present invention, $A_3$ accepts hydrogen atom from side-chain hydroxyl group of Thr-115 residue located in the cavity associated to the "ij" loop and/or one hydrogen atom from main-chain amine group of Gln-248 located in the cavity associated to "ij" loop.

Key Interaction Sites in the Cavity Associated to "ij" Loop for D+A Element of the Pharmacophore Model In one embodiment of the present invention, D+A accepts one or more hydrogen atoms from side-chain ammonium group of Lys-247 residue located in the cavity associated to "ij" loop and/or it shares one or more hydrogen atoms with one or both oxygen atoms from side-chain carboxylate group of Asp-249 residue located in the cavity associated to "ij" loop.

Key Interaction Sites in the Cavity Associated to "ij" Loop for $H_1$, $H_2$ and $H_3$ Elements of the Pharmacophore Model In one embodiment of the present invention, $H_1$ involves hydrophobic interactions with the aliphatic portion of butylammonium side-chain of residue Lys-246 located in the cavity associated to "ij" loop.

In one embodiment of the present invention, $H_1$ involves hydrophobic interactions with the aliphatic portion of butylammonium side-chain of Lys-246 and Lys-247 residues located in the cavity associated to "ij" loop.

In one embodiment of the present invention, $H_2$ involves hydrophobic interactions with the aliphatic portion of butylammonium side-chain of Lys-247 residue located in the cavity associated to "ij" loop.

In one embodiment of the present invention, $H_2$ involves hydrophobic interactions with the aliphatic portion of butylammonium side-chain of Lys-247 residue located in the cavity associated to "ij" loop and/or $H_2$ involves hydrophobic interactions with side-chain methyl group of Thr-70 residue located in the cavity associated to "ij" loop.

In one embodiment of the present invention, $H_3$ involves hydrophobic interactions with the side-chain of Val-97 and/or Ile-113 residues, both located in the cavity associated to "ij" loop.

Description of Head Substructures

In the present invention, the head substructure [C] or $R_c$ corresponds to any of the following:
a) hydrogen; b) alkyl $C_1$-$C_{10}$ or heteroalkyl $C_1$-$C_{10}$ with no more than three heteroatoms optionally substituted or unsubstituted; c) cycloalkyl or heterocycloalkyl radical composed by one, two or three rings; each one having 3-7 members and no more than three heteroatoms, fused or linked, optionally substituted or unsubstituted; d) aryl or heteroaryl radical composed by one, two or three rings, each one having 5-7 members and no more than three heteroatoms, optionally substituted or unsubstituted; e) arylalkyl radical composed by one, two or three aryl rings, where one or more substituents corresponds to alkyl $C_1$-$C_5$ straight or branched optionally substituted or unsubstituted; f) heteroarylalkyl radical composed by one, two or three aryl or heteroaryl rings, each one having 5-7 members and no more than three heteroatoms, fused or linked, where one of the substituents corresponds to alkyl $C_1$-$C_5$ straight or branched optionally substituted or unsubstituted or heteroalkyl $C_1$-$C_5$ straight or branched with no more than three heteroatoms, optionally substituted or unsubstituted; g) alkylcycloalkyl composed by one, two or three cycloalkyl rings, each one having 3-7 members, fused or linked, where one or more substituents corresponds to the alkyl $C_1$-$C_5$ straight or branched optionally substituted or unsubstituted groups; h) heteroalkylcycloalkyl radical composed by one, two or three cylcloalkyl or heterocycloalkyl rings, each one having 3-7 members and no more than three heteroatoms, fused or linked, where one or more substituents corresponds to alkyl $C_1$-$C_5$ straight or branched optionally substituted or unsubstituted or heteralkyl $C_1$-$C_5$ straight or branched with no more than three heteroatoms optionally substituted or unsubstituted; i) arylcycloalkyl radical composed by one, two or three aryl rings attached to one or more cycloalkyl radicals, each one having 3-7 members, optionally substituted or unsubstituted; j) heteroarylcycloalkyl radical composed by one, two or three aryl or heteroaryl rings, each one having 5-7 members and no more than three heteroatoms, attached to one or more cycloalkyl or heterocycloalkyl rings having 3-7 members and no more than three heteroatoms, optionally substituted or unsubstituted; k) the radical selected among the radicals (b)-(j), where its substituents comprise one or more positively charged groups selected from the following: $RNH_2$, RNHR', RNR'R", RC(NRR')=NR", C(NR'R")2=NR'''; RNHC(NR'R")=NR"; C(RNH)2=NR'; RC(R'NH)=NR"; l) the radical selected among radicals b)-j). where its substituents comprise one or more negative charged groups selected from the following: C(O)OH; S(O)OH; RR'P(O)(OH); RR'OP(O)(OH); ROP(O)(OH)$_2$; RP(O)(OH)$_2$; (RO)$_2$P(O)(OH); RS(O)$_2$OH; ROS(O)$_2$OH; tetrazole.

Mechanism of Inhibition

The chemical compounds described in the present invention inhibit Dengue virus infection by one or severals of the following mechanisms:
A) The affection of the morphogenesis process and/or assembly of virions,
B) The interference with the exocytic traffic and the virion maturation process,
C) The modulation of the mature virions stability,
D) The affection of membrane fusion process.

The role of the anchor substructure of the chemical compounds described in the present invention is to guarantee their anchorage into the cleft associated to "ij" loop and therefore, to allow the localization of these chemical compounds in the surrounding of the extreme of E protein domain II. This region from the domain II is involved in several intermolecular interactions that characterize this protein such as the preM-E interactions, the formation of E protein dimers in mature virions and the interactions between E protein and endosomal membrane necessary for the fusion process. Therefore, the binding of the chemical compounds, described in the present invention, to E protein interferes and/or modifies these intermolecular interactions provoking the affection of the biological function of E protein associated to each particular interaction and therefore, causing an inhibitory effect of one or more stages of the virus replication cycle related with the affected biological function.

This is the case of the morphogenesis and/or the virion assembly process, one stage characterized by the virion release in the reticule endoplasmatic membrane and which is mediated by collateral interactions between the preM and E proteins. The compounds described in the present invention and the preM protein compete for the binding to the E protein interfering the release process. Besides the anchor substructure, the head substructure also favors the activity of these compounds, contributing in a major affinity and/or steric interference. The blockage of the preM-E interactions also provokes the exposure of the fusion peptide to the solvent, without the protection offered by the preM protein. Thus, the E protein become exposed to premature interactions with the intracellular membranes or with the membrane virion itself, affecting in such a way the intracellular traffic through the exocytic pathway and the virión maturation in the completed infectivity viral particles. The head substructure may also contribute in this stage, then a non-polar and voluminous head increases the E protein-ligand complex affinity by the membrane and sterically interferes with the formation of E protein homodimers, characteristic for the envelope of mature virions. The election of the proper head substructure is also essential to modulate the stability of mature virions. One possibility is the destabilization of E protein homodimers by steric interference and/or by unfavorable atomic interactions between the head substructure and atoms from the neighboring monomer. As a result, these virions are more unstables and prone to an early inactivation in the extracellular and intracellular environment. It is also possible the design of anchor substructures that guarantee favorable interactions with residues from the neighboring monomer, contributing to an additional stabilization of homodimers. In this case, the biological effect also conduces to the attenuation of the virion infectivity, interfering with changes of the quaternary structures associated to the fusion membrane process which occurs in endosomal vesicles during entry of virus into host cells. An increase in the dimer stability causes the decrease of the fusion pH threshold; while the increase of dimer instability elevates the fusion pH threshold value, in both cases the fusion process is affected. The anchor substructure described in the present invention may also alter the hydrophatic properties of the fusion peptide, modifying its capacity of interaction with the endosomal membrane. In such a way, a non-polar head substructure provokes an increase in the binding affinity to membrane while a polar head substructure induces the contrary effect. In any case, the interaction between the head substructure with the fusion peptide affects the virus fusion with endosomal membrane.

The invention comprises the pharmaceutical compositions containing one or more chemical compounds or their pharmaceutically acceptable salts thereof, as other pharmaceutically allowed vehicles or additives containing them. Besides, the invention also includes the use of chemical compounds for manufacture of drugs for the treatment of Dengue virus and other flavivirus. The invention also includes the use of such chemical compounds or variants thereof for the prevention and/or treatment of infections in human beings caused by flavivirus, with the occurrence of at least the reduction of one symptom of the disease.

A novel aspect of the present invention which constitutes an advantage in relation to other strategies for the development of antivirals focused in the inhibition and/or interference of individual stages of virus replication cycle relies in that chemical compounds described in the present invention are designed to interfere with several stages of viral replication cycle enhancing the antiviral effect. Since these compounds are towards to a biologically relevant binding site, which is evolutively conserved in these viruses, the possibility of generating scape mutants also decrease.

Methodology for the Identification of Anchor Substructures

The chemical compounds were identified using computational methods, specifically combining the results of virtual screening by docking and the use of a pharmacophore model. A model of the dimeric prefusion E protein according to mature viron structure and a database of chemical compounds, were used. Such model was constructed superposing in an independent manner domain II and domains I+III of DEN2 virus E protein (1TG8) with equivalently domains in the structure of DEN2 mature viral particle (1THD) determinated by electronic cryomicroscopy (Cryo-EM) using Whatif software (Vriend, G (1990) WHAT IF: a molecular modeling and drug design program. *J Mol. Graph.* 8:52-56) and further energy minimization of domain I-II interface residues (Example I). The target region in the E protein used as binding site in docking simulations corresponds to the cavity associated to "ij" loop described in the present invention. The orientation and evaluation of millions of conformations of chemical compounds from ZINC database (Irwin, J. J. y Shoichet, B. K (2005) ZINC—A Free Database of Commercially Available Compounds for Virtual Screening. *J. Chem. Inf. Model.* 45:177-182) into the cavity associated to "ij" loop from the constructed E protein model was done using Dock program (Kuntz, I. D., Blaney, J. M., Oatley, S. J., Langridge, R. y Ferrin, T. E. (1982) A geometric approach to macromolecule-ligand interactions. *J Mol. Biol.* 161:269-88). Chemical compounds with the highest energy binding values were selected (for example, Energy $<=-35$ kjmol$^{-1}$ according to the evaluation done with the energy function of Dock program version 4) and their predicted binding mode in receptor was visually analyzed. Finally, a group of chemical compounds were chosen not only because of their high binding energy values (Energy $<=-35$ kjmol$^{-1}$) but also because they adopt conformations accommodated in the cavity associated to "ij" loop having interactions via hydrogen bond and/or hydrophobic interactions and/or electrostatic interactions according to in silico predictions with several residues bellow mentioned:

a) residues forming this cavity, for example: Thr-70, Ser-72, Val-97, Asp-98, Arg-99, Asn-103, Ile-113, Thr-115, Ala-245, Lys-246, Lys-247, Gln-248 and Asp-249.
b) residues forming fusion peptide: Gly-100, Trp-101, Gly-102 and Phe-108.
c) residues corresponding to neighboring monomer in the dimeric structure of mature virions: Arg-2, Gly-5, Ile-6, Ser-7, Asn-8, His-27, Gly-28, Glu-44 and Asp-154.
d) residues from "ij" loop, for example: His-244.

The analysis of in silico binding mode predictions into the cleft associated to "ij" loop of each one of chosen chemical compounds via virtual screening experiments allowed the detection of substructures with potentially favorable interactions with the key residues for the anchorage to cleft associated to "ij" loop definided in the present invention. The identified substructures allowed definition of a 3D pharamacophoric model (FIG. 5) of favorable interatomic interactions with the key residues for the anchorage to the cleft associated to "ij" loop. The construction of this pharmacophoric model was complemented with Pocket program (Chen J. y Lai L. (2006) Pocket v.2: Further Developments on Receptor-Based Pharmacophore Modeling. *J. Chem. Inf. Model.* 46: 2684-2691). Such pharmacophoric model was used in combination with 3DFS program for the identification of other anchor substructures and chemical compounds (1998) 3DFS: A New 3D Flexible Searching System for Use in Drug Design. *J. Chem. Inf. Comput. Sci.* 38: 71-77). The chemical compounds identified by virtual screening and by using the pharmacophore model are shown in Example 2. The anchor substructures described in the present invention comprises at least one of the following elements: a) an hydrogen bond donor element ($D_{1-4}$) and/or b) an hydrogen bond acceptor and/or negatively charged group ($A_1$-, $A_2$-, $A_3$), and/or c) an hydrophobic element ($H_{1-3}$), and/or d) an hydrogen bond acceptor or donor element (D/A), and/or e) a simultaneously hydrogen bond donor-acceptor element (D+A), and all these elements (a)-(e) are selected from the elements constituting the 3D pharmacophoric model described in the present invention, which are described in Example 3. The intermolecular interactions between the anchor substructures described in the present invention and the key residues for the anchorage to the groove associated to "ij" loop are illustrated in Example 4. The capacity of the chemical compounds described in the present invention for inhibiting Dengue virus infection was in vitro evaluated in plaque inhibition assay in Vero cells. as described in Example 5.

DETAILED DESCRIPTION OF FIGURES

FIG. 1. Representation of domain II structural superposition of one of the E protein monomers of the following viruses: Dengue virus, West Nile virus and Tick-borne Encephalitis virus. It is shown the cavity associated to "ij" loop at the extreme of domain II in dimeric prefusion structures of E protein Dengue virus serotype 2 having 1OKE, 1TG8 and 1OAN identifiers and Dengue virus serotype 3 with 1UZG identifier, where the "ij" loop adopts an open conformation. This open conformation of "ij" loop is not observed in monomeric structures 2HG0 and 2I69 of West Nile virus E protein neither in dimeric prefusion structure 1SV8 from Tick-borne Encephalitis virus. Representation of the secondary structure using Chimera program (Pettersen, E. F., Goddard, T. D., Huang, C. C., Couch, G. S., Greenblatt, D. M., Meng, E. C., y Ferrin, T. E. (2004) UCSF Chimera—A Visualization System for Exploratory Research and Analysis. *J. Comput. Chem.* 25:1605-1612).

FIG. 2. Structural differences between the "ij" hairpin from the dimeric prefusion E protein 1TG8, 1OAN, 1OKE of Dengue virus DEN2, the trimeric postfusion E protein 1OK8 from Dengue virus DEN2 and the trimeric postfusion E protein 1UZG from Dengue virus DEN3. The 3D structure of dimeric prefusion E protein from Dengue virus DEN2 with identifier 1TG8 was used as template for superposition.

FIG. 3. Sequence alignment of domain II from Dengue virus, West Nile virus and Tick Borne Encephalitis virus and temperature factors of residues reported in each of the following structures: Dengue virus DEN2 dimeric E protein (1TG8, 1OAN, 1OKE), Dengue virus DEN3 dimeric E protein (1UGZ), Dengue virus DEN2 trimeric postfusion E protein (1OK8), Tick Born Encephalitis trimeric postfusion E protein (1URG) and Tick-Born Encephalitis trimeric prefusion E protein (1SVB) and monomeric E protein (2HG0 y 2I69) from West Nile virus. The temperature factors of residues constituting "ij" hairpin are shaded and amino acid sequence comprising the "ij" hairpin is underlined.

Figure 4:
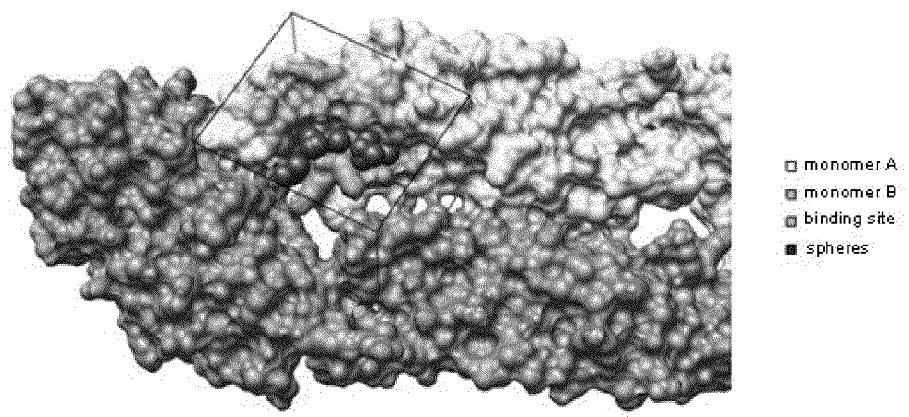

FIG. 4. Representation of the dimeric E protein model from Dengue virus serotype 2 compatible with mature virion and the binding site (cavity associated to "ij" loop) using as target for in silico virtual screening experiments. It is shown the group of spheres used to orient the ligands into the binding site and the residues of E protein considered for the intermolecular receptor-ligand energy evaluation are enclosed in a box. The Chimera software was used (Pettersen, E. F., Goddard, T. D., Huang, C. C., Couch, G. S., Greenblatt, D. M., Meng, E. C., y Ferrin, T. E. (2004) UCSF Chimera—A Visualization System for Exploratory Research and Analysis. *J. Comput. Chem.* 25:1605-1612).

FIG. 5. Schematic representation of 3D pharmacophore model in the cleft associated to "ij" loop described in the present invention.

Figure 6:
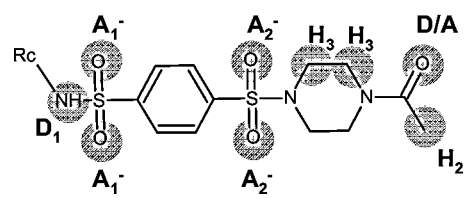
Figure 6:
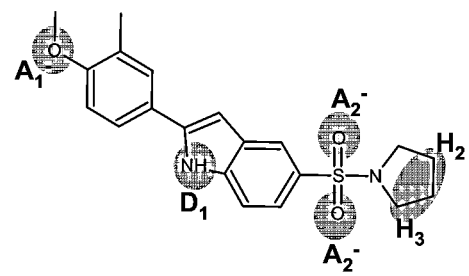
Figure 6:
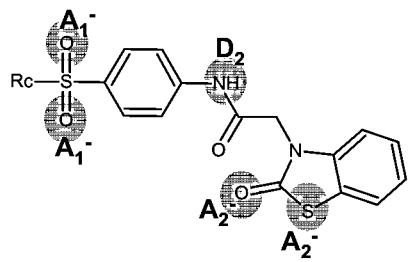

FIG. 6. Description of the elements comprising the pharmacophore model contained in the anchor substructures A-SIJ023, A-SIJ118 and A-SIJ121 and the description of the binding mode.

EXAMPLES

Example 1

Construction of the E Protein Model Compatible with Mature Virion

The selection of 3D structure of Dengue virus E protein for in silico experiments was based on the analysis of all the available crystallographic structures of such protein in Protein Data Bank, PDB (Berman, H. M., Westbrook, J., Feng, Z., Gilliland, G, Bhat, T N., Weissig, H., Shindyalov, I. N., y Bourne, V. (2000) The Protein Data Bank. *Nucleic Acids Research.* 28:235-242) resolved by X-ray crystallography and Cryo-EM. Although, the Dengue virus E protein structure resolved using cryo-EM has low resolution, it is useful because gives information about orientation between the different domains, the distance between monomers in dimer and the exposed regions of E protein on mature virion surface. With the aim to compare the E protein structure within and without mature virión, the superposition of domain II from mature virion structure obtained by cryo-EM structure (1THD) and crystallographic structures of dimeric E protein 1OAN, 1OKE and 1TG8, was done. The structural superposition was done with WhatIF program using motif command which superposes structural fragments of a certain length from one protein into the other protein (template) searching for the maximum number of equivalently amino acids between both structures with the lower root mean square deviation (RMSD) value. The structural superposition showed that structure of domain II and the groove associated to "ij" loop are conserved among all the analyzed structures (1OAN, 1OKE, 1TG8) having an RMSD values for alpha carbons lower than 0.7 Å; nevertheless, structural differences are observed between dimers obtained by X-ray crystallography and by cryo-EM. X-ray crystallographic dimers are more compact having shorter separation between monomers comparing to E dimers on the mature virion surface obtained by cryo-EM experiment. Therefore, it was determined not to use any of the available structures of Dengue virus E protein as receptor from PDB database for in silico docking simulations. Instead, an atomic model of Dengue virus E protein compatible with the pseudo-atomic structure of Dengue virus E protein on mature virion was used. This model was constructed combining the available structural information of dimeric E protein from cryo-EM (1THD) and X-ray crystallographic (1TG8) experiments. The E protein structure 1TG8 was separated in two parts, domain II and domain I+III, which were independently superposed with corresponding domains in 1THD structure using the Whatif program. Then, an energy minimization was performed to optimize the geometry distances and angle bonds of domain I-II linker and finally, and the obtained model was checked with Whatif program using fulchk command. FIG. 4 shows the 3D model of dimeric E protein compatible with mature virion used in the present invention and it is also shown, the target region used as binding site (corresponding to cavity associated to "ij" loop described in the present invention) in virtual screening experiments and to obtain additional information for the 3D pharmacophore model construction.

Example 2

Virtual Screening of a Chemical Compound Library by Molecular Docking Simulations. Construction and Use of a 3D Pharmacophore Model Virtual screening methodology was used for the in silico identification of chemical compounds having potential favorable interactions with residues of the cavity associated to "ij" loop in DEN2 virus E protein. Docking simulation consisted in orientation and energy evaluation of different conformations of chemical compounds from ZINC database (version 5) into the cavity associated to "ij" loop in DEN2 virus E protein using Dock program (versions 4.01 and 6.1). The receptor coordinates are obtained from the atomic model of dimeric DEN2 virus E protein matched into mature virion structure as described in the Example 1. The binding site corresponds to the groove associated to "ij" loop formed by residues: $^{68}$TTTDSRC$^{74}$, $^{97}$VDRG$^{100}$, $^{103}$NGC$^{105}$, $^{111}$GGIVT$^{115}$ and $^{245}$AKKQDV$^{250}$ of the atomic model of DEN2 virus E protein (strain S1) described in the Example 1. The orientation of the chemical compounds in the cavity associated to "ij" loop is fixed by a group of spheres; spheres used in the cavity associated to "ij" loop are shown in the FIG. 4.

The energetic contribution of any residue of the receptor located at a maximum distance of 5 Å from the group of spheres above-mentioned was considered in the energetic evaluation of receptor-ligand complexes interaction. The receptor energetic evaluation was done previously to docking simulation with the Grid program (an accessory tool of Dock program). The ligand was considered as a flexible molecule developing two different strategies: first, the generation of several conformations of each chemical compound from ZINC database using CORINA and Rotate programs (Sadowski, J. (1997) A hybrid approach for addressing ring flexibility in 3D database searching. *J Comput Aided Mol. Des.* 11:53-60) and second, using the flexible option of Dock program (versions 4.01 and 6.1). In the first case, the conformations obtained for each compound were oriented in the atomic model of E protein compatible with the mature virion structure using the rigid variant from the Dock program (versions 4.01 and 6.01). In both cases, the binding mode of each receptor-ligand complex was evaluated using different scoring functions from Dock program (for example, chemical function, energy function and contact function) as well as other scoring functions such as, the one implemented in AutoDock program (Morris, G. M., Goodsell, D. S., Halliday, R. S., Huey, R., Hart, W. E., Belew, R. K. y Olson, A. J. (1998) Automated Docking Using a Lamarckian Genetic Algorithm and Empirical Binding Free Energy Function. *J Comput Chem.* 19: 1639-1662) and the X-Score scoring function (Wang, R.; Lai, L.; Wang, S. Further (2002) Development and Validation of Empirical Scoring Functions for Structure-Based Binding Affinity Prediction. *J. Comput. Aided Mol. Des.* 16: 11-26). Only the best conformations of each chemical compound docked into the binding site were selected (for example, Energy >=-35 kjmol$^{-1}$ in case of Dock program version 4.01). The binding mode of each of the selected conformations was visually inspected.

Finally, the visual analysis allowed to distinguish between the chemical compounds with favorable interactions from the energetic point of view, those compounds that accommodate in the cavity associated to "ij" loop and also interact with:
a) the residues forming the cavity associated to "ij" loop, for example: Thr-70, Ser-72, Val-97, Asp-98, Arg-99, Asn-103, Ile-113, Thr-115, Ala-245, Lys-246, Lys-247, Gln-248 and Asp-249.
b) the residues forming the fusion peptide: Gly-100, Trp-101, Gly-102 and Phe-108.
c) the residues from the neighboring monomer in the dimeric structure of mature virions: Arg-2, Gly-5, Ile-6, Ser-7, Asn-8, His-27, Gly-28, Glu-44 and Asp-154.
d) the residues from the "ij" loop, for example: His-244.

Selected chemical compounds by virtual screening and using a 3D pharmacophore model are shown bellow (Table 1). Such chemical compounds bind to the cavity associated to "ij" loop through the previously described atomic interactions according to the in silico predictions.

TABLE 1

2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

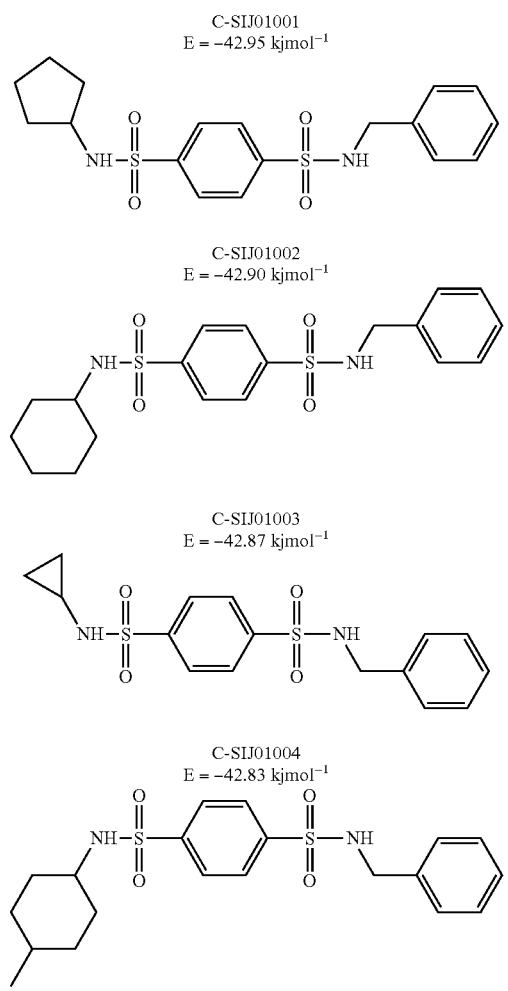

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

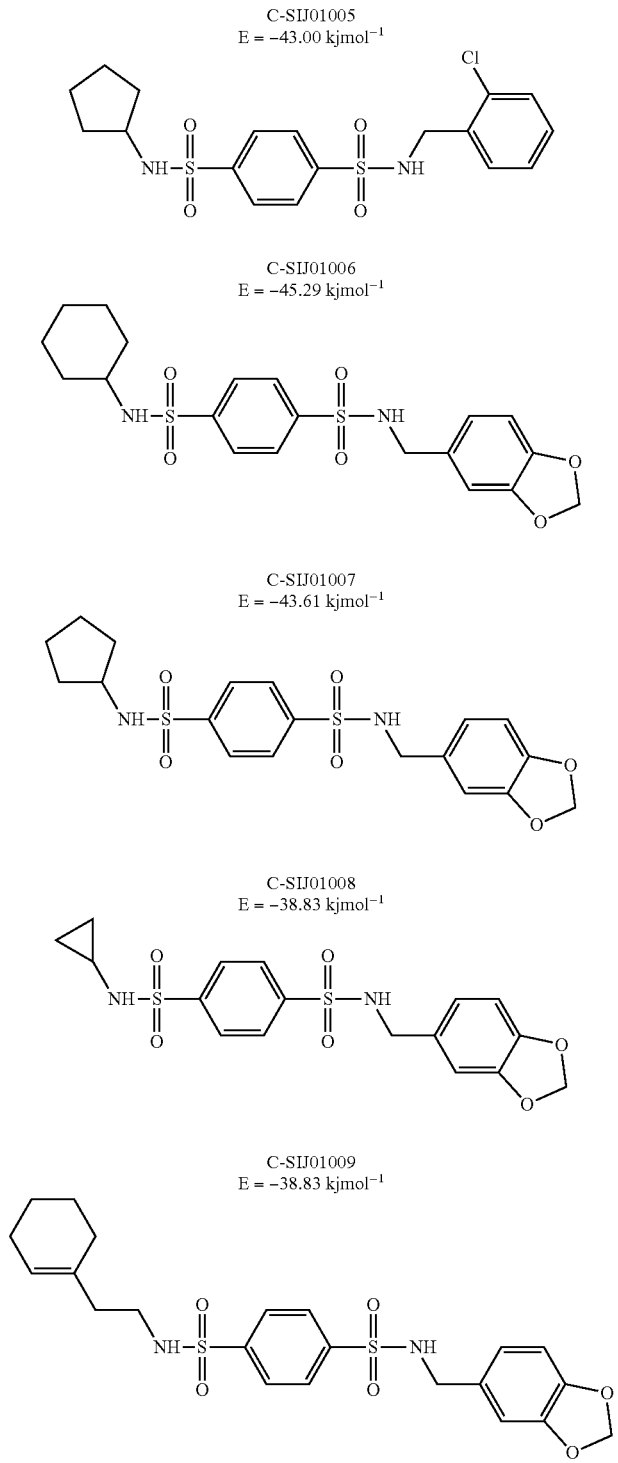

C-SIJ01005
E = −43.00 kjmol$^{-1}$

C-SIJ01006
E = −45.29 kjmol$^{-1}$

C-SIJ01007
E = −43.61 kjmol$^{-1}$

C-SIJ01008
E = −38.83 kjmol$^{-1}$

C-SIJ01009
E = −38.83 kjmol$^{-1}$

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ01010
E = −38.91 kjmol$^{-1}$

C-SIJ01011
E = −42.21 kjmol$^{-1}$

C-SIJ01012
E = −39.11 kjmol$^{-1}$

C-SIJ01013
E = −40.82 kjmol$^{-1}$

C-SIJ01014
E = −40.86 kjmol$^{-1}$

C-SIJ01015
E = −43.28 kjmol$^{-1}$

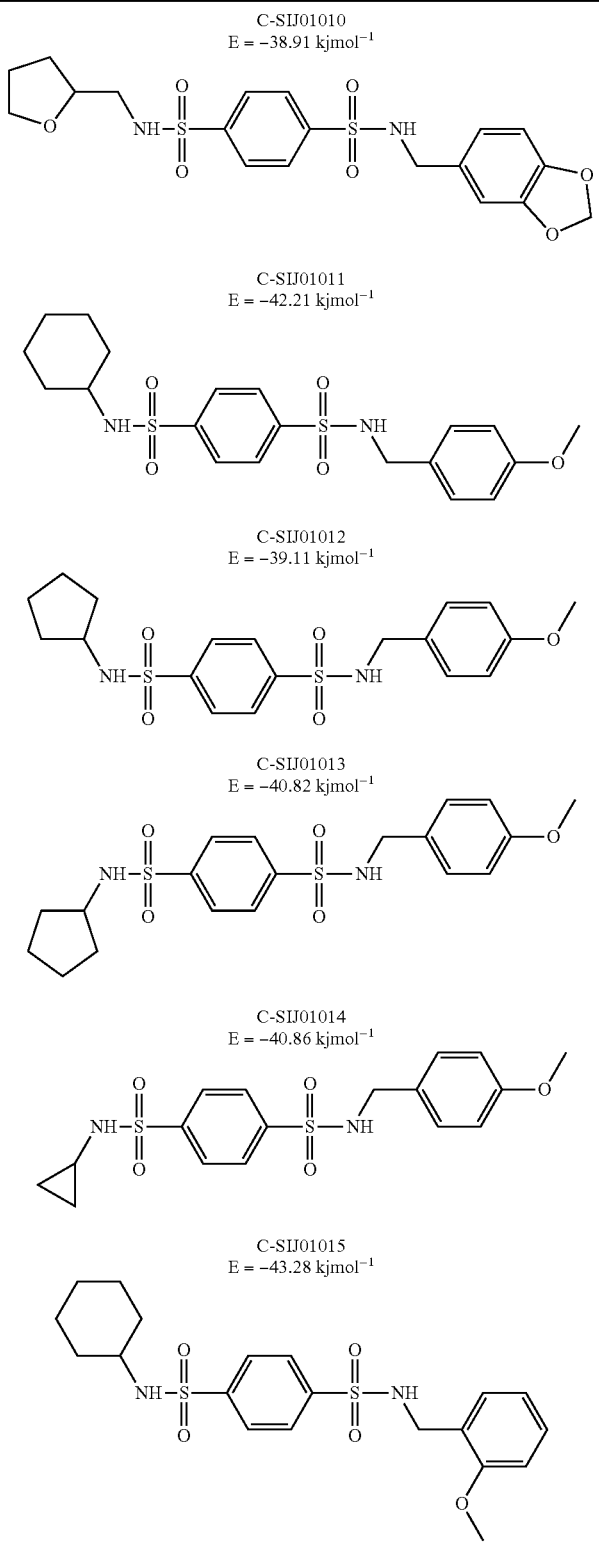

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ01016
E = −43.28 kjmol$^{-1}$

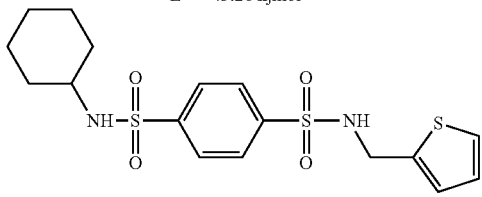

C-SIJ01017
E = −39.75 kjmol$^{-1}$

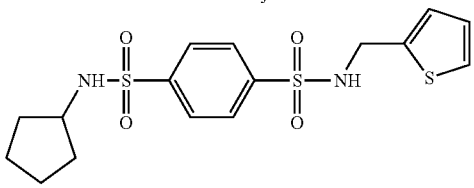

C-SIJ01018
E = −39.93 kjmol$^{-1}$

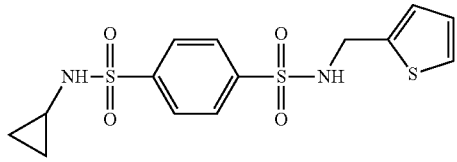 [SMILES: O=S(=O)(NCc1cccs1)c1ccc(S(=O)(=O)NC2CC2)cc1]

C-SIJ01019
E = −39.55 kjmol$^{-1}$

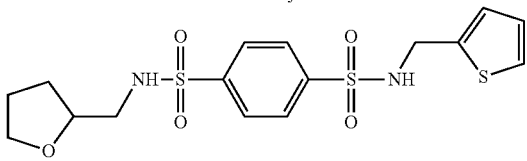

C-SIJ01020
E = −43.26 kjmol$^{-1}$

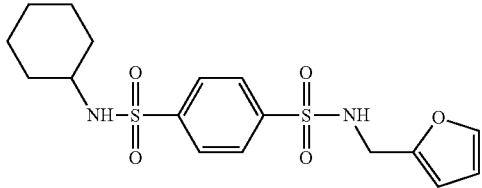 [SMILES: O=S(=O)(NCc1ccco1)c1ccc(S(=O)(=O)NC2CCCCC2)cc1]

C-SIJ01021
E = −43.32 kjmol$^{-1}$

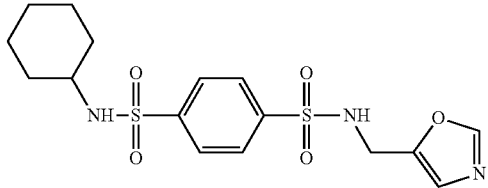 [SMILES: O=S(=O)(NCc1cnco1)c1ccc(S(=O)(=O)NC2CCCCC2)cc1]

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ01022
E = −43.37 kjmol$^{-1}$

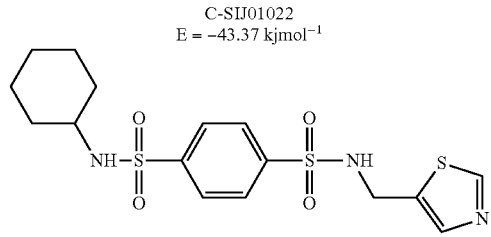

C-SIJ01023
E = −41.85 kjmol$^{-1}$

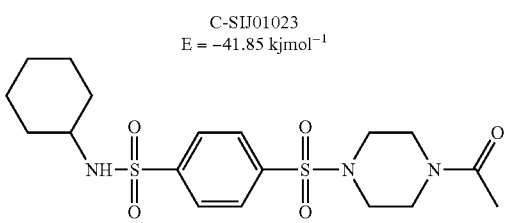

C-SIJ01024
E = −38.60 kjmol$^{-1}$

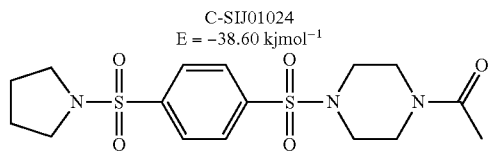

C-SIJ01025
E = −38.54 kjmol$^{-1}$

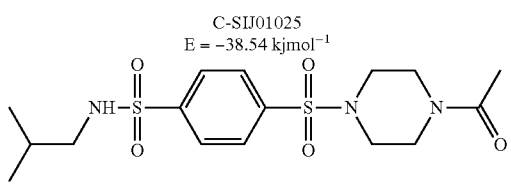

C-SIJ01026
E = −38.81 kjmol$^{-1}$

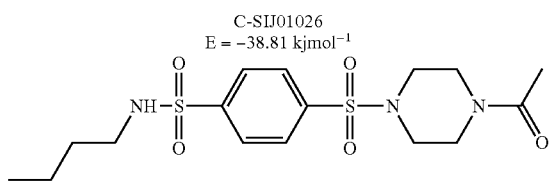

C-SIJ01027
E = −38.99 kjmol$^{-1}$

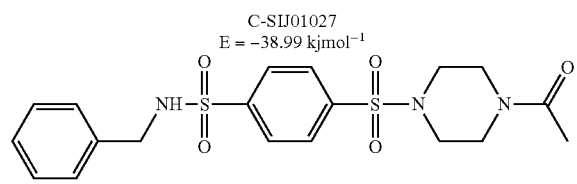

C-SIJ01028
E = −42.10 kjmol$^{-1}$

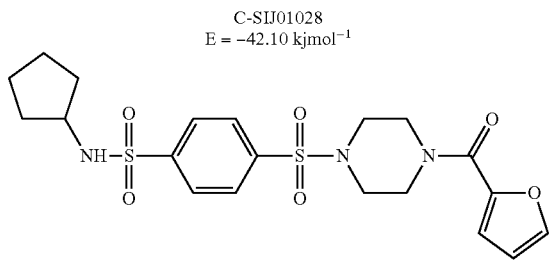

TABLE 1-continued 2D structure and energy binding value of chemical compounds with a
potential favorable binding according to energy evaluation done with scoring
functions of Dock (4.01 and 6.1 versions) and AutoDock programs and according
to the geometry and chemical composition of the atoms forming the binding site.
The reported energy values were calculated with the energy function of Dock
program 4.01.

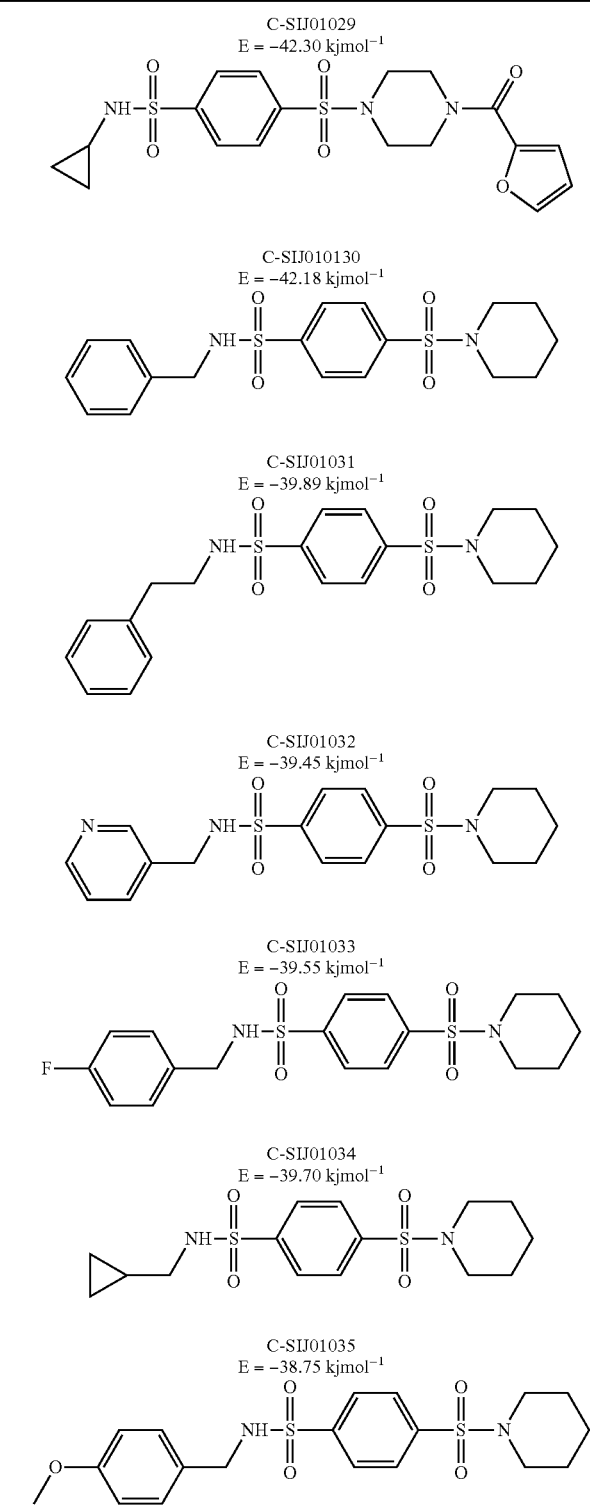

C-SIJ01029
E = −42.30 kjmol$^{-1}$

C-SIJ010130
E = −42.18 kjmol$^{-1}$

C-SIJ01031
E = −39.89 kjmol$^{-1}$

C-SIJ01032
E = −39.45 kjmol$^{-1}$

C-SIJ01033
E = −39.55 kjmol$^{-1}$

C-SIJ01034
E = −39.70 kjmol$^{-1}$

C-SIJ01035
E = −38.75 kjmol$^{-1}$

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

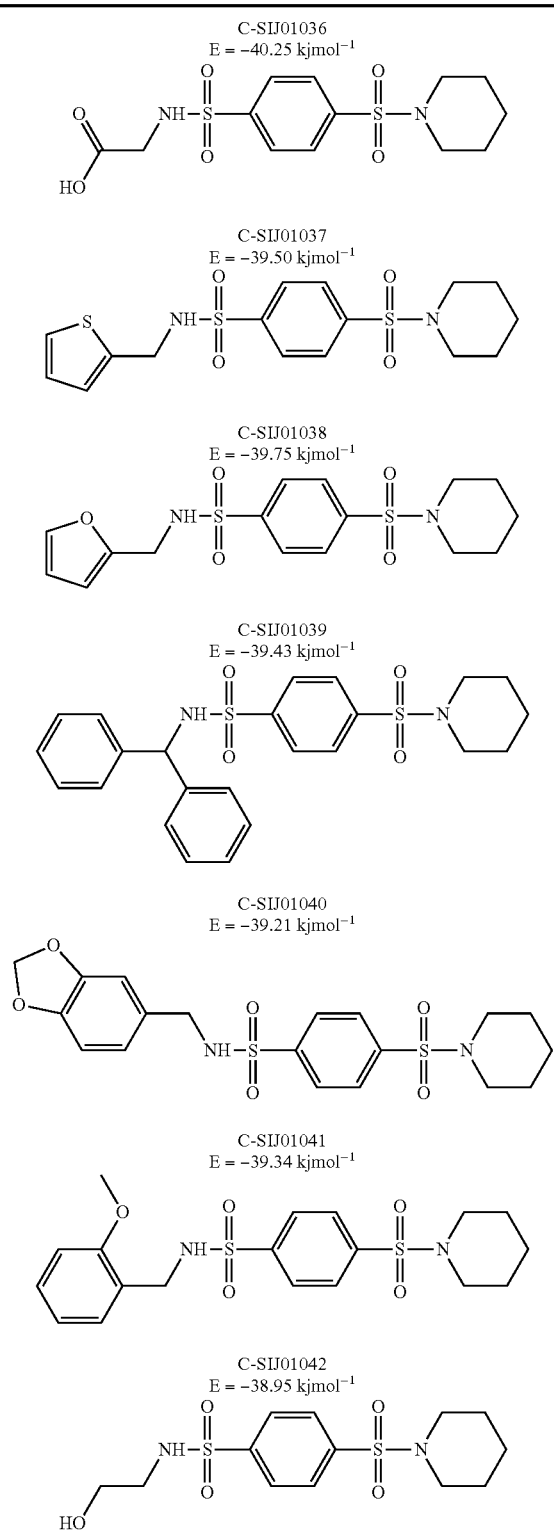

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

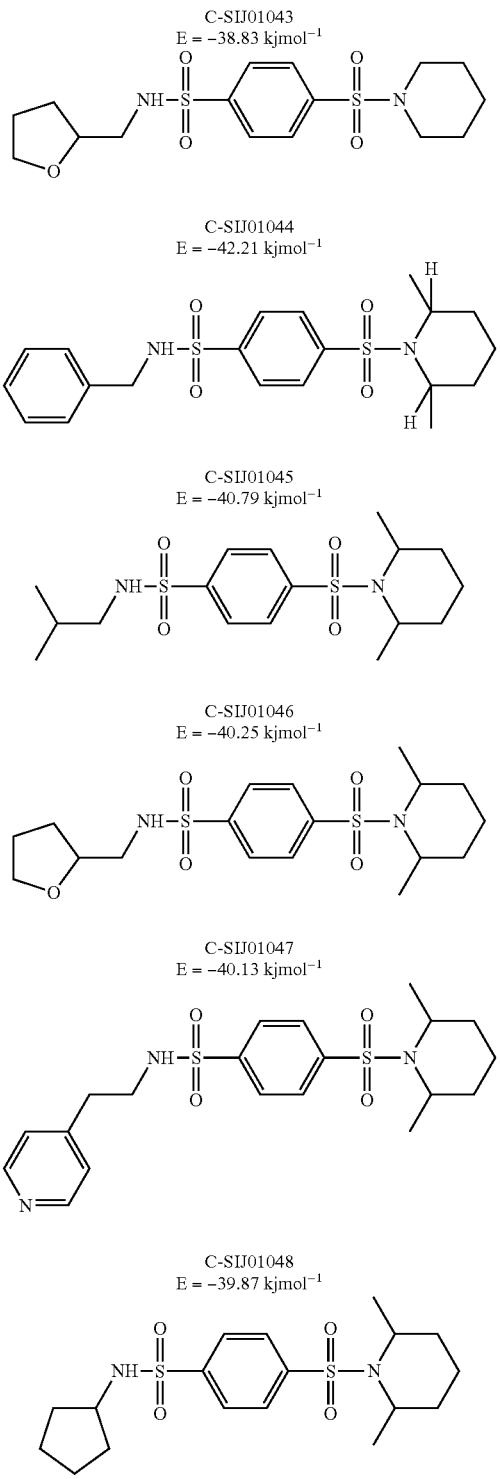

TABLE 1-continued 2D structure and energy binding value of chemical compounds with a
potential favorable binding according to energy evaluation done with scoring
functions of Dock (4.01 and 6.1 versions) and AutoDock programs and according
to the geometry and chemical composition of the atoms forming the binding site.
The reported energy values were calculated with the energy function of Dock
program 4.01.

C-S1J01049
E = −40.11 kjmol$^{-1}$

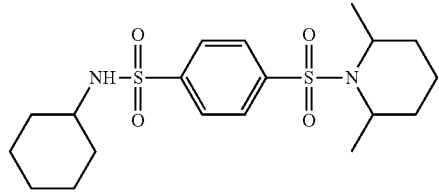 [SMILES: CC1CCCC(C)N1S(=O)(=O)c1ccc(S(=O)(=O)NC2CCCCC2)cc1]

C-SIJ01050
E = −40.02 kjmol$^{-1}$

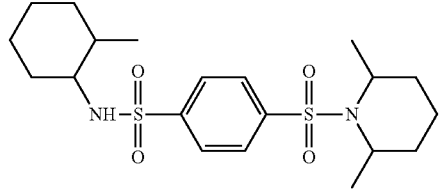 [SMILES: CC1CCCCC1NS(=O)(=O)c1ccc(S(=O)(=O)N2C(C)CCCC2C)cc1]

C-SIJ01051
E = −39.79 kjmol$^{-1}$

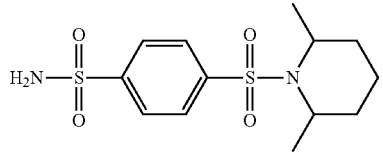 [SMILES: CC1CCCC(C)N1S(=O)(=O)c1ccc(S(N)(=O)=O)cc1]

C-SIJ01052
E = −43.63 kjmol$^{-1}$

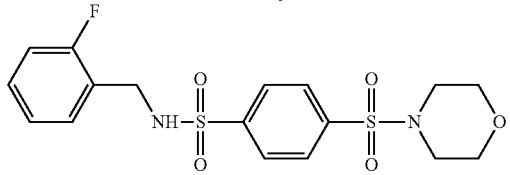

C-SIJ01053
E = −43.42 kjmol$^{-1}$

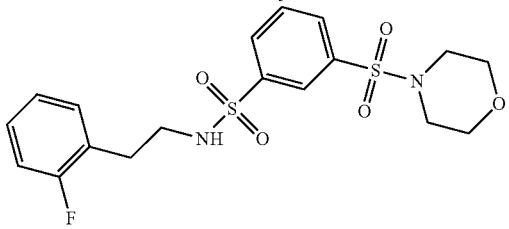

C-SIJ01054
E = −43.51 kjmol$^{-1}$

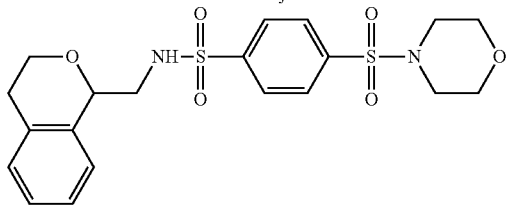

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ01055
E = −42.91 kjmol$^{-1}$

C-SIJ01056
E = −42.87 kjmol$^{-1}$

C-SIJ01057
E = −42.17 kjmol$^{-1}$

C-SIJ01058
E = −42.10 kjmol$^{-1}$

C-SIJ01059
E = −42.35 kjmol$^{-1}$

C-SIJ01060
E = −41.25 kjmol$^{-1}$

C-SIJ01061
E = −41.62 kjmol$^{-1}$

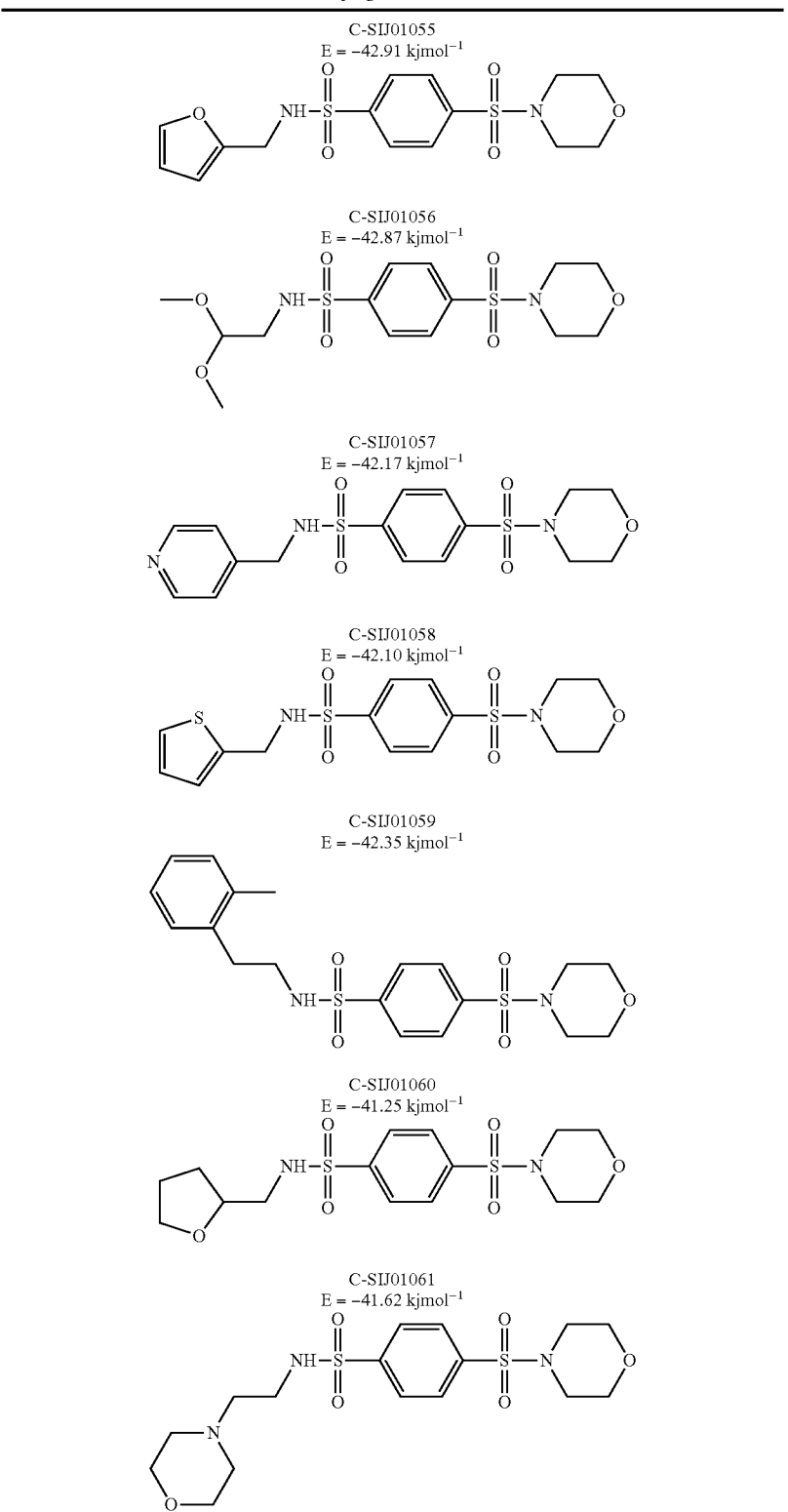

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

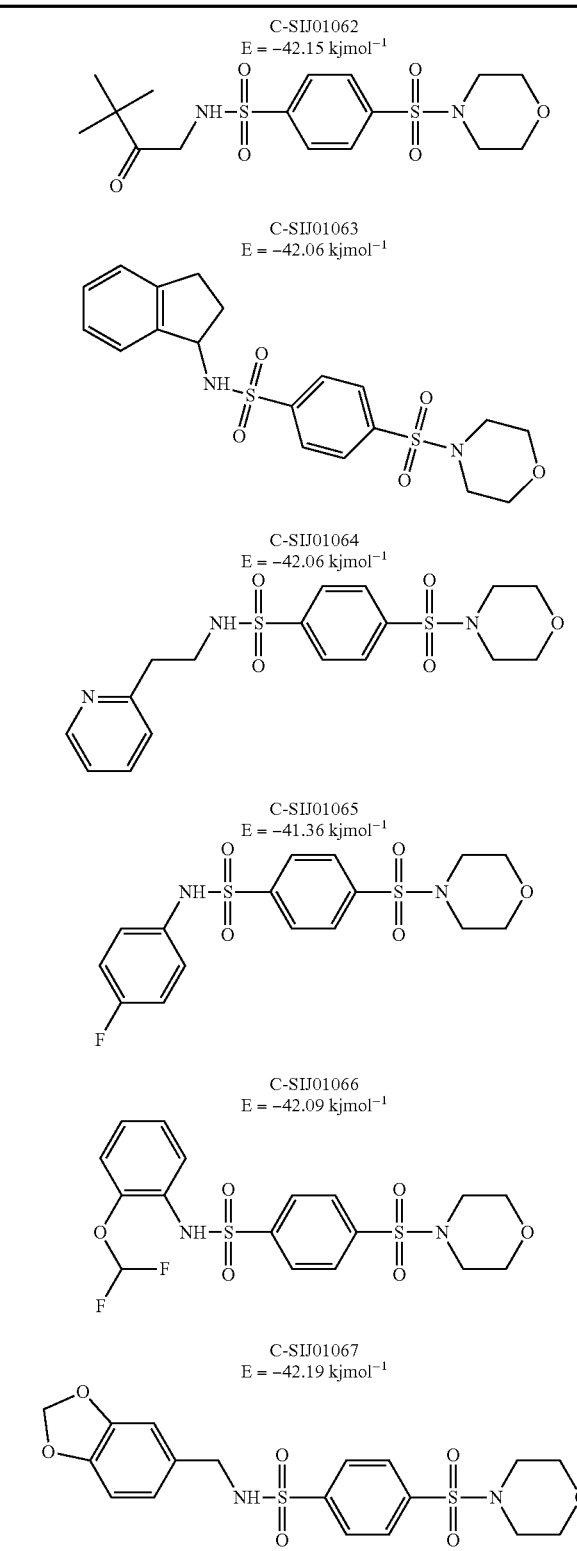

C-SIJ01062
E = −42.15 kjmol$^{-1}$

C-SIJ01063
E = −42.06 kjmol$^{-1}$

C-SIJ01064
E = −42.06 kjmol$^{-1}$

C-SIJ01065
E = −41.36 kjmol$^{-1}$

C-SIJ01066
E = −42.09 kjmol$^{-1}$

C-SIJ01067
E = −42.19 kjmol$^{-1}$

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ01068
E = −41.90 kjmol$^{-1}$

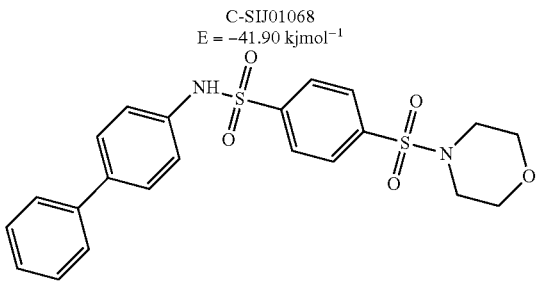

C-SIJ01069
E = −41.86 kjmol$^{-1}$

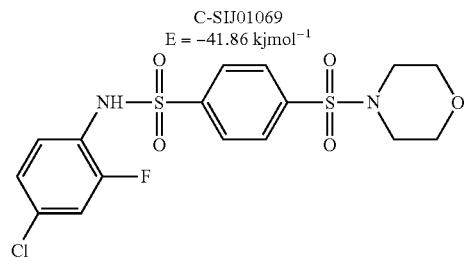

C-SIJ01070
E = −41.64 kjmol$^{-1}$

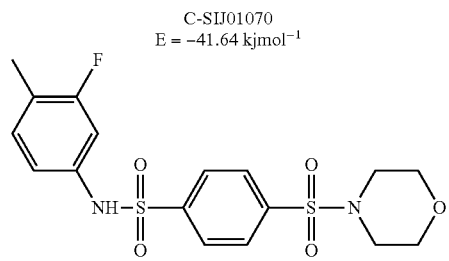

C-SIJ02071
E = −37.69 kjmol$^{-1}$

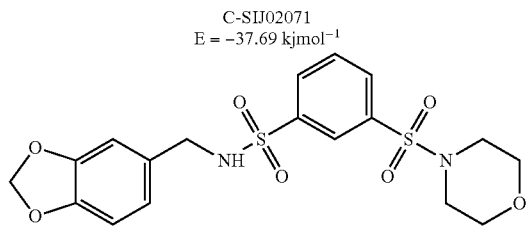

C-SIJ03072
E = −38.61 kjmol$^{-1}$

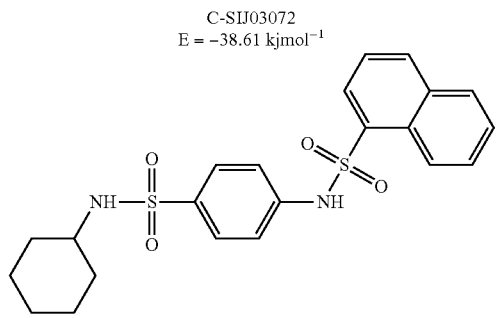

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ03073
E = −39.43 kjmol$^{-1}$

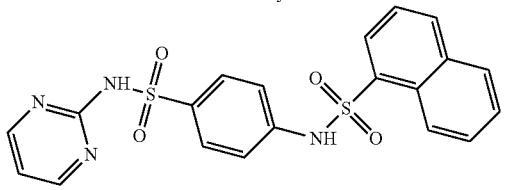

C-SIJ03074
E = −38.89 kjmol$^{-1}$

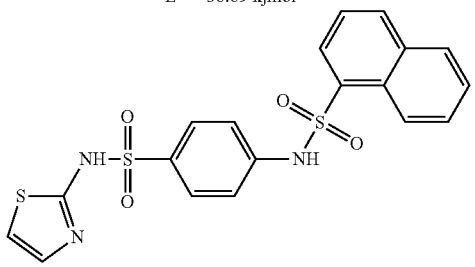

C-SIJ03075
E = −38.56 kjmol$^{-1}$

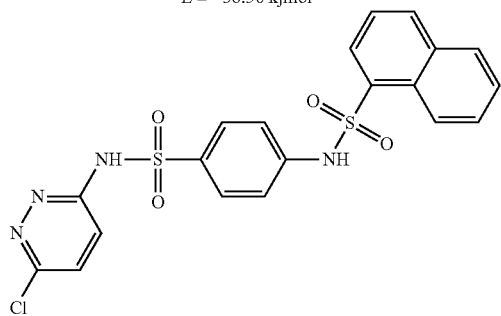

C-SIJ03076
E = −39.65 kjmol$^{-1}$

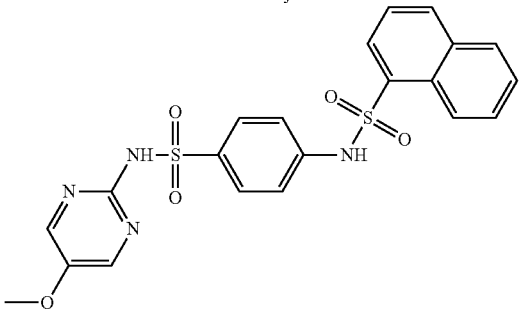

C-SIJ04077
E = −42.76 kjmol$^{-1}$

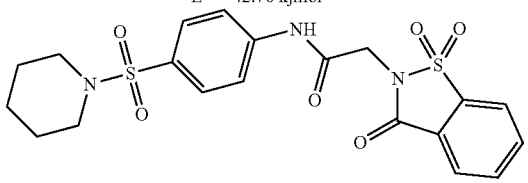

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ04078
E = −42.15 kjmol$^{-1}$

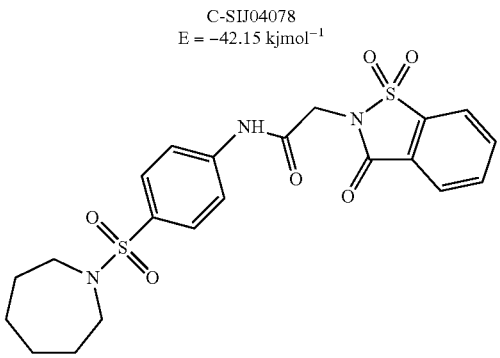

C-SIJ04079
E = −42.57 kjmol$^{-1}$

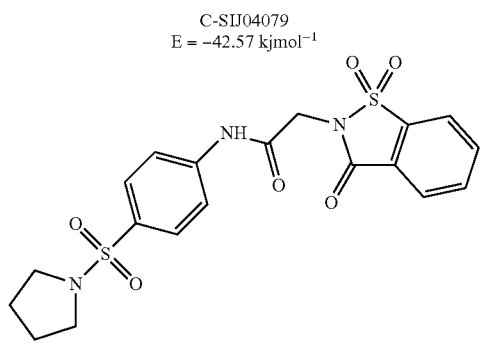

C-SIJ04080
E = −41.95 kjmol$^{-1}$

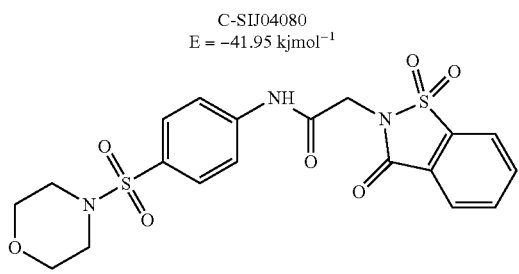

C-SIJ04081
E = −41.87 kjmol$^{-1}$

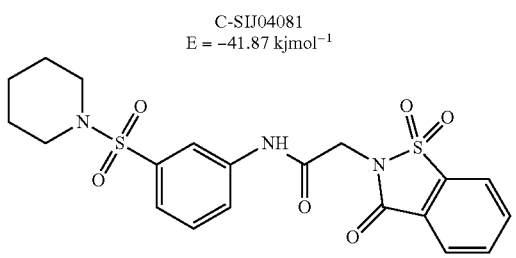

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ04082
E = −42.05 kjmol$^{-1}$

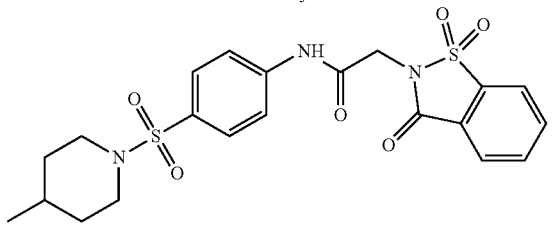

C-SIJ04083
E = −42.74 kjmol$^{-1}$

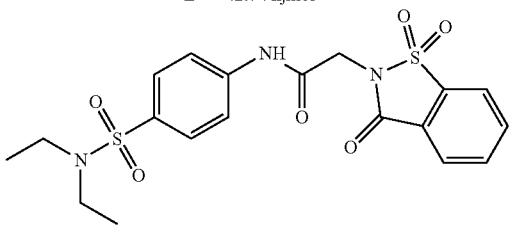

C-SIJ04084
E = −41.88 kjmol$^{-1}$

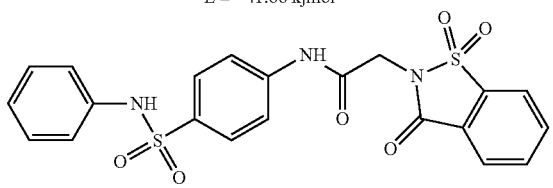

C-SIJ05085
E = −49.25 kjmol$^{-1}$

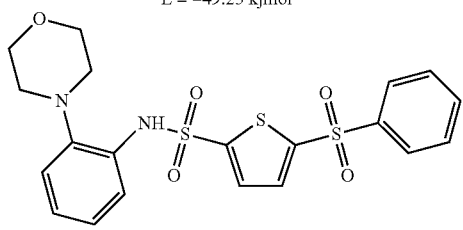

C-SIJ06086
E = −40.84 kjmol$^{-1}$

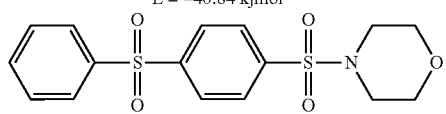

C-SIJ06087
E = −40.84 kjmol$^{-1}$

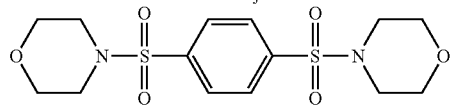

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ06088
E = −40.73 kjmol$^{-1}$

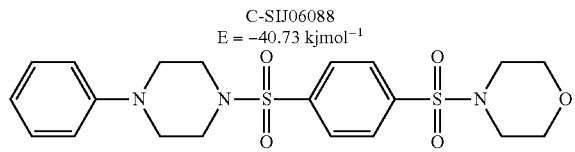

C-SIJ06089
E = −40.24 kjmol$^{-1}$

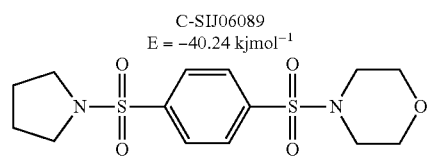

C-SIJ06090
E = −39.81 kjmol$^{-1}$

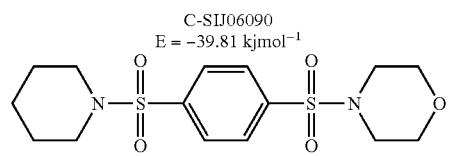

C-SIJ06091
E = −39.34 kjmol$^{-1}$

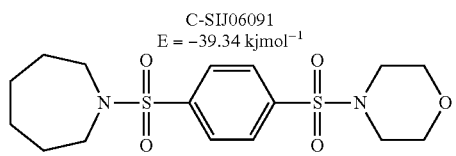

C-SIJ06092
E = −39.53 kjmol$^{-1}$

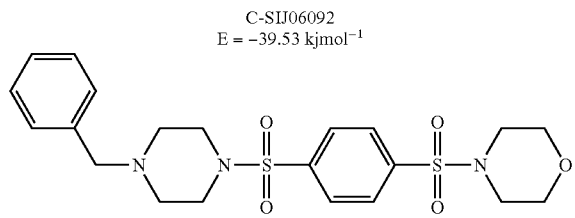

C-SIJ06093
E = −40.11 kjmol$^{-1}$

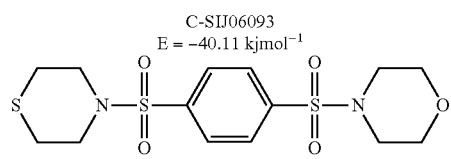

C-SIJ06094
E = −40.04 kjmol$^{-1}$

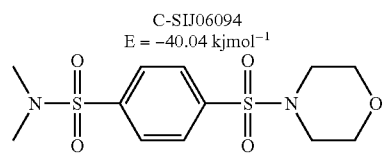

C-SIJ06095
E = −39.76 kjmol$^{-1}$

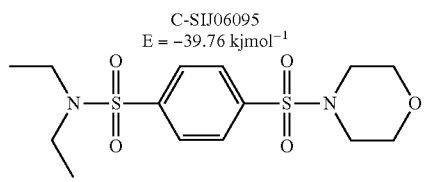

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

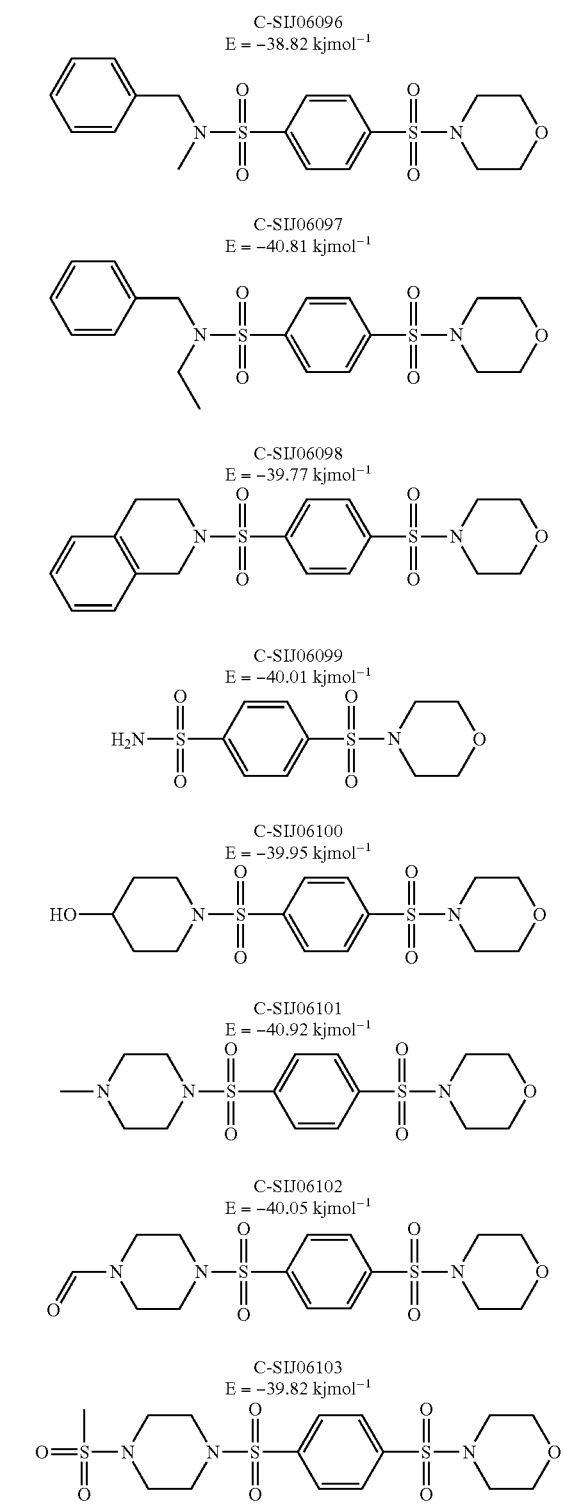

C-SIJ06096
E = −38.82 kjmol$^{-1}$

C-SIJ06097
E = −40.81 kjmol$^{-1}$

C-SIJ06098
E = −39.77 kjmol$^{-1}$

C-SIJ06099
E = −40.01 kjmol$^{-1}$

C-SIJ06100
E = −39.95 kjmol$^{-1}$

C-SIJ06101
E = −40.92 kjmol$^{-1}$

C-SIJ06102
E = −40.05 kjmol$^{-1}$

C-SIJ06103
E = −39.82 kjmol$^{-1}$

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

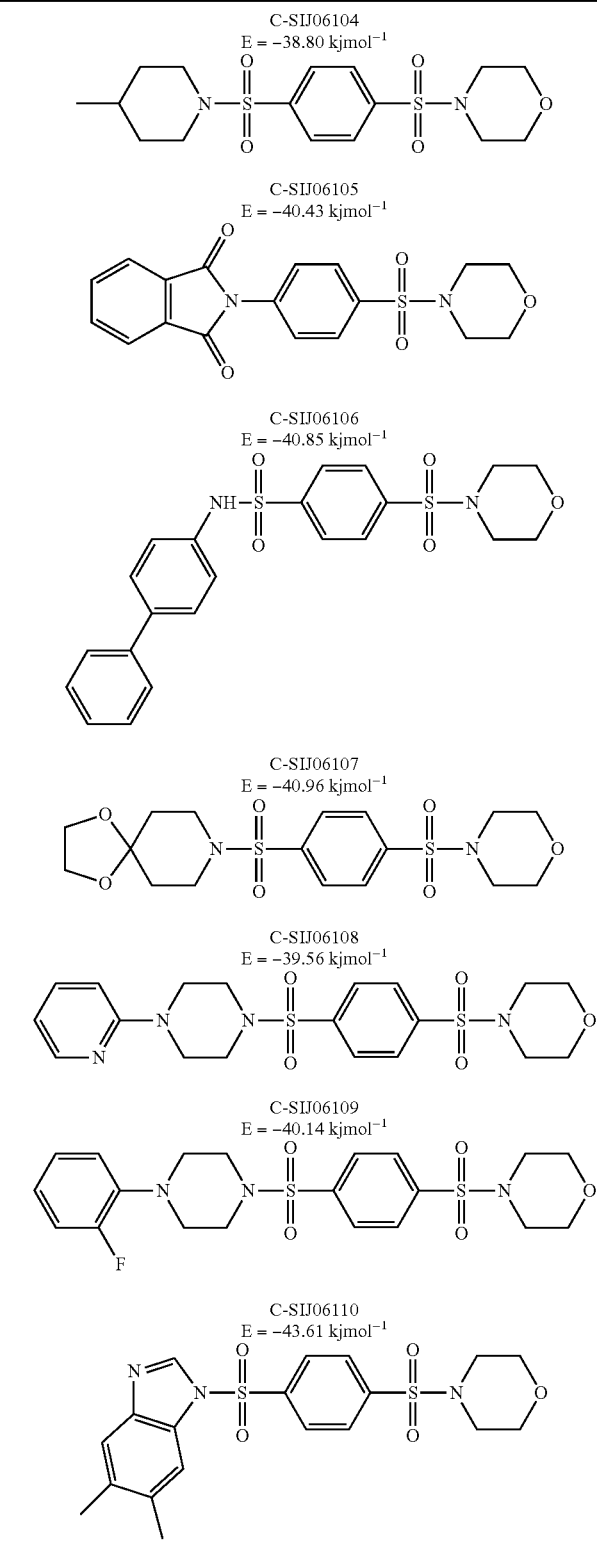

TABLE 1-continued 2D structure and energy binding value of chemical compounds with a
potential favorable binding according to energy evaluation done with scoring
functions of Dock (4.01 and 6.1 versions) and AutoDock programs and according
to the geometry and chemical composition of the atoms forming the binding site.
The reported energy values were calculated with the energy function of Dock
program 4.01.

C-SIJ06111
E = −42.21 kjmol$^{-1}$

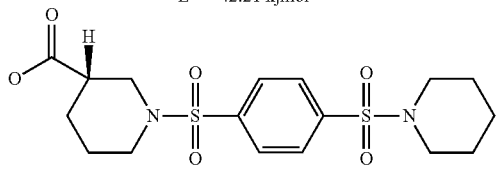

C-SIJ06112
E = −42.34 kjmol$^{-1}$

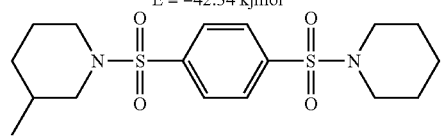

C-SIJ06113
E = −42.13 kjmol$^{-1}$

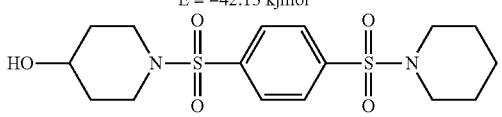

C-SIJ06114
E = −42.01 kjmol$^{-1}$

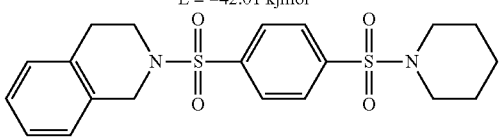

C-SIJ07115
E = −39.83 kjmol$^{-1}$

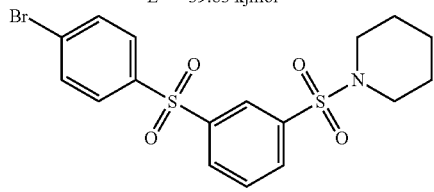

C-SIJ08116
E = −35.57 kjmol$^{-1}$

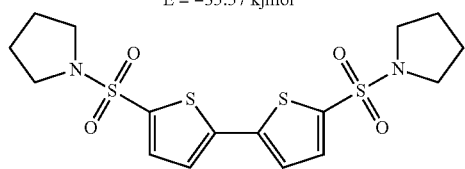

C-SIJ090117
E = −39.53 kjmol$^{-1}$

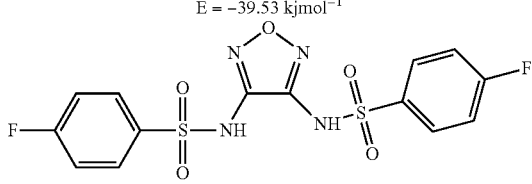

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ10118
E = −37.69 kjmol$^{-1}$

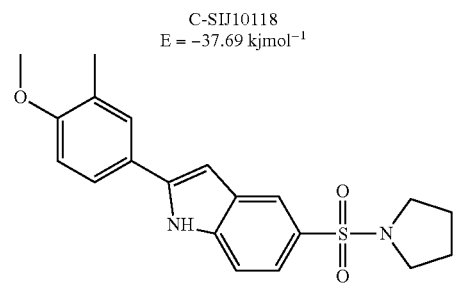

C-SIJ10119
E = −35.89 kjmol$^{-1}$

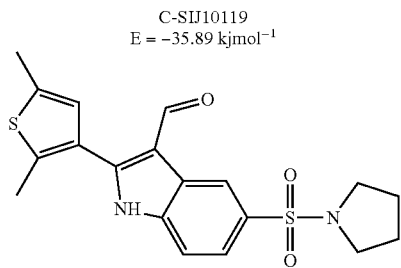

C-SIJ10120
E = −38.85 kjmol$^{-1}$

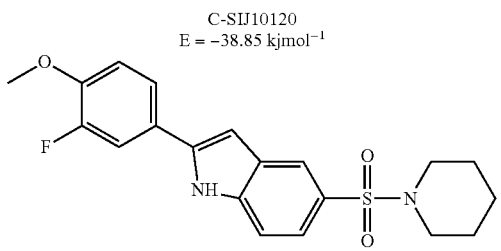

C-SIJ11121
E = −43.71 kjmol$^{-1}$

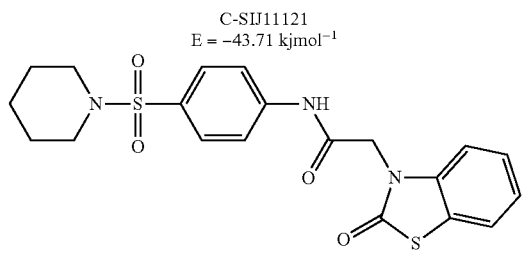

C-SIJ11122
E = −39.65 kjmol$^{-1}$

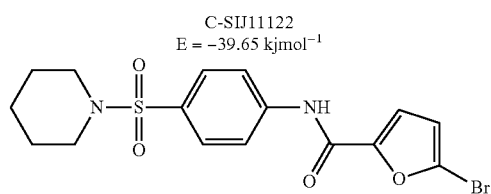

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

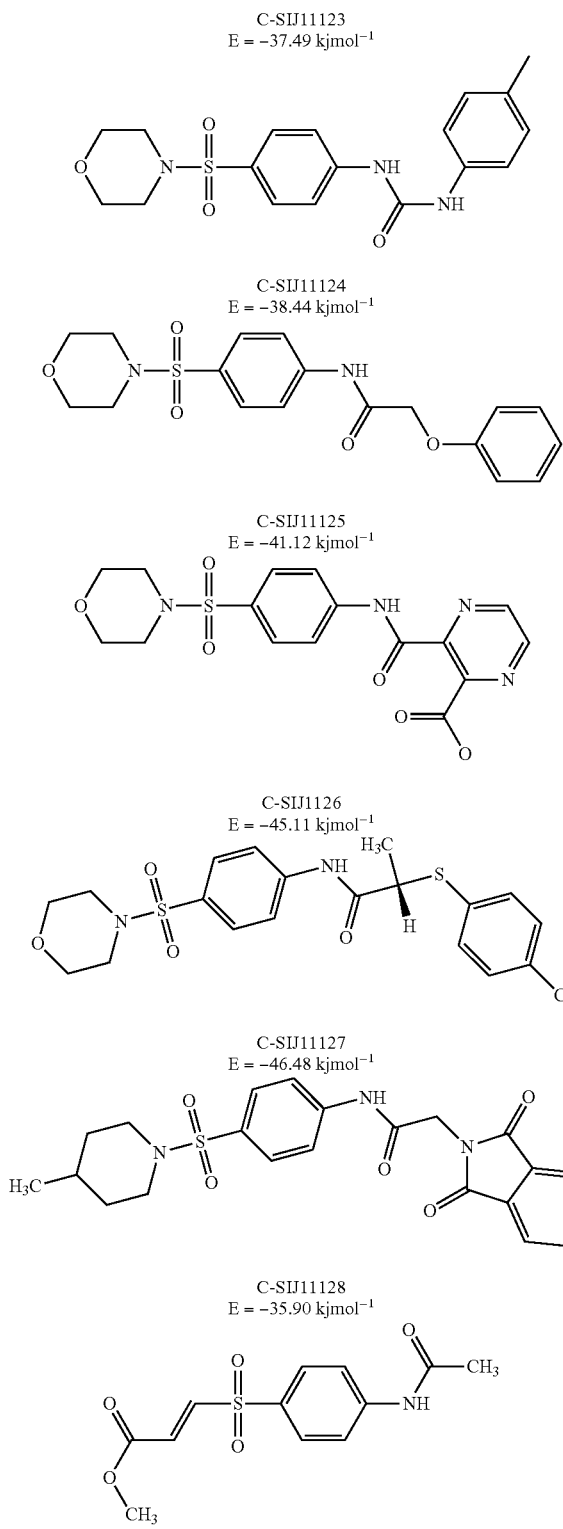

C-SIJ11123
E = −37.49 kjmol$^{-1}$

C-SIJ11124
E = −38.44 kjmol$^{-1}$

C-SIJ11125
E = −41.12 kjmol$^{-1}$

C-SIJ1126
E = −45.11 kjmol$^{-1}$

C-SIJ11127
E = −46.48 kjmol$^{-1}$

C-SIJ11128
E = −35.90 kjmol$^{-1}$

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ11129
E = −41.45 kjmol$^{-1}$

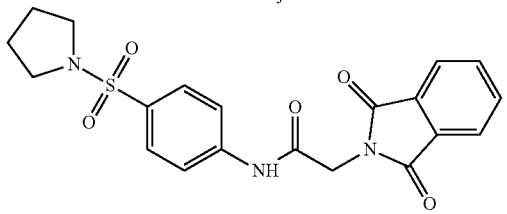

C-SIJ11130
E = −41.32 kjmol$^{-1}$

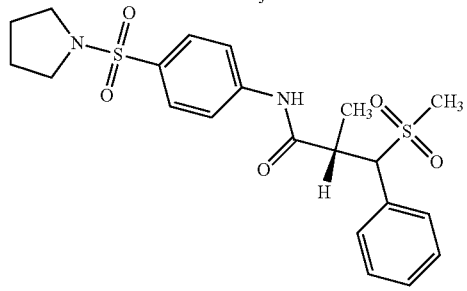

C-SIJ11131
E = −40.35 kjmol$^{-1}$

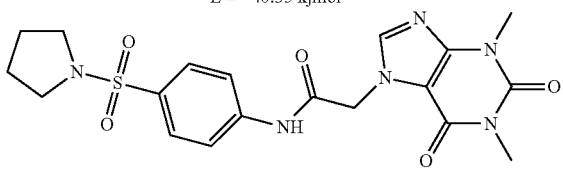

C-SIJ11132
E = −35.49 kjmol$^{-1}$

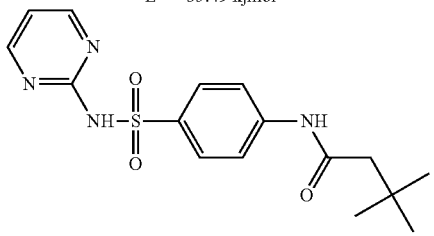

C-SIJ11133
E = −40.75 kjmol$^{-1}$

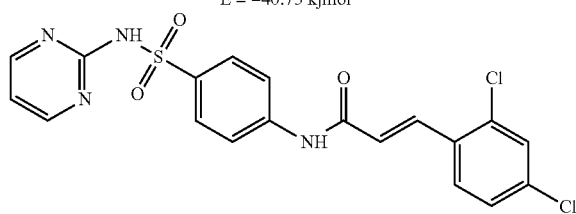

TABLE 1-continued 2D structure and energy binding value of chemical compounds with a
potential favorable binding according to energy evaluation done with scoring
functions of Dock (4.01 and 6.1 versions) and AutoDock programs and according
to the geometry and chemical composition of the atoms forming the binding site.
The reported energy values were calculated with the energy function of Dock
program 4.01.

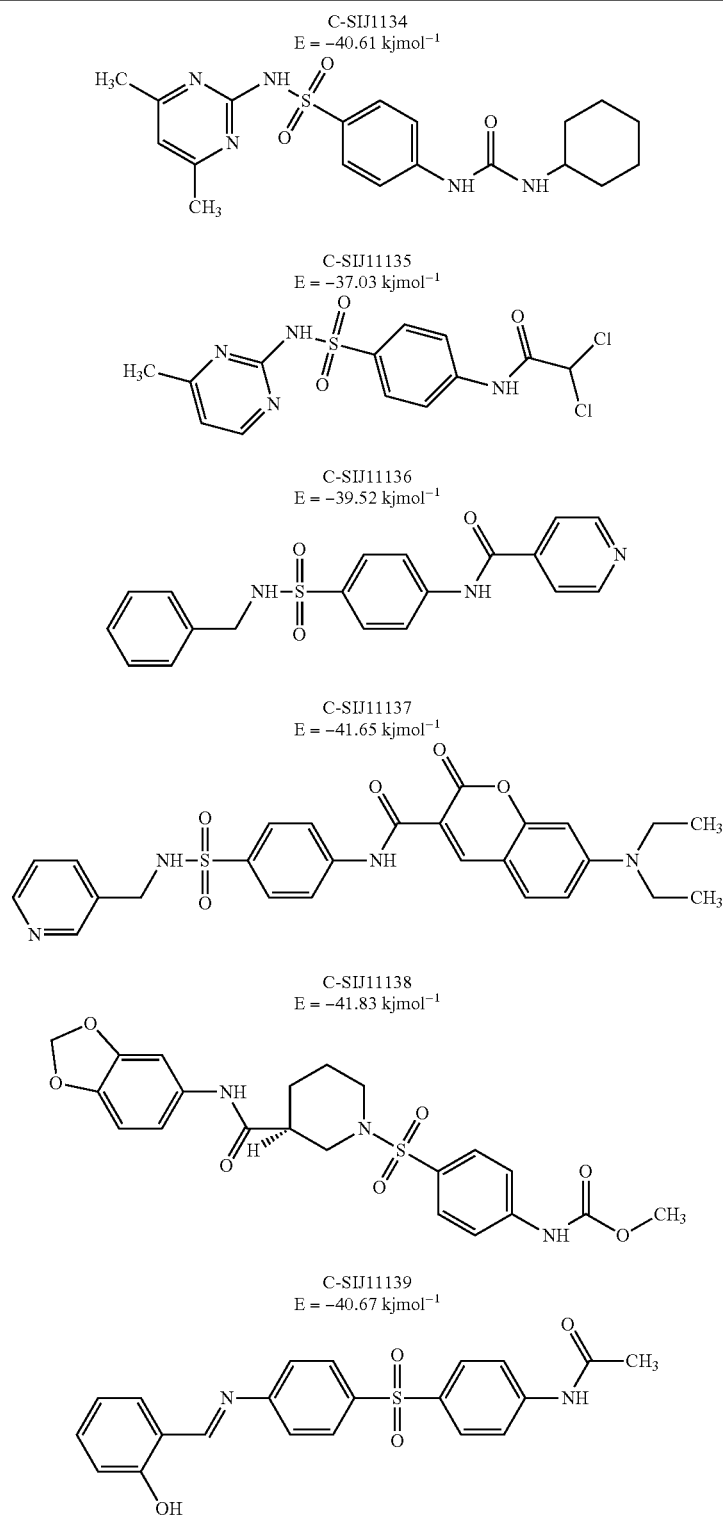

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

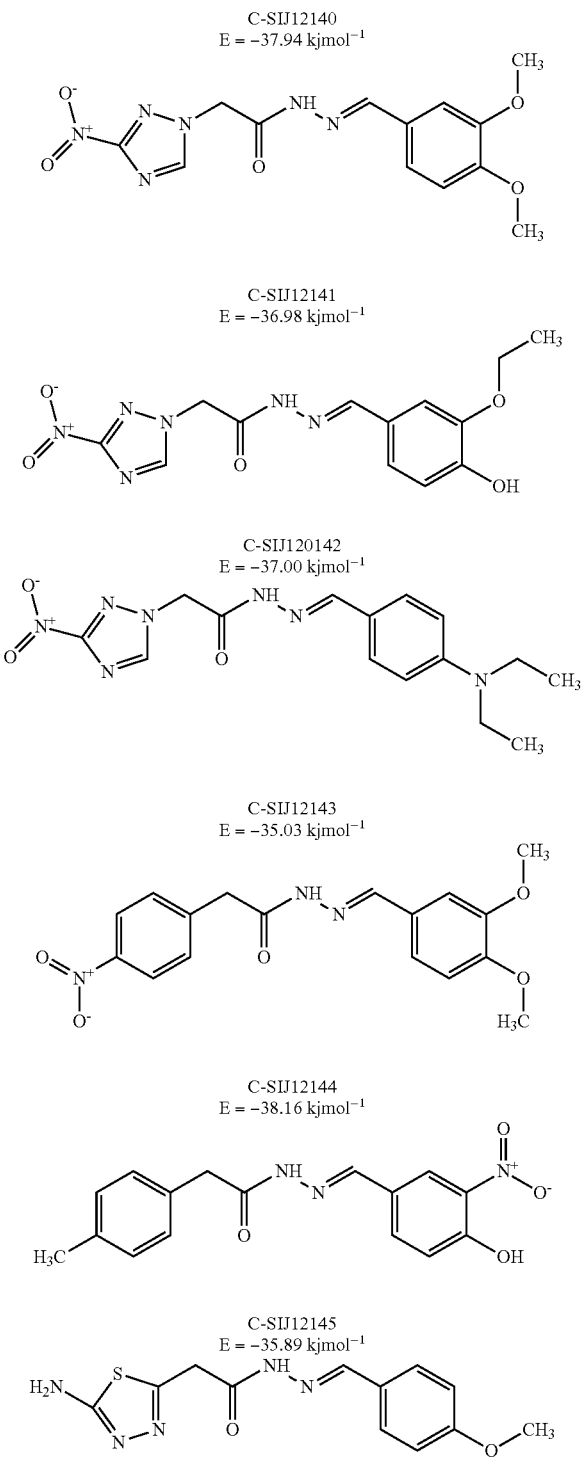

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ12146
E = −35.76 kjmol$^{-1}$

C-SIJ12147
E = −35.90 kjmol$^{-1}$

C-SIJ12148
E = −36.05 kjmol$^{-1}$

C-SIJ12149
E = −39.86 kjmol$^{-1}$

C-SIJ13150
E = −38.28 kjmol$^{-1}$

C-SIJ130151
E = −38.95 kjmol$^{-1}$

C-SIJ13152
E = −43.54 kjmol$^{-1}$

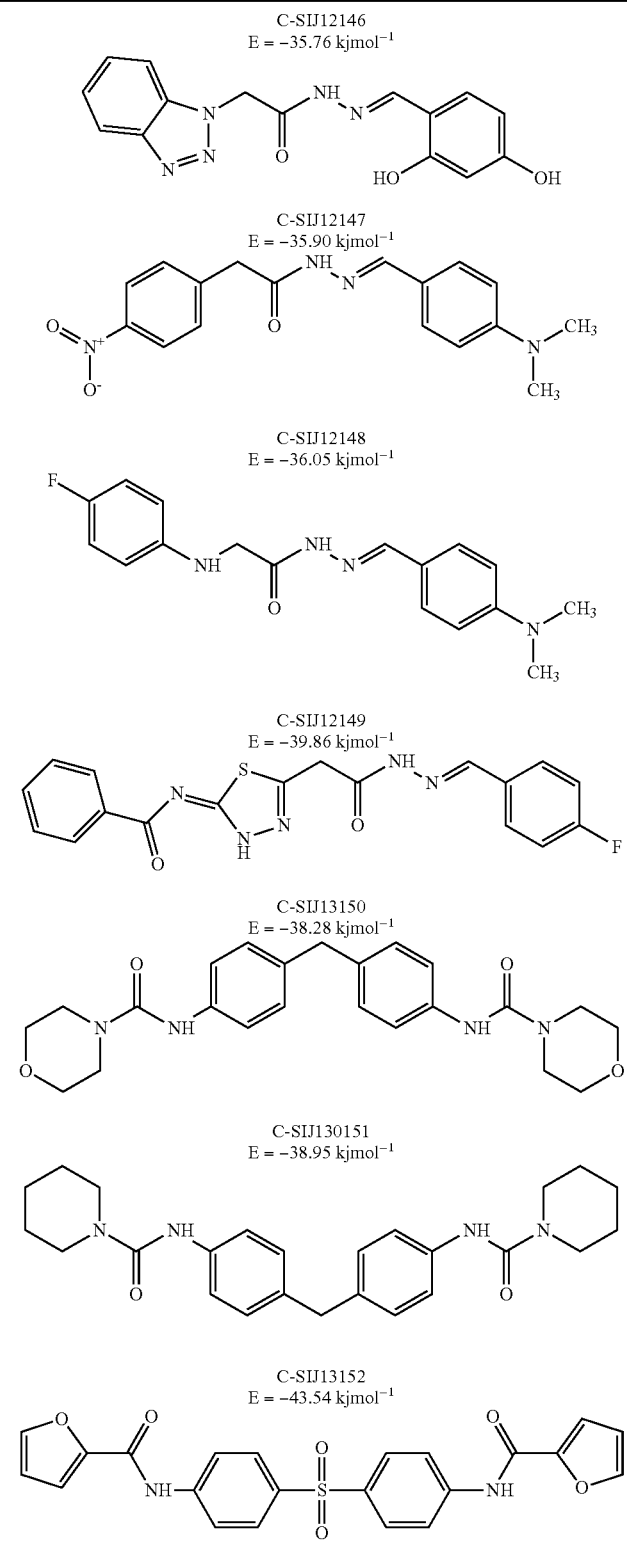

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

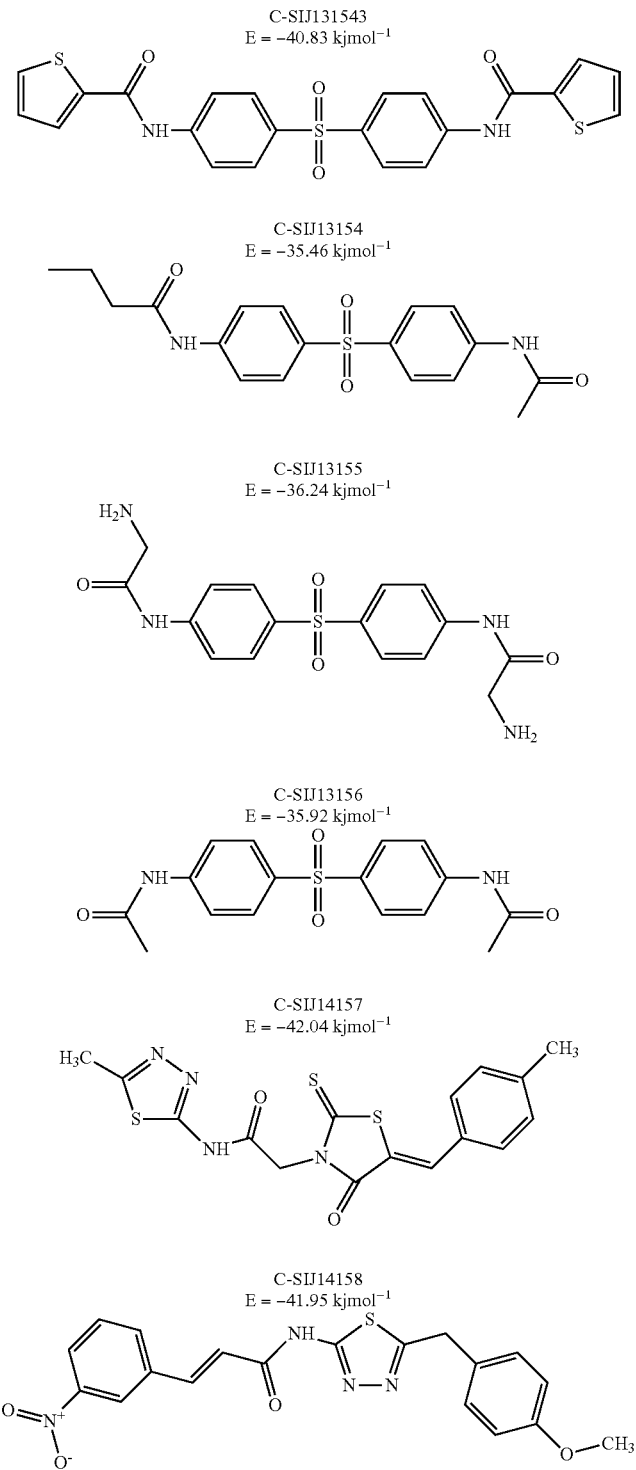

C-SIJ131543
E = −40.83 kjmol$^{-1}$

C-SIJ13154
E = −35.46 kjmol$^{-1}$

C-SIJ13155
E = −36.24 kjmol$^{-1}$

C-SIJ13156
E = −35.92 kjmol$^{-1}$

C-SIJ14157
E = −42.04 kjmol$^{-1}$

C-SIJ14158
E = −41.95 kjmol$^{-1}$

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

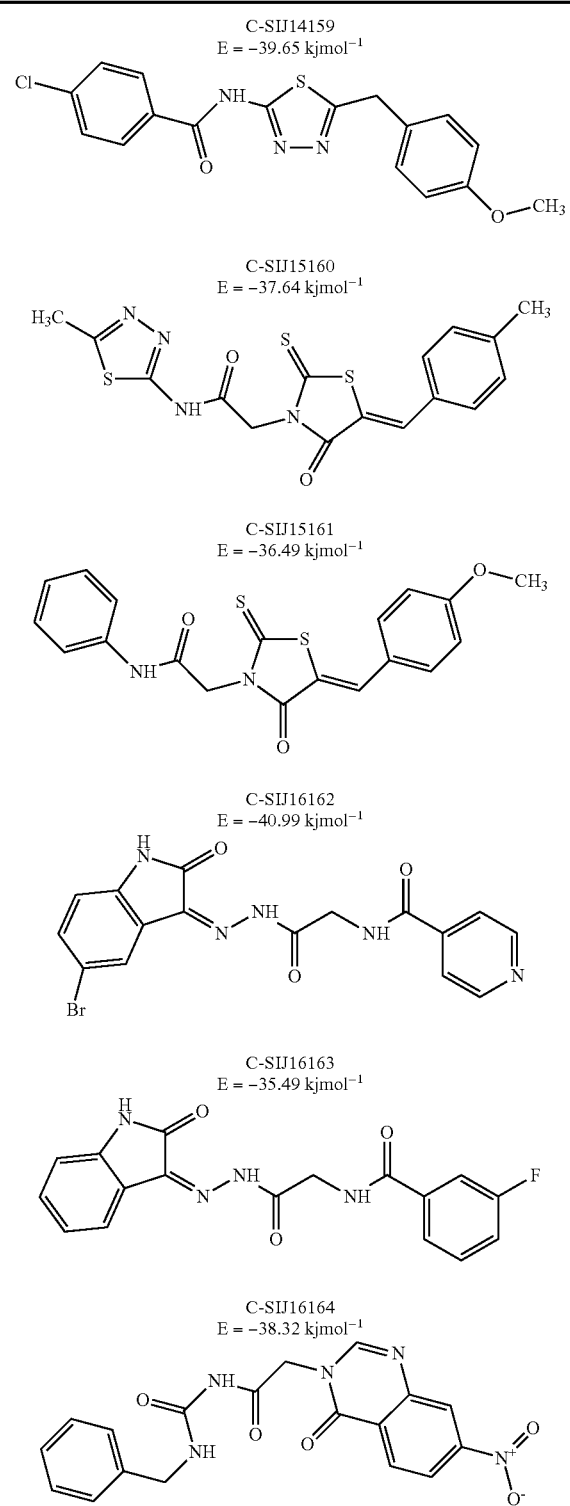

C-SIJ14159
E = −39.65 kjmol$^{-1}$

C-SIJ15160
E = −37.64 kjmol$^{-1}$

C-SIJ15161
E = −36.49 kjmol$^{-1}$

C-SIJ16162
E = −40.99 kjmol$^{-1}$

C-SIJ16163
E = −35.49 kjmol$^{-1}$

C-SIJ16164
E = −38.32 kjmol$^{-1}$

TABLE 1-continued 2D structure and energy binding value of chemical compounds with a
potential favorable binding according to energy evaluation done with scoring
functions of Dock (4.01 and 6.1 versions) and AutoDock programs and according
to the geometry and chemical composition of the atoms forming the binding site.
The reported energy values were calculated with the energy function of Dock
program 4.01.

C-SIJ16165
E = −39.61 kjmol$^{-1}$

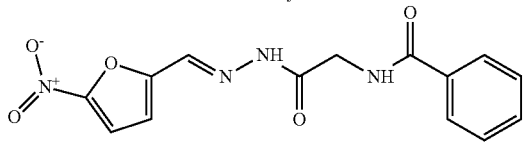

C-SIJ17166
E = −41.78 kjmol$^{-1}$

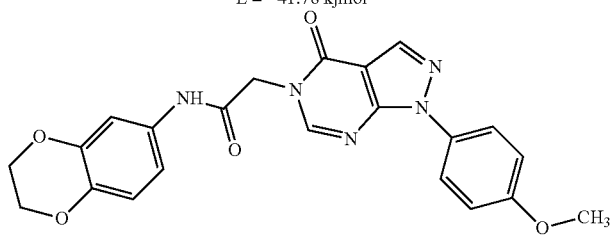

C-SIJ17167
E = −41.81 kjmol$^{-1}$

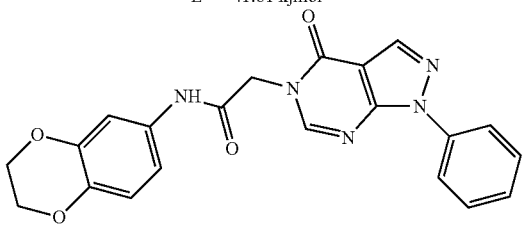

C-SIJ18168
E = −35.12 kjmol$^{-1}$

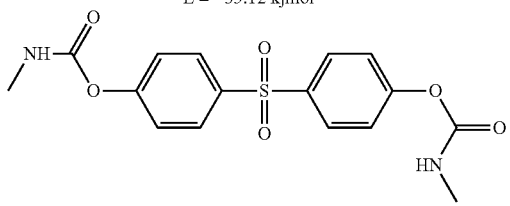

C-SIJ18169
E = −35.81 kjmol$^{-1}$

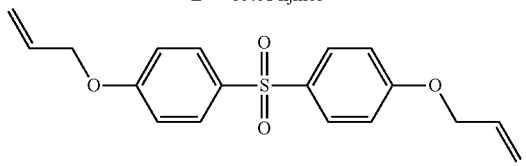

C-SIJ19170
E = −39.59 kjmol$^{-1}$

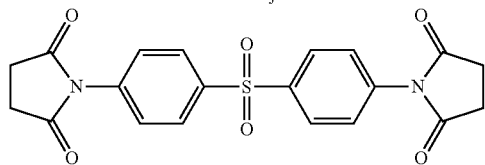

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

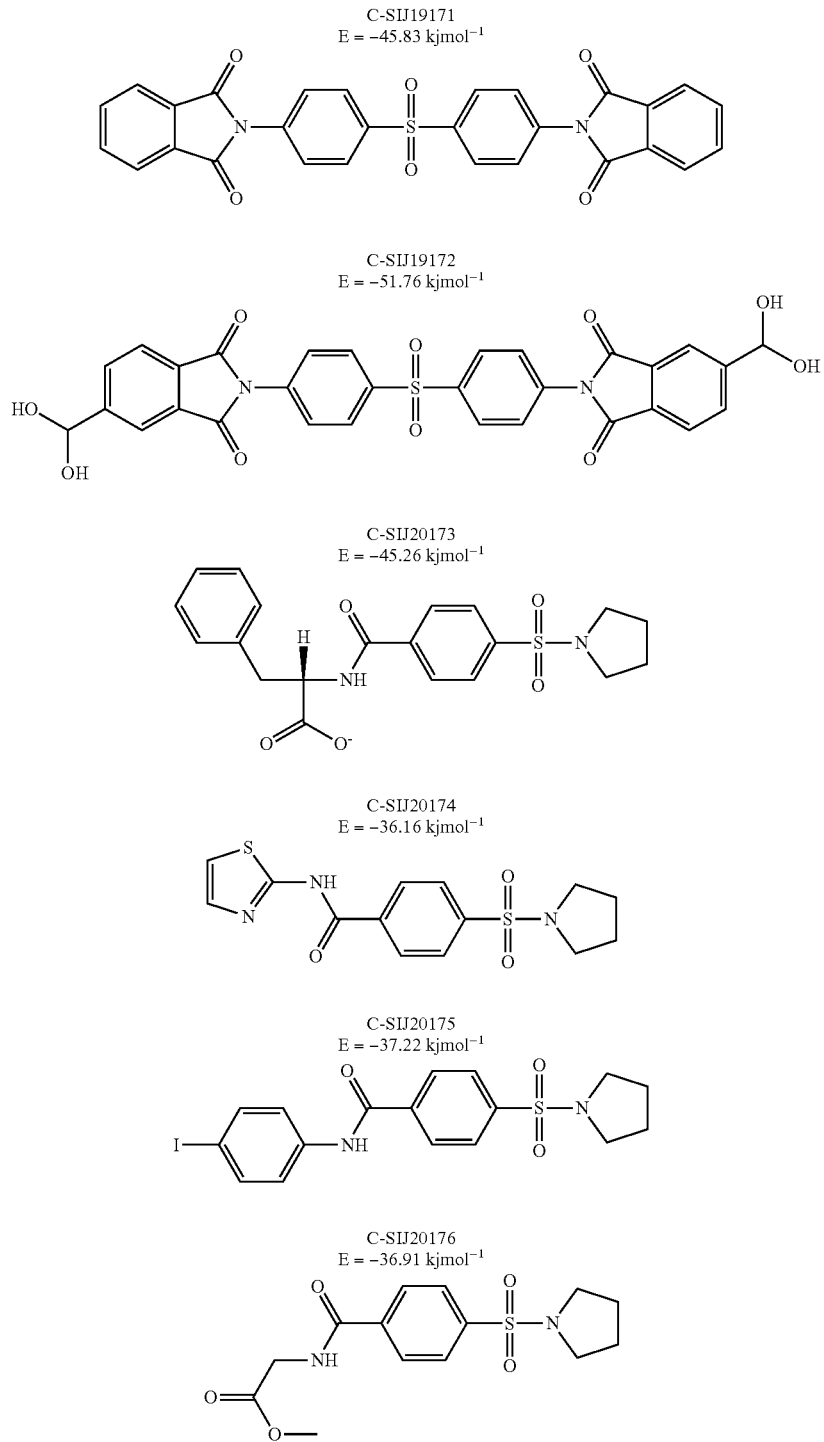

C-SIJ19171
E = −45.83 kjmol$^{-1}$

C-SIJ19172
E = −51.76 kjmol$^{-1}$

C-SIJ20173
E = −45.26 kjmol$^{-1}$

C-SIJ20174
E = −36.16 kjmol$^{-1}$

C-SIJ20175
E = −37.22 kjmol$^{-1}$

C-SIJ20176
E = −36.91 kjmol$^{-1}$

TABLE 1-continued 2D structure and energy binding value of chemical compounds with a
potential favorable binding according to energy evaluation done with scoring
functions of Dock (4.01 and 6.1 versions) and AutoDock programs and according
to the geometry and chemical composition of the atoms forming the binding site.
The reported energy values were calculated with the energy function of Dock
program 4.01.

C-SIJ20177
$E = -39.12$ kjmol$^{-1}$

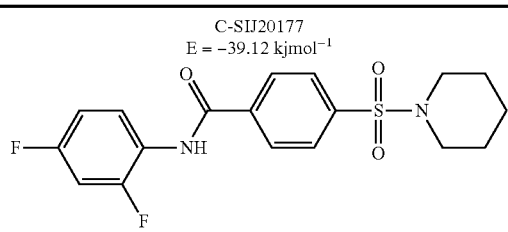

C-S1J20178
$E = -39.12$ kjmol$^{-1}$

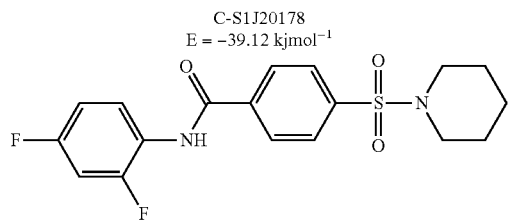

C-S1J20179
$E = -37.61$ kjmol$^{-1}$

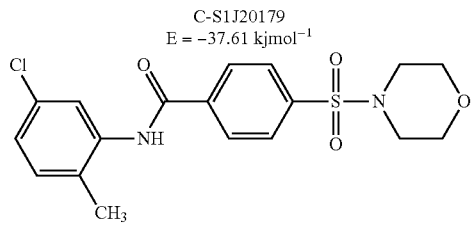

C-S1J21180
$E = -45.03$ kjmol$^{-1}$

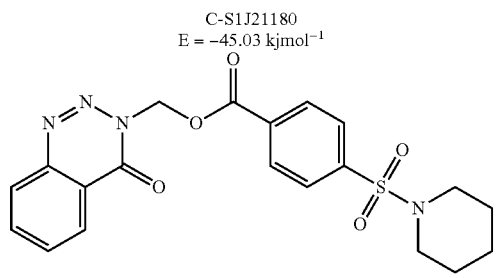

C-SIJ21181
$E = -38.83$ kjmol$^{-1}$

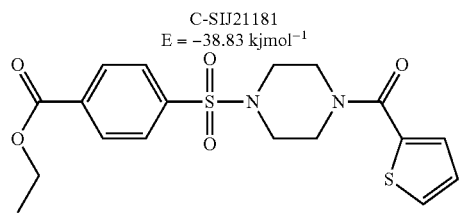

C-SIJ22182
$E = -39.43$ kjmol$^{-1}$

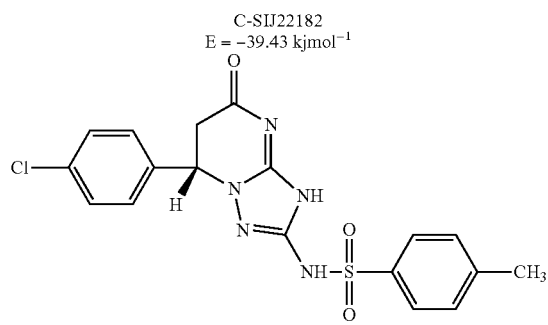

TABLE 1-continued 2D structure and energy binding value of chemical compounds with a
potential favorable binding according to energy evaluation done with scoring
functions of Dock (4.01 and 6.1 versions) and AutoDock programs and according
to the geometry and chemical composition of the atoms forming the binding site.
The reported energy values were calculated with the energy function of Dock
program 4.01.

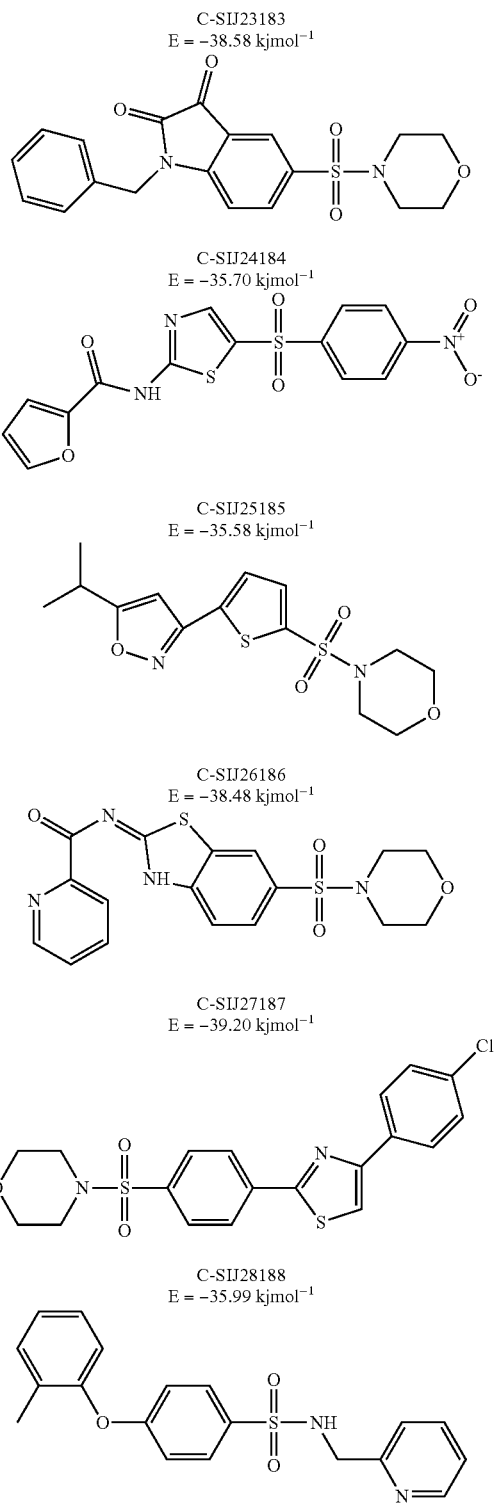

C-SIJ23183
E = −38.58 kjmol$^{-1}$

C-SIJ24184
E = −35.70 kjmol$^{-1}$

C-SIJ25185
E = −35.58 kjmol$^{-1}$

C-SIJ26186
E = −38.48 kjmol$^{-1}$

C-SIJ27187
E = −39.20 kjmol$^{-1}$

C-SIJ28188
E = −35.99 kjmol$^{-1}$

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

C-SIJ29189
E = −37.53 kjmol$^{-1}$

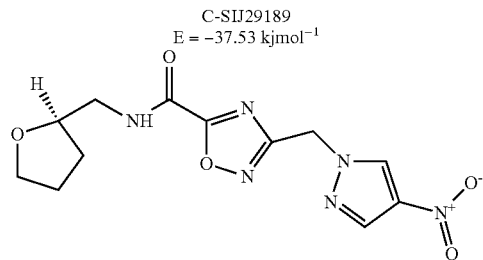

C-SIJ30190
E = −37.16 kjmol$^{-1}$

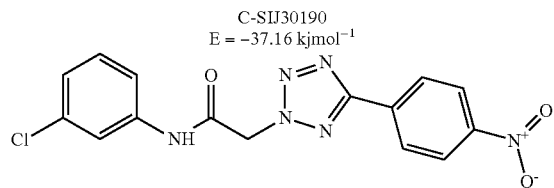

C-SIJ31191
E = −40.77 kjmol$^{-1}$

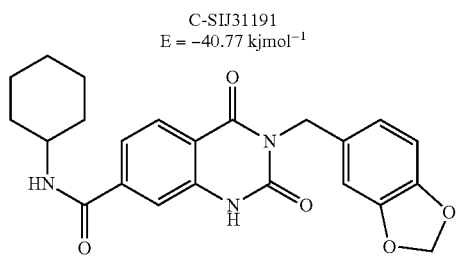

C-SIJ32192
E = −41.81 kjmol$^{-1}$

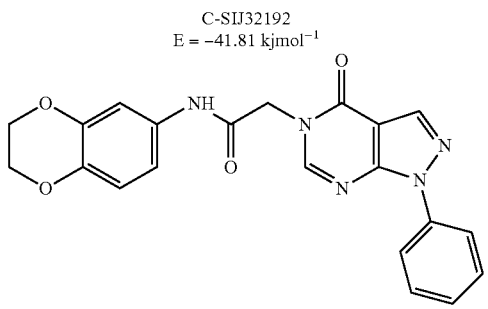

C-SIJ33193
E = −36.16 kjmol$^{-1}$

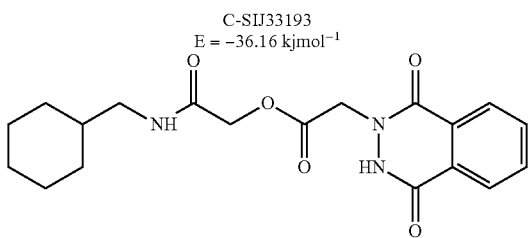

TABLE 1-continued 2D structure and energy binding value of chemical compounds with a potential favorable binding according to energy evaluation done with scoring functions of Dock (4.01 and 6.1 versions) and AutoDock programs and according to the geometry and chemical composition of the atoms forming the binding site. The reported energy values were calculated with the energy function of Dock program 4.01.

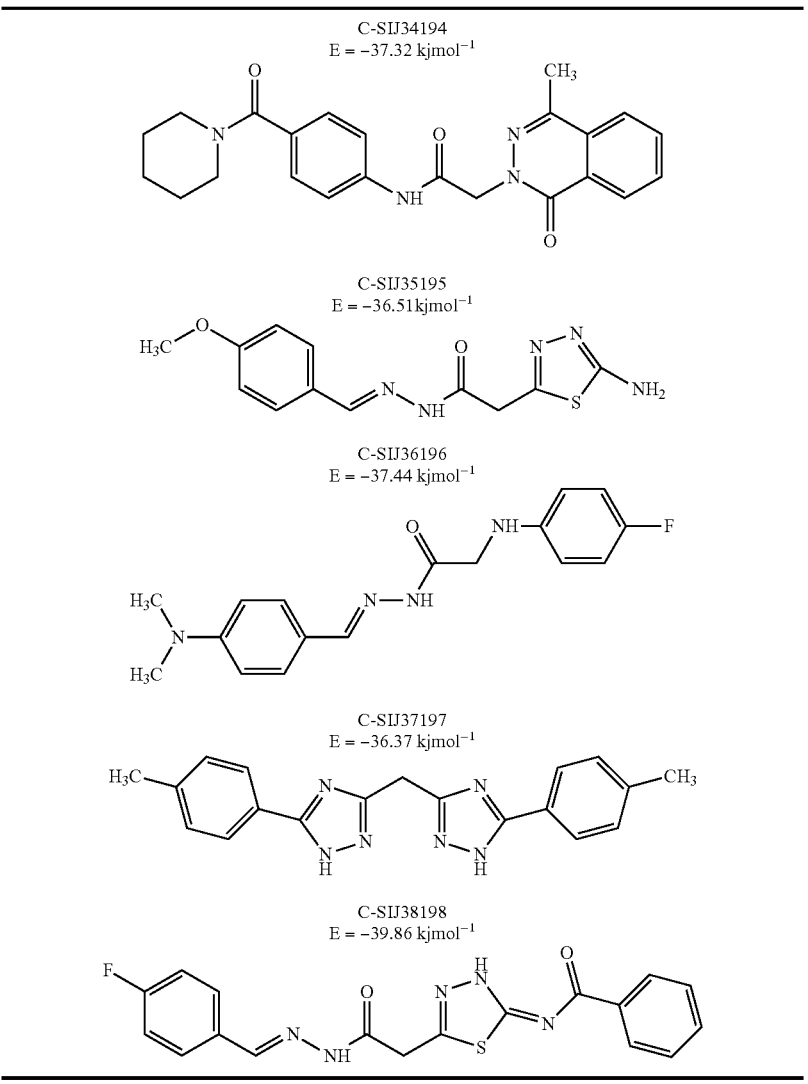

Example 3

Description of the Anchor Substructures

The visual analysis of in silico predicted binding mode of chemical compounds docked into the cleft associated to "ij" loop with the highest energy values allowed the detection of substructures with potential favorable interactions with the key residues for the anchorage to the cleft associated to "ij" loop including: Thr-70, Ser-72, Val-97, Asp-98, Arg-99, Asn-103, Ile-113, Thr-115, Ala-245, Lys-246, Lys-247, Gln-248 Asp-249 and Val-250. Such substructures are recognized as anchor substructures in the present invention. The anchor substructures allowed definition of a 3D pharmacophoric model (FIG. 5) having favorable interatomic interactions with the key residues for the anchorage to the cleft associated to "ij" loop. The construction of the 3D pharmacophoric model described in this invention was completed using 3DFS program (Wang, T. y Zhou, J. (1998) 3DFS: A New 3D Flexible Searching System for Use in Drug Design. J. Chem. Inf. Comput. Sci. 38: 71-77). Such 3D pharmacophoric model was used for the in silico identification of new anchor substructures, which were later oriented into the receptor binding site and evaluated using Dock program, similar to that described in Example 2. The anchor substructures were clustered based on their chemical similarity and binding mode into the groove associated to "ij" loop. The anchor substructures described in the present invention contain at least three of the following elements: a) an hydrogen bond donor element ($D_{1-4}$), and/or b) an hydrogen bond acceptor element and/or negative charged group ($A_1$-, $A_2$-, $A_3$), and/or c) an hydrophobic element ($H_{1-3}$), and/or d) an hydrogen bond acceptor and/or hydrogen bond donor element (D/A), and/or e) a simultaneously donor-acceptor hydrogen bond element (D+A), and these elements (a)-(e) are selected among the elements that constitute the 3D pharmacophoric model and are described below:
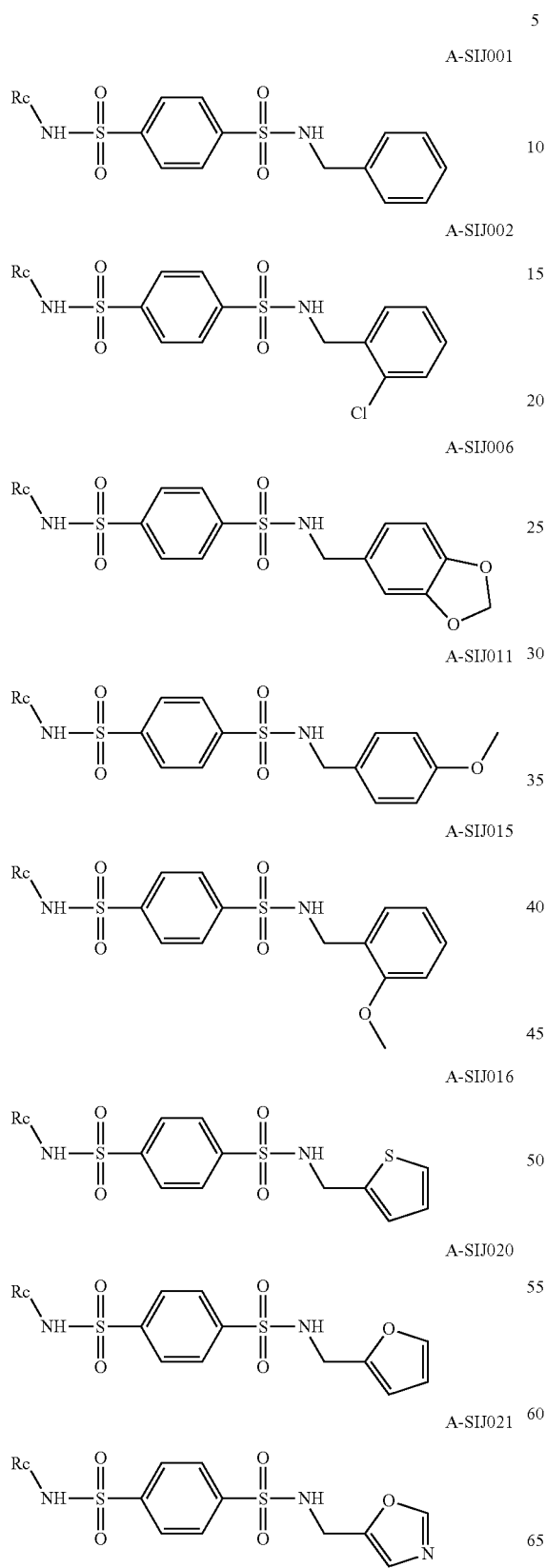
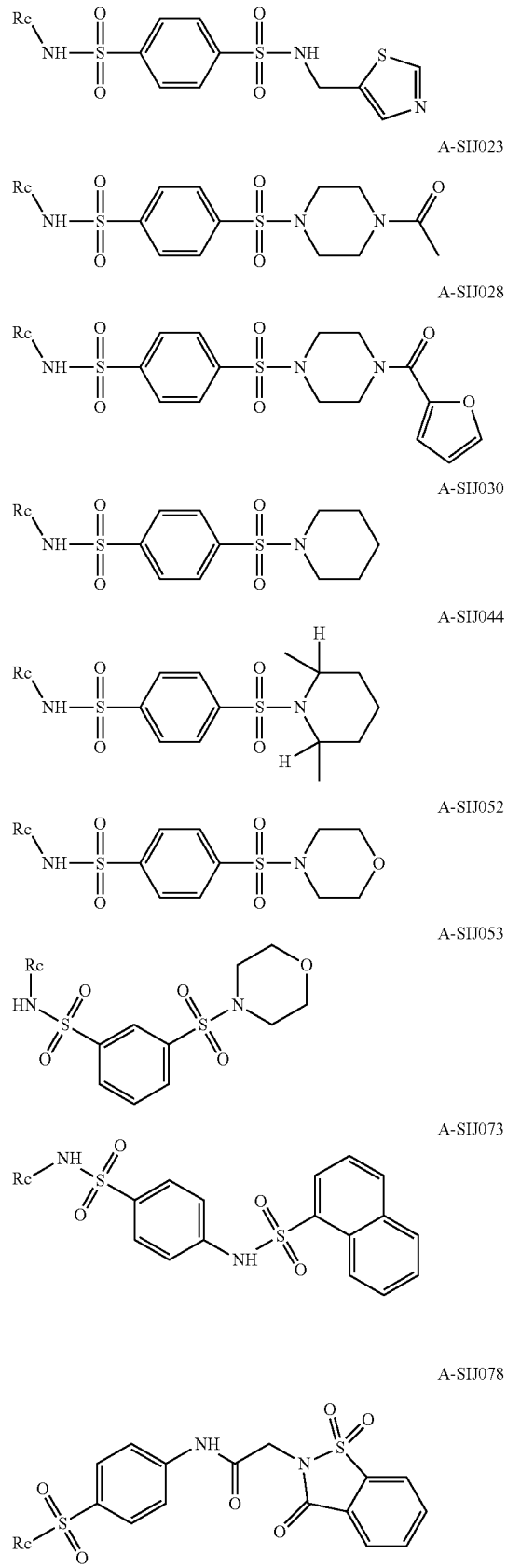

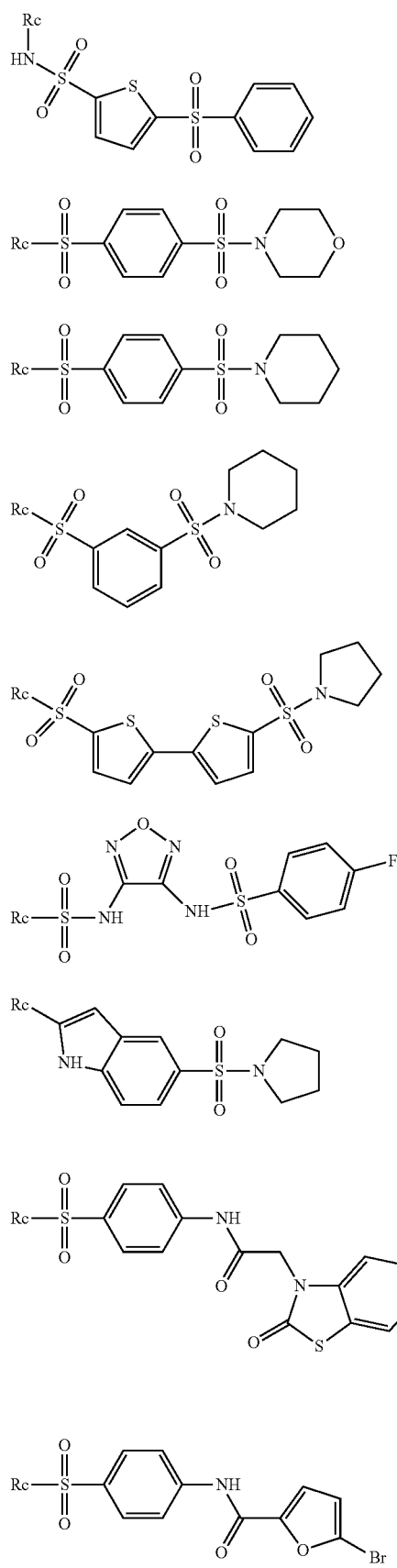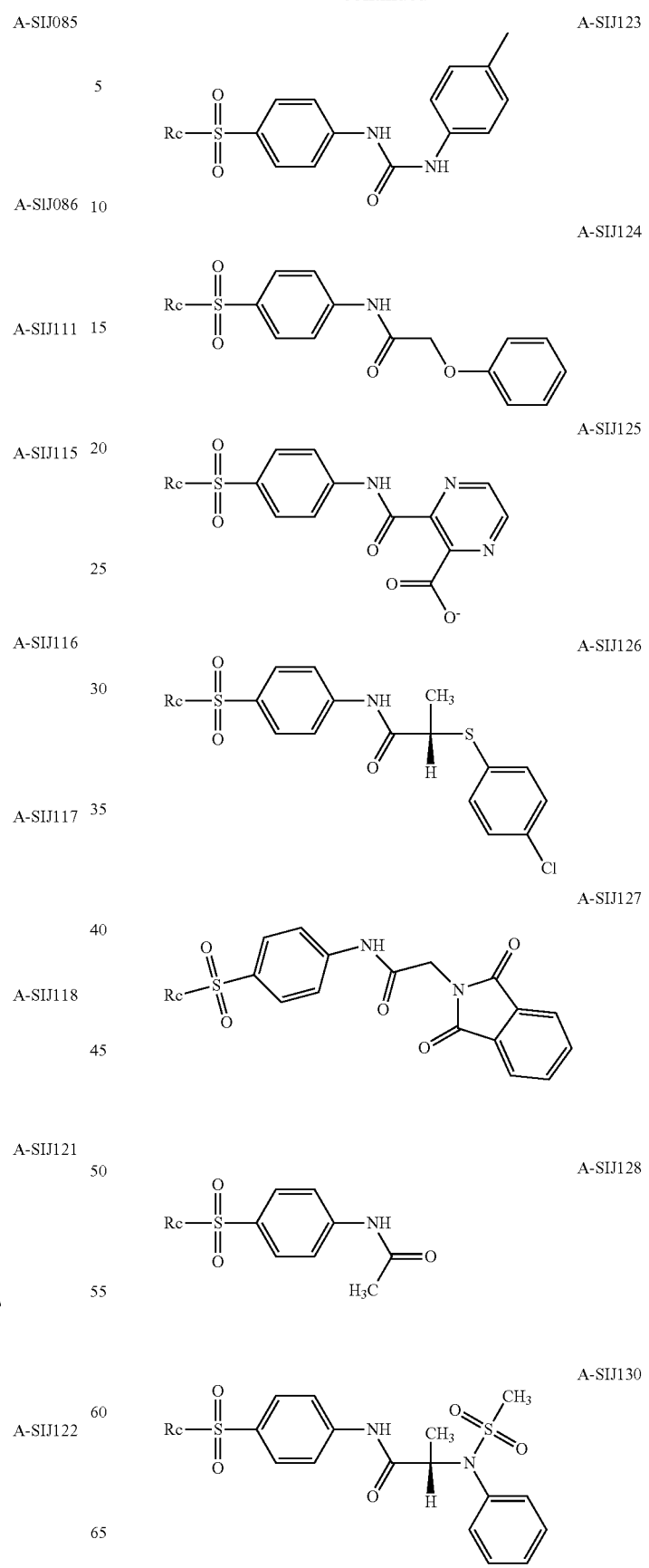

A-SIJ131
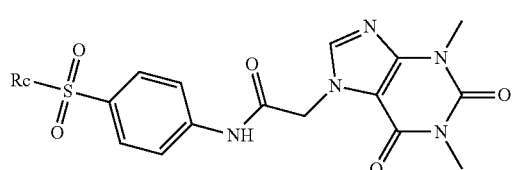
A-SIJ132
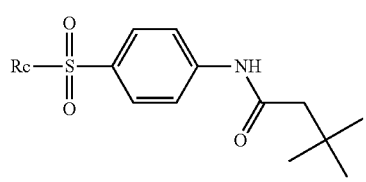
A-SIJ133
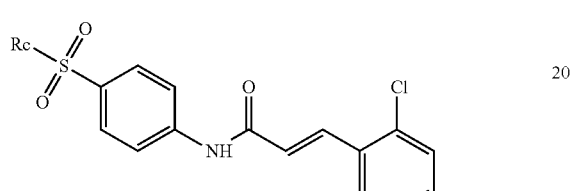
A-SIJ134
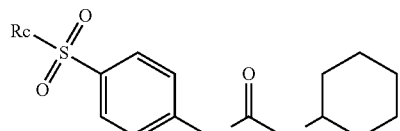
A-SIJ135
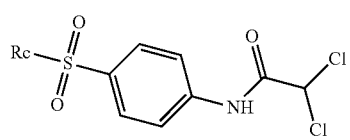
A-SIJ136
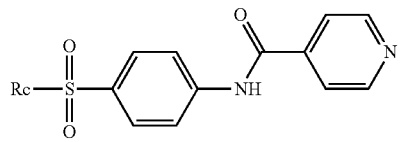
A-SIJ137
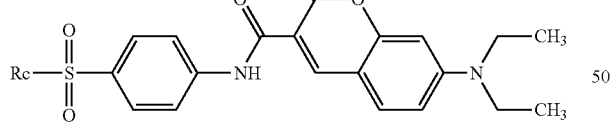
A-SIJ138
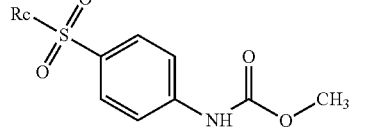
A-SIJ140
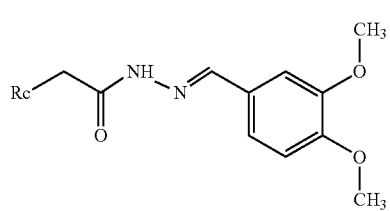
A-SIJ141
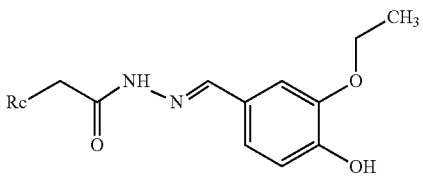
A-SIJ142
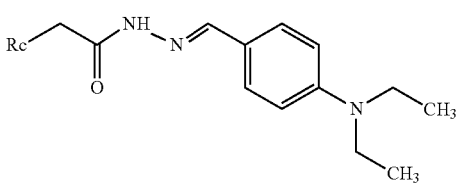
A-SIJ144
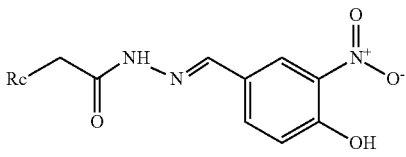
A-SIJ145
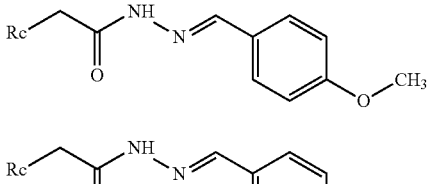
A-SIJ146
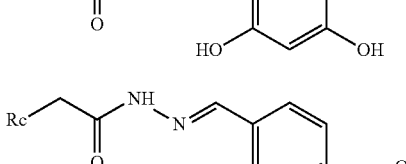
A-SIJ147
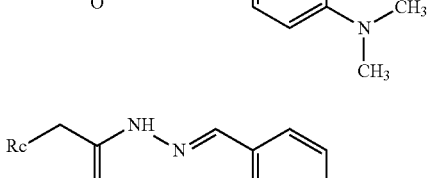
A-SIJ149
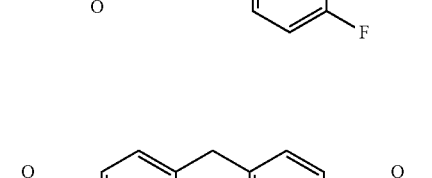
A-SIJ150
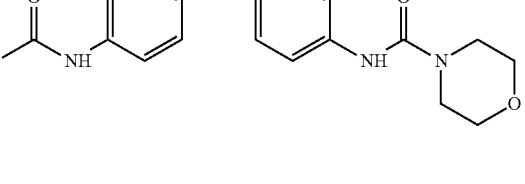
A-SIJ151

-continued

A-SIJ152, A-SIJ153, A-SIJ154, A-SIJ155, A-SIJ156, A-SIJ157, A-SIJ159, A-SIJ160, A-SIJ161, A-SIJ162, A-SIJ163, A-SIJ164, A-SIJ165, A-SIJ166, A-SIJ167, A-SIJ168

103
-continued

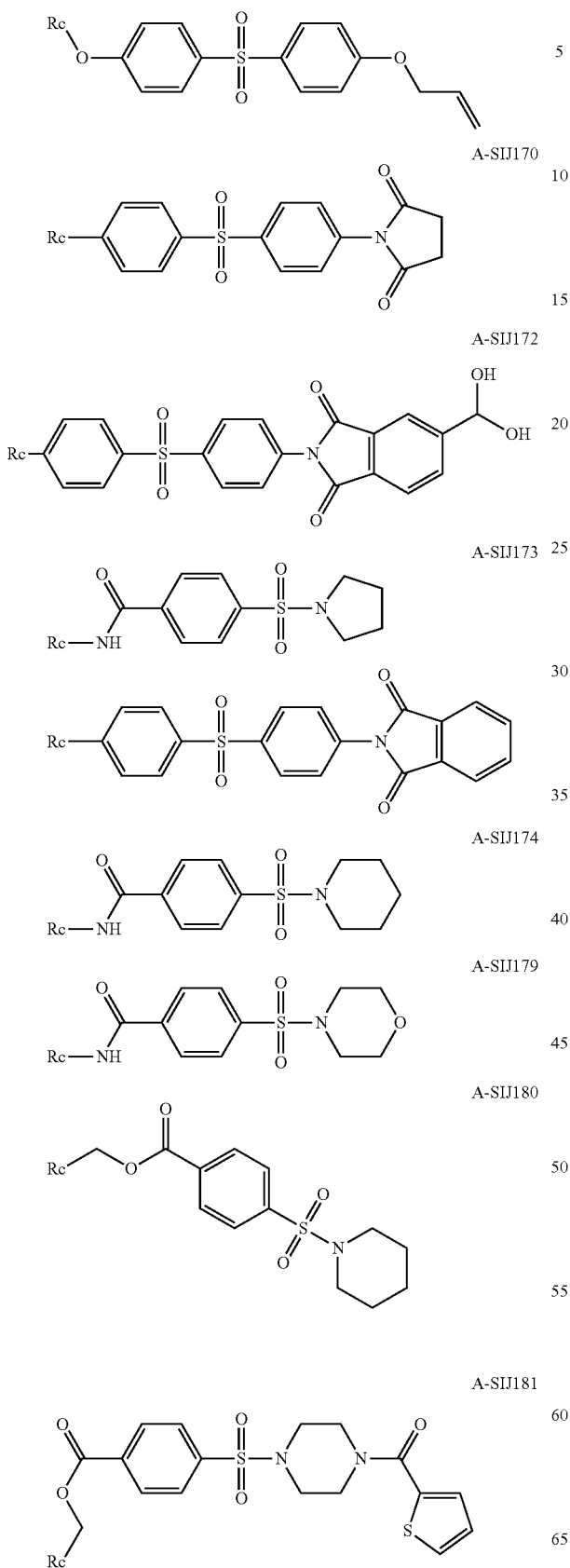

104
-continued

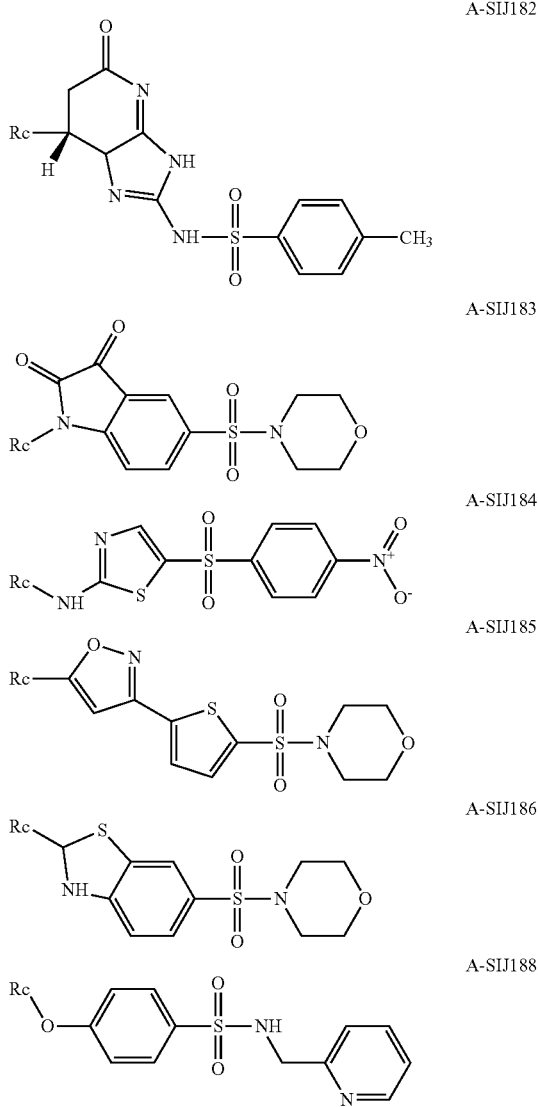

Example 4

Relation Pharmacophore Model-Anchor Substructure

Each element of the pharmacophore model described in the present invention interacts with at least three of the key residues for the anchorage to the cleft associated to "ij" loop. The anchor substructures described in the present invention contain at least three of the elements present in the pharmacophore model. Next it is described the binding mode of some anchor substructures.

Anchor A-SIJ023

The anchor substructure A-SIJ023 contains the following elements of the pharmacophore model: $D_1$, $A_1^-$, $A_2^-$, D/A, $H_3$ and $H_2$ as shown in FIG. 6(a). The NH group corresponding to $D_1$ element shares hydrogen atom with side-chain carbonyl oxygen atom of Asn-103 residue. The oxygen atoms from the sulfonyl group (nearest to the head substructure (Rc)) which correspond to $A_1^-$ element involve electrostatic interactions with the side-chain ammonium group of Lys-246 residue. The oxygen atoms from remaining sulfonyl group in the anchor substructure correspond to element $A_2^-$ and accepts the hydrogen atom from side-chain hydroxyl group of Ser-72 residue. The oxo group corresponding to D/A element interacts with the main-chain NH group of residue Gln-248 via hydrogen bond. Two $CH_2$ groups from piperazinyl radical correspond with $H_3$ element and form hydrophobic interactions with the side-chain of residues Val-97 and Ile-113. The $CH_3$ group corresponding to $H_2$ element involves hydrophobic interactions with aliphatic portion of butylammonium side-chain of residue Lys-246, particularity with CR and CO carbon atoms.

Anchor A-SIJ118

The anchor substructure A-SIJ118 contains the following elements of the pharmacophore model: $D_1, A_1^-, A_2^-, H_3$ and $H_2$ as described in FIG. 6(b). The NH group which corresponds to element $D_1$ shares its hydrogen atom with side-chain carbonyl oxygen atom of Asp-98 residue. The oxygen atom corresponding to $A_1^-$ element forms hydrogen-bonding and electrostatic interactions with side-chain ammonium group of Lys-246 residue. The oxygen atoms from sulfonyl group correspond to $A_2^-$ element and participates in hydrogen bond accepting hydrogen atom from side-chain hydroxyl group of Ser-72 residue. The carbon atoms from pyrrol group which correspond to $H_3$ element form hydrophobic interactions with side-chain of residues Val-97 and Ile-113 and those who correspond to element $H_2$ involve hydrophobic interactions with the aliphatic portion of butylammonium side-chain of Lys-246 residue, particularity Cβ y Cδ carbon atoms.

Anchor A-SIJ121

The anchor substructure A-SIJ121 contains the following elements of the pharmacophore model: $D_2, A_1^-, A_2^-$ and $H_2$ as shown in FIG. 6(c). The NH group which corresponds to $D_2$ element shares its hydrogen atom with main-chain carbonyl group oxygen of Lys-246 residue. The oxygen atoms from the sulfonyl group corresponding to $A_1^-$ involve electrostatic interactions and hydrogen bond with side-chain ammonium group of Lys-246 residue. The oxygen atom and/or the sulfur atom which corresponds to $A_2^-$ element form hydrogen bond with the side-chain hydroxyl group of Ser-72 residue. The carbon atoms corresponding to $H_2$ element participate in hydrophobic interactions with the aliphatic portion of butylammonium side-chain of Lys-246 residue, particularity, with Cβ and Cδ carbon atoms.

Example 5

Experimental Assays

Inhibition of Viral Infection in Vero Cells.

With the aim to demonstrate the ability of the chemical compounds described herein to inhibit in vitro Dengue virus infection, these were evaluated in plaque inhibition assay in Vero cells.

Vero cells were grown in 24-wells plates until the monolayer reached approximately 90% confluence and two washes of the monolayer were done with medium MEM without SFB. Preparations of DEN2 virus equivalent to a multiplicity of infection of 0.1 were preincubated in MEM medium with and without presence of chemical compounds (100 uM) for about 1 hour at room temperature. Then, the virus/compounds mixture and virus/control mixture were incubated with monolayers for 1 hour at 37° C. After finished incubation, the cells were washed again and incubated during 5 days at 37° C. in high-density medium (MEM supplemented with non-essential amino acids, SFB 1%, carboxymethylcellulose 1%) to facilitate formation of lysis plaques. Blue Black Naphtol 0.1% in sodium acetate 0.15 mol/L was used for staining. In each experiment two replics were tested for each point and three independent determinations were done. The percentage of infection inhibition was calculated according to the following expression:

$$I = 100 \times \left[ 1 - \frac{No.plaques}{No.Plaques.control.virus.} \right]$$

As shown in Table 3, the chemical compounds described in the present invention show antiviral activity (I) against the DEN2 virus at the concentration tested. The antiviral effect observed for 80% of the chemical compounds is moderate (30%≤R<70%) or strong (70%≤I≤100%). The set of active chemical compounds include compounds containing different anchor substructures, as well as different head substructures for an individual anchor substructure, indicating the feasibility of the antiviral design described in this invention starting from diverse chemical "cores".

TABLE 3

Measurement of in vitro antiviral effect against DEN2 virus of several chemical compounds described in the present invention.

| Compound (identifer) | Inhibition (%) |
|---|---|
| 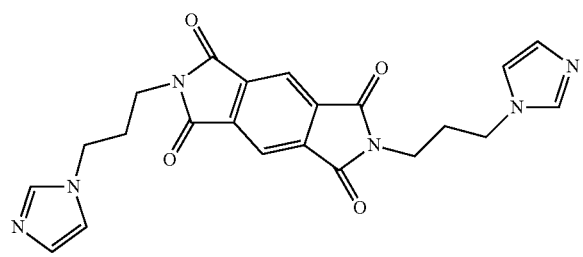 [SMILES: O=c1c2cc3c(=O)n(CCCn4ccnc4)c(=O)c3cc2c(=O)n1CCCn1ccnc1] | – |

TABLE 3-continued

Measurement of in vitro antiviral effect against DEN2 virus of several chemical compounds described in the present invention.

| Compound (identifer) | Inhibition (%) |
|---|---|
| C-SIJ01002 | ++ |
| C-SIJ01003 | + |
| C-SIJ01006 | ++ |
| C-SIJ01008 | + |
| C-SIJ01009 | ++ |
| C-SIJ01020 | ++ |

TABLE 3-continued

Measurement of in vitro antiviral effect against DEN2 virus of several chemical compounds described in the present invention.

| Compound (identifer) | Inhibition (%) |
| --- | --- |
| C-SIJ01023 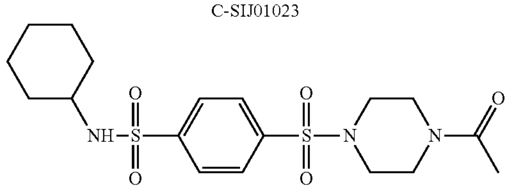  | ++ |
| C-SIJ01026 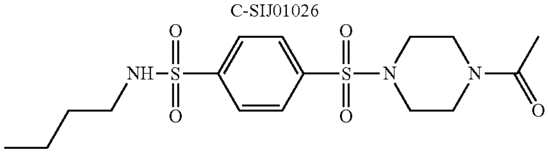  | + |
| C-SIJ01031 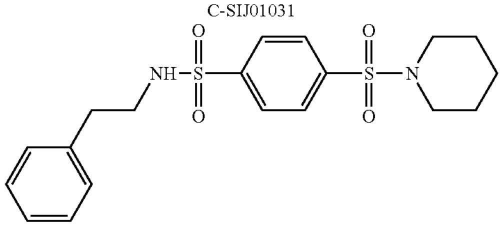  | ++ |
| C-SIJ01033 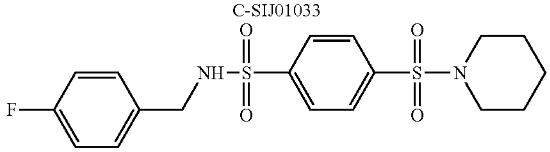  | + |
| C-SIJ01062 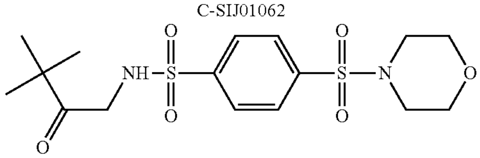  | ++ |
| C-SIJ06102 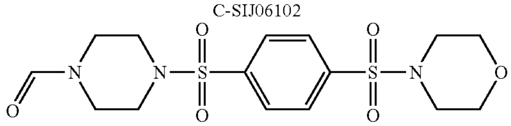  | + |
| C-SIJ06111 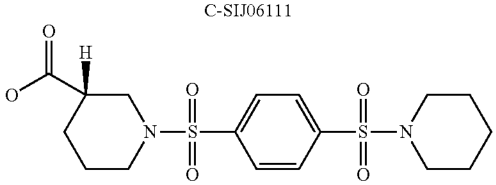  | ++ |
| 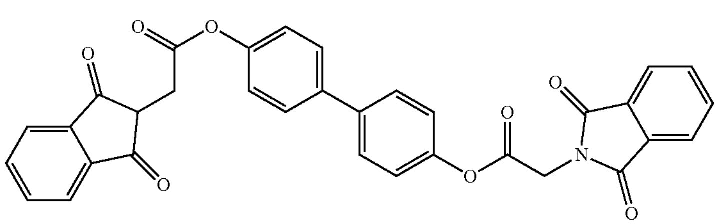  | – |

TABLE 3-continued
Measurement of in vitro antiviral effect against DEN2 virus of several chemical compounds described in the present invention.
| Compound (identifer) | Inhibition (%) |
|---|---|
| C-SIJ01034 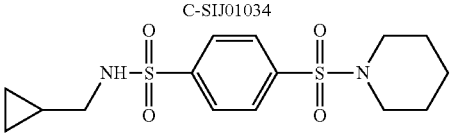 | + |
| C-SIJ01039 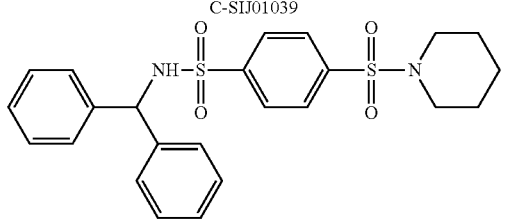 | ++ |
| C-SIJ01042 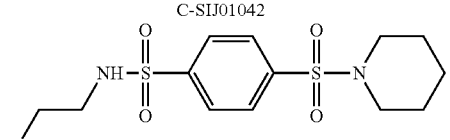 | ++ |
| C-SJI01045 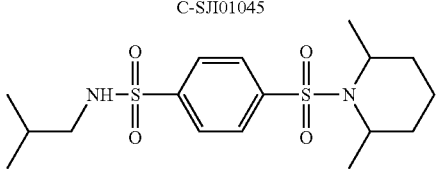 | + |
| C-SIJ01047 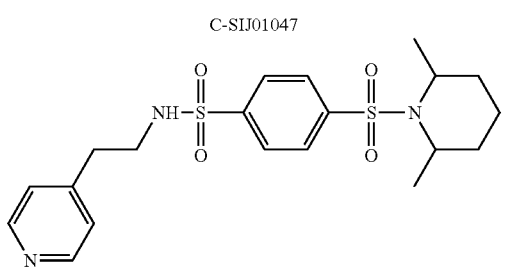 | ++ |
| C-SIJ01051 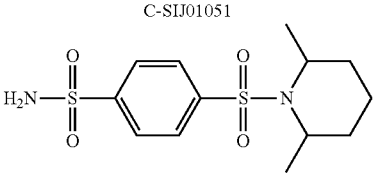 | + |
| C-SIJ01056 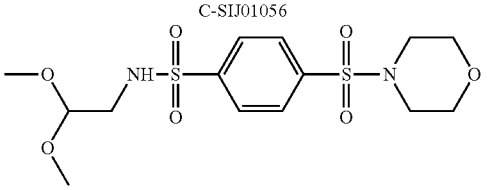 | ++ |

TABLE 3-continued

Measurement of in vitro antiviral effect against DEN2 virus of several chemical compounds described in the present invention.

| Compound (identifer) | Inhibition (%) |
|---|---|
| C-SIJ01066 | ++ |
| C-SIJ04078 | ++ |
| C-SIJ06097 | ++ |
| C-SIJ06099 | + |
| C-SIJ06103 | ++ |
| C-SIJ12143 | ++ |

++ refers to 70% ≤ I ≤ 100%

+ refers to 30% ≤ I < 100%

− refers to 30% < I ≤ 0%

Evaluation of Toxicity of Chemical Compounds.

To discard that the observed antiviral activity might be due to cellular alterations and cytotoxicity induced by the compounds, monolayers of Vero cells were exposed for 24 hours to solutions of these compounds prepared at a concentration of 500 uM and cell viability was determined by testing MTT (cell proliferation assay TACS™, R&D systems, Minneapilis, Minn.). There was no significant difference in viability of cells treated with chemical compounds and control cell not treated or treated with DMSO.

Specificity of the Inhibitory Activity.

In order to determine if chemical compounds specifically inhibit the cells infected by Dengue virus (and other related flavivirus), it was tested the inhibitory effect of these chemical compounds against unrelated viruses such as vaccinia virus and mengo virus. None of these compounds showed significant inhibitory effect against these viruses.

The invention claimed is:

1. A method of treating Dengue virus in a patient infected therewith comprising administering to the patient a pharmaceutically acceptable composition comprising one or more compounds selected from the group consisting of:

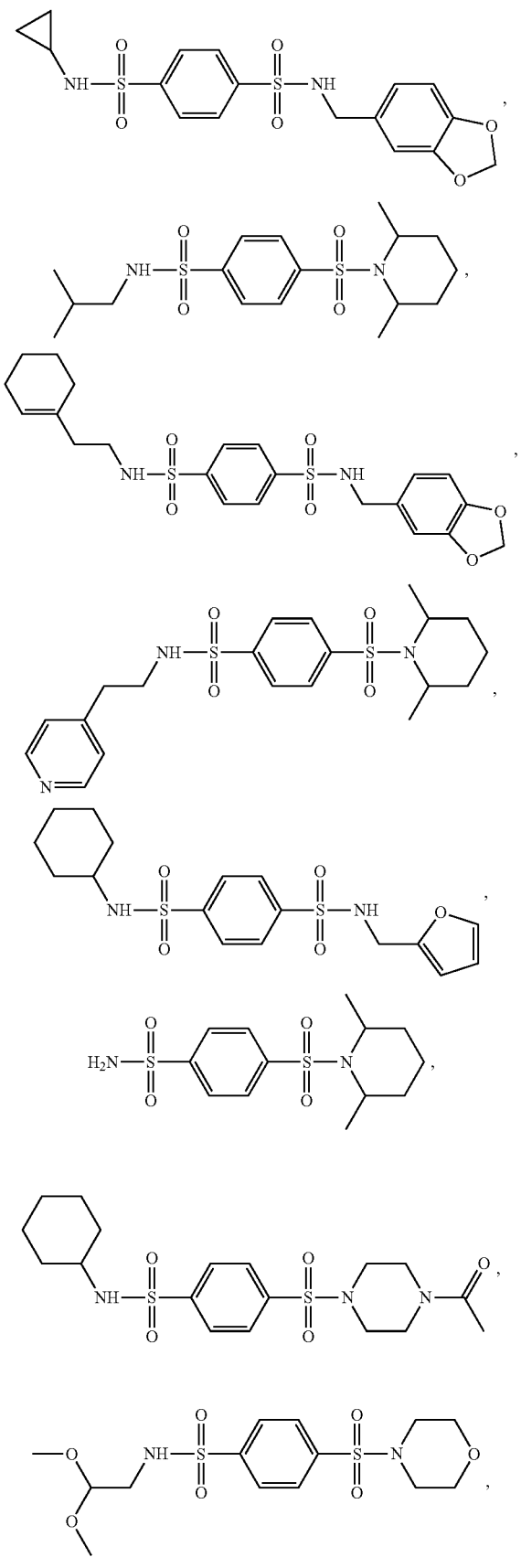

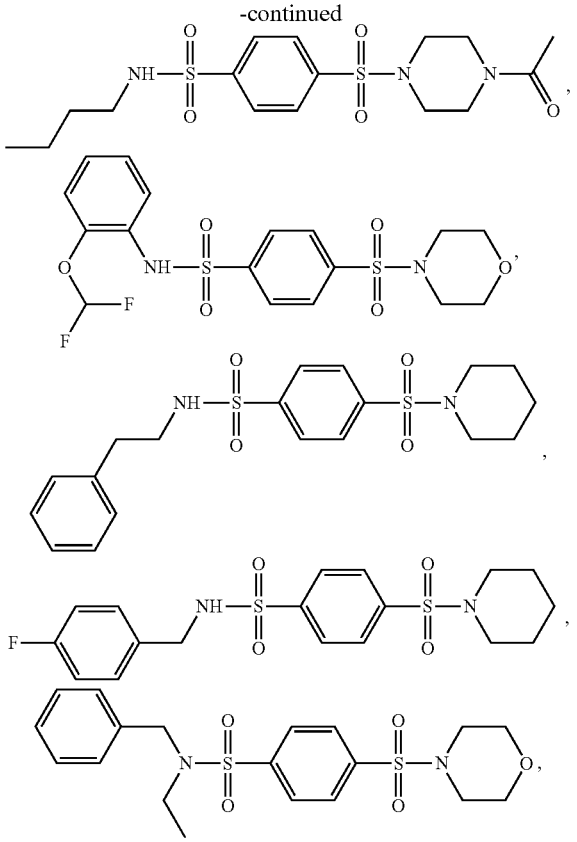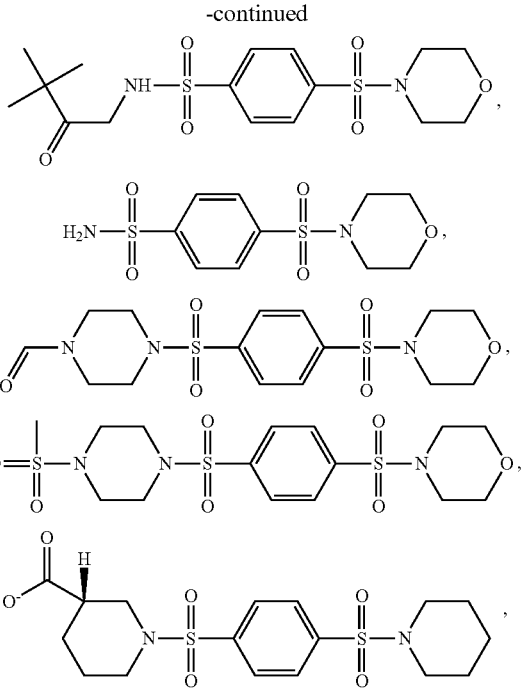
and pharmaceutically acceptable salts, tautomers, geometric isomers, enantiomers, diasterioisomers, and racemates thereof.
* * * * *

UNITED STATES PATENT AND TRADEMARK OFFICE
CERTIFICATE OF CORRECTION

PATENT NO. : 8,722,742 B2
APPLICATION NO. : 12/919416
DATED : May 13, 2014
INVENTOR(S) : Reyes et al.

It is certified that error appears in the above-identified patent and that said Letters Patent is hereby corrected as shown below:

IN THE SPECIFICATION:

Column 2, line 57:

Now reads: "That"

Should read: --Thai--

Column 2, line 63:

Now reads: "That"

Should read: --Thai--

Column 8, line 55:

Now reads: "Bressaneffi"

Should read: --Bressanelli--

Column 105, line 11:

Now reads: "CR and CO"

Should read: --C$\beta$ and C$\delta$--

Signed and Sealed this
Second Day of September, 2014

Michelle K. Lee
*Deputy Director of the United States Patent and Trademark Office*